(12) United States Patent
Jung et al.

(10) Patent No.: US 8,429,225 B2
(45) Date of Patent: *Apr. 23, 2013

(54) ACQUISITION AND PRESENTATION OF DATA INDICATIVE OF AN EXTENT OF CONGRUENCE BETWEEN INFERRED MENTAL STATES OF AUTHORING USERS

(75) Inventors: Edward K. Y. Jung, Bellevue, WA (US); Eric C. Leuthardt, St. Louis, MO (US); Royce A. Levien, Lexington, MA (US); Robert W. Lord, Seattle, WA (US); Mark A. Malamud, Seattle, WA (US); John D. Rinaldo, Jr., Bellevue, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/135,462

(22) Filed: Jul. 5, 2011

(65) Prior Publication Data

US 2011/0270914 A1 Nov. 3, 2011

Related U.S. Application Data

(63) Continuation-in-part of application No. 12/287,687, filed on Oct. 10, 2008, and a continuation of application No. 12/288,008, filed on Oct. 14, 2008, now Pat. No. 8,005,894, and a continuation-in-part of application No. 12/154,686, filed on May 23, 2008, now Pat. No. 7,904,507, and a continuation-in-part of application No. 12/157,611, filed on Jun. 10, 2008, and a continuation-in-part of application No. 12/215,683, filed on Jun. 26, 2008, and a continuation-in-part of application No. 12/217,131, filed on Jun. 30, 2008, now Pat. No. 8,055,591, and a continuation-in-part of application No. 12/221,253, filed on Jul. 29, 2008, and a continuation-in-part of application No. 12/221,197, filed on Jul. 30, 2008, and a continuation-in-part of application No. 12/229,517, filed on Aug. 21, 2008, now Pat. No. 8,065,360, and a continuation-in-part of application No. 12/231,302, filed on Aug. 29, 2008, and a continuation-in-part of application No. 12/284,348, filed on Sep. 19, 2008, and a continuation-in-part of application No. 12/284,710, filed on Sep. 23, 2008.

(51) Int. Cl.
*G06F 17/30* (2006.01)
*G06F 15/16* (2006.01)

(52) U.S. Cl.
USPC ............... 709/203; 709/220; 709/228; 707/3; 707/10

(58) Field of Classification Search .................. 709/203, 709/220, 224, 232; 707/3, 10
See application file for complete search history.

(56) References Cited

U.S. PATENT DOCUMENTS 5,715,374 A 2/1998 Heckerman et al.
5,724,698 A 3/1998 Mondragon
(Continued)

OTHER PUBLICATIONS

U.S. Appl. No. 12/931,359, Jung et al.
(Continued)

*Primary Examiner* — Khanh Dinh

(57) ABSTRACT

A computationally implemented method includes, but is not limited to: acquiring a first inference data indicative of an inferred mental state of a first authoring user in connection with a particular item of an electronic document, acquiring a second inference data indicative of an inferred mental state of a second authoring user in connection with the particular item of the electronic document; comparing the first inference data with the second inference data; and presenting data indicative of an extent of congruity between the inferred mental state of the first authoring user and the inferred mental state of the second authoring user based, at least in part, on said comparing. In addition to the foregoing, other method aspects are described in the claims, drawings, and text forming a part of the present disclosure.

47 Claims, 40 Drawing Sheets

U.S. PATENT DOCUMENTS

| | | | |
|---|---|---|---|
| 5,724,968 A * | 3/1998 | Iliff | 600/300 |
| 5,740,549 A | 4/1998 | Reilly et al. | |
| 5,761,512 A | 6/1998 | Breslau et al. | |
| 6,113,540 A | 9/2000 | Iliff | |
| 6,523,009 B1 | 2/2003 | Wilkins | |
| 6,573,927 B2 | 6/2003 | Parulski et al. | |
| 6,591,296 B1 | 7/2003 | Ghanime | |
| 7,300,402 B2 | 11/2007 | Iliff | |
| 7,406,307 B2 | 7/2008 | Manto | |
| 7,483,899 B2 | 1/2009 | Berry et al. | |
| 7,698,255 B2 | 4/2010 | Goodwin et al. | |
| 7,753,795 B2 | 7/2010 | Harris et al. | |
| 7,904,507 B2 * | 3/2011 | Jung et al. | 709/203 |
| 7,933,897 B2 * | 4/2011 | Jones et al. | 707/723 |
| 8,005,984 B2 * | 8/2011 | Campbell et al. | 709/238 |
| 2002/0065836 A1 | 5/2002 | Sasaki | |
| 2002/0095089 A1 | 7/2002 | Yamamoto et al. | |
| 2002/0193670 A1 | 12/2002 | Garfield et al. | |
| 2003/0028647 A1 | 2/2003 | Grosu | |
| 2003/0037063 A1 | 2/2003 | Schwartz | |
| 2003/0191568 A1 | 10/2003 | Breed | |
| 2004/0001086 A1 | 1/2004 | Brown et al. | |
| 2004/0001090 A1 | 1/2004 | Brown et al. | |
| 2004/0230549 A1 | 11/2004 | Freer et al. | |
| 2004/0236236 A1 | 11/2004 | Yanagidaira et al. | |
| 2005/0010637 A1 | 1/2005 | Dempski et al. | |
| 2005/0078804 A1 | 4/2005 | Yomoda | |
| 2006/0010240 A1 | 1/2006 | Chuah | |
| 2006/0112111 A1 | 5/2006 | Tseng et al. | |
| 2006/0184464 A1 * | 8/2006 | Tseng et al. | 706/14 |
| 2006/0206833 A1 | 9/2006 | Capper et al. | |
| 2007/0038054 A1 | 2/2007 | Zhou et al. | |
| 2007/0043590 A1 | 2/2007 | Lee | |
| 2007/0093965 A1 | 4/2007 | Harrison et al. | |
| 2007/0192038 A1 | 8/2007 | Kameyama | |
| 2008/0001600 A1 | 1/2008 | deCharms | |
| 2008/0027984 A1 | 1/2008 | Perdomo et al. | |
| 2008/0059570 A1 | 3/2008 | Bill | |
| 2008/0065468 A1 | 3/2008 | Berg et al. | |
| 2008/0096532 A1 | 4/2008 | Lyle et al. | |
| 2008/0114266 A1 | 5/2008 | Shen et al. | |
| 2008/0120129 A1 | 5/2008 | Seubert et al. | |
| 2008/0139889 A1 | 6/2008 | Bagan | |
| 2008/0162393 A1 | 7/2008 | Iliff | |
| 2008/0162649 A1 | 7/2008 | Lee et al. | |
| 2008/0181381 A1 | 7/2008 | Manto | |
| 2008/0215972 A1 | 9/2008 | Zalewski et al. | |
| 2008/0215973 A1 | 9/2008 | Zalewski et al. | |
| 2008/0235582 A1 | 9/2008 | Zalewski et al. | |
| 2008/0243825 A1 | 10/2008 | Staddon et al. | |
| 2009/0002178 A1 | 1/2009 | Guday et al. | |
| 2009/0030886 A1 | 1/2009 | Pandeya | |
| 2009/0055484 A1 | 2/2009 | Vuong et al. | |
| 2009/0063992 A1 | 3/2009 | Gandhi et al. | |
| 2009/0193344 A1 | 7/2009 | Smyers | |
| 2009/0251457 A1 | 10/2009 | Walker et al. | |
| 2009/0271375 A1 | 10/2009 | Hyde et al. | |
| 2010/0095362 A1 * | 4/2010 | Boberg et al. | 726/7 |
| 2010/0135369 A1 | 6/2010 | Hagl et al. | |

OTHER PUBLICATIONS

ABOUT.COM.: Email Webpage; printed on Aug. 15, 2008; p. 1 located at http://email.about.com/gi/dynamic/offsite.htm?zi=1/XJ&sdn=email&zu=http%3A%2F%2Fwww.pointofmail.com%2F.

Ambler et al.; "Salience and Choice: Neural Correlates of Shopping Decisions"; Psychology & Marketing; Apr. 2004; pp. 247-261; vol. 21; No. 4; Wiley Periodicals, Inc.

Appenzeller et al.; "The Mobile People Architecture—Technical Report: CSL-TR-99-777"; Jan. 1999; pp. 1-10 (12 pages total incl. title page/abstract and copyright information); located at ftp://reports.stanford.edu/pub/cstr/reports/csl/tr/99/777/CSL-TR-99-777.pdf; Stanford University.

Bergman et al.; "A Personal Email Assistant"; HPInvent Website: prnted on Aug. 15, 2008; pp. 1-22 (23 pages total incl. summary page); located at http://www.hpl.hp.com/techreports/2002/HPL-2002-236.pdf; Hewlett-Packard Company 2002.

Cabeza et al.; "Imaging Cognition II: An Empirical Review of 275 PET and fMRI Studies"; Journal of Cognitive Neuroscience; 2000; pp. 1-47; vol. 12; No. 1; Massachusetts Institute of Technology.

CENTIPAID.COM; "Getting the Best Out of Surgemail's SPAM Features"; bearing dates of 2002-2006 and printed on Aug. 13, 2008; pp. 1-5; located at http://www.centipaid.com/en/support/surgemail.html; Centipaid Corporation.

Chance et al.; "A Novel Method for Fast Imaging of Brain Function, Non-Invasively, With Light"; Optics Express; May 11, 1998; pp. 411-423; vol. 2; No. 10; OSA.

Clearcontext; "User Guide"; bearing dates of 2003-2008 and printed on Aug. 15, 2008; pp. 1-4; located at http://www.clearcontext.com/user_guide/contacts.html; Clearcontext Corporation.

CommuniGatePro; "CommuniGate® Pro Version 5.1"; bearing dates of 1998-2007 and printed on Aug. 15, 2008; pp. 1-6; located at https://mx2.arl.org/Guide/default.html; Stalker Software, Inc.

Critical Path; "Critical Path: Putting Mobile Email in Context"; bearing a date of Aug. 11, 2005 and printed on Aug. 13, 2008; pp. 1-2; located at http://www.cbronline.com/article_feature.asp?guid=D9E4E0B0-BE6A-4928-8857-3A3682D852C1; CBR and CBRonline.com.

Goodmail Systems; "Certified Email: How it Works"; printed on Aug. 13, 2008: p. 1: located at http://www.goodmailsystems.com/products/certified-email/how_it_works.php.

Huang et al.; "Map Web: A Location-Based Converged Communications Platform"; Bell Labs Technical Journal—Lucent Technologies Inc.; 2006; pp. 159-171; Wiley Periodicals, Inc.

iNovaLive: "iNovaLive: Email Solutions Through Email Evolution website": bearing a date of 2006 and printed on Aug. 15, 2008; pp. 1-2; located at http://inovalive.com/site/index; iNovaSoft Ltd.

Kenning et al.; "NeuroEconomics: An Overview from an Economic Perspective"; Brain Research Bulletin; 2005; pp. 343-354; vol. 67; Elsevier Inc.

Lee et al.; "What is 'Neuromarketing'? A Discussion and Agenda for Future Research"; International Journal of Psychophysiology; bearing dates of 2006 and 2007; pp. 199-204; vol. 63; Elsevier B.V.

Matthews et al.; "Applications of fMRI in Translational Medicine and Clinical Practice"; Nature Reviews/Neuroscience; Sep. 2006; pp. 732-744; vol. 7; Nature Publishing Group.

Murphy, Kevin; "Pay-Per-Email Scheme Draws Critics"; bearing a date of Feb. 7, 2006 and printed on Aug. 13, 2008; pp. 1-3; located at http://www.cbronline.com/article_news.asp?guid=A921B4EA-A489-4B5C-8053-423F46499767; CBR and CBRonline.com.

Nedos et al.; "LATTE: Location and Time Triggered Email"; pp. 1-14; located at https://www.cs.tcd.ie/publications/tech-reports/reports.04/TCD-CS-2004-32.pdf; Trinity College, Dublin, Ireland.

Parc Research; "Content-Centric Networking: Parc's Strategy for Pioneering a Self-Organizing Network That Meets Information Needs"; pp. 1-4; Xerox Corporation; located at: http://www.parc.xerox.com/research/projects/networking/contentcentric/mediabackgrounder.html; printed on Mar. 2, 2009.

Parc Research; "Content Centric Networking"; bearing dates of 2002-2007; printed on Aug. 15, 2008; pp. 1-2; located at http://www.parc.xerox.com/research/projects/networking/contentcentric/default.html; Palo Alto Research Center Incorporated.

POINTOFMAIL.COM.; "Advanced Email Experience™"; bearing dates of 1999-2008 and printed on Aug. 15, 2008; p. 1; located at http://email.about.com/gi/dynamic/offsite.htm?zi=1/XJ&sdn=email&zu=http%3A%2F%2Fwww.readnotify.com%2F.

Roecker et al.; "Context-Dependent Email Notification Using Ambient Displays and Mobile Devices"; 2005; pp. 137-138; located at http://ieeexplore.ieee.org/iel5/10045/32238/01505288.pdf?tp=&isnumber=32238&arnumber=1505288; IEEE.

TECHCRUNCH.COM; "Seriosity to Fix Email Overload (Or Not)" blog; bearing a date of Feb. 28, 2007 and printed on Aug. 13, 2008; pp. 1-12; located at http://www.techcrunch.com/2007/02/28/seriosity-to-fix-email-overload-or-not/all-comments/#comments.

Terdiman, Daniel; "A Cure for E-Mail Attention Disorder?"; CNET News.com; Feb. 28, 2007 and printed on Aug. 13, 2008; pp. 1-4; located at http://news.com.com/2100-1038_3-6162798.html; CNET Networks, Inc., a CBS Company.

Tschabitscher, Heinz; "BigString.com—Free Email Service"; About.com: Email; printed on Aug. 13, 2008; pp. 1-2; located at http://email.about.com/od/freeemailreviews/gr/bigstring_com.htm.

Tschabitscher, Heinz; "Confimax—Certified Email Service"; About.com: Email; printed on Aug. 13, 2008; pp. 1-2; located at http://email.about.com/cs/oepluginreviews/gr/confirmax.htm.

Tschabitscher, Heinz; "DidTheyReadIt—Certified Email Service"; About.com: Email; printed on Aug. 13, 2008; pp. 1-2; located at http://email.about.com/od/windowsreturnreceipts/gr/didtheyreadit.htm.

Tschabitscher, Heinz; "E-mail Secure—Certified Email Service"; About.com: Email; printed on Aug. 13, 2008; pp. 1-2; located at http://email.about.com/od/windowsreturnreceipts/gr/e_mailsecure.htm.

Tschabitscher, Heinz; "Pointofmail 5.5—Certified Email Service"; About.com: Email; printed on Aug. 13, 2008; pp. 1-2; located at http://email.about.com/od/windowsreturnreceipts/gr/pointofmail.htm.

Tschabitscher, Heinz; "ReadNotify—Certified Email Service"; About.com: Email; printed on Aug. 13, 2008; pp. 1-2; located at http://email.about.com/od/windowsreturnreceipts/gr/readnotify.htm.

TWITTER.COM website located at http://twitter.com; [No document provided].

Westen et al.; "Neural Bases of Motivated Reasoning: An fMRI Study of Emotional Constraints on Partisan Political Judgment in the 2004 U.S. Presidential Election"; Journal of Cognitive Neuroscience; 2006; pp. 1947-1958; vol. 18; No. 11; Massachusetts Institute of Technology.

* cited by examiner

38 Presentation Module

212 Transmission Module

213 Display Module

FIG. 2d

32 Inference Data Association Module

110 Inference Data Inclusion Module

FIG. 2f

31 Source Identity Acquisition Module

201 Authoring User ID Acquisition Module

203 Database or library ID Acquisition Module

202 Inference Technique or Model ID Acquisition Module

204 Sensor ID Acquisition Module

FIG. 2g

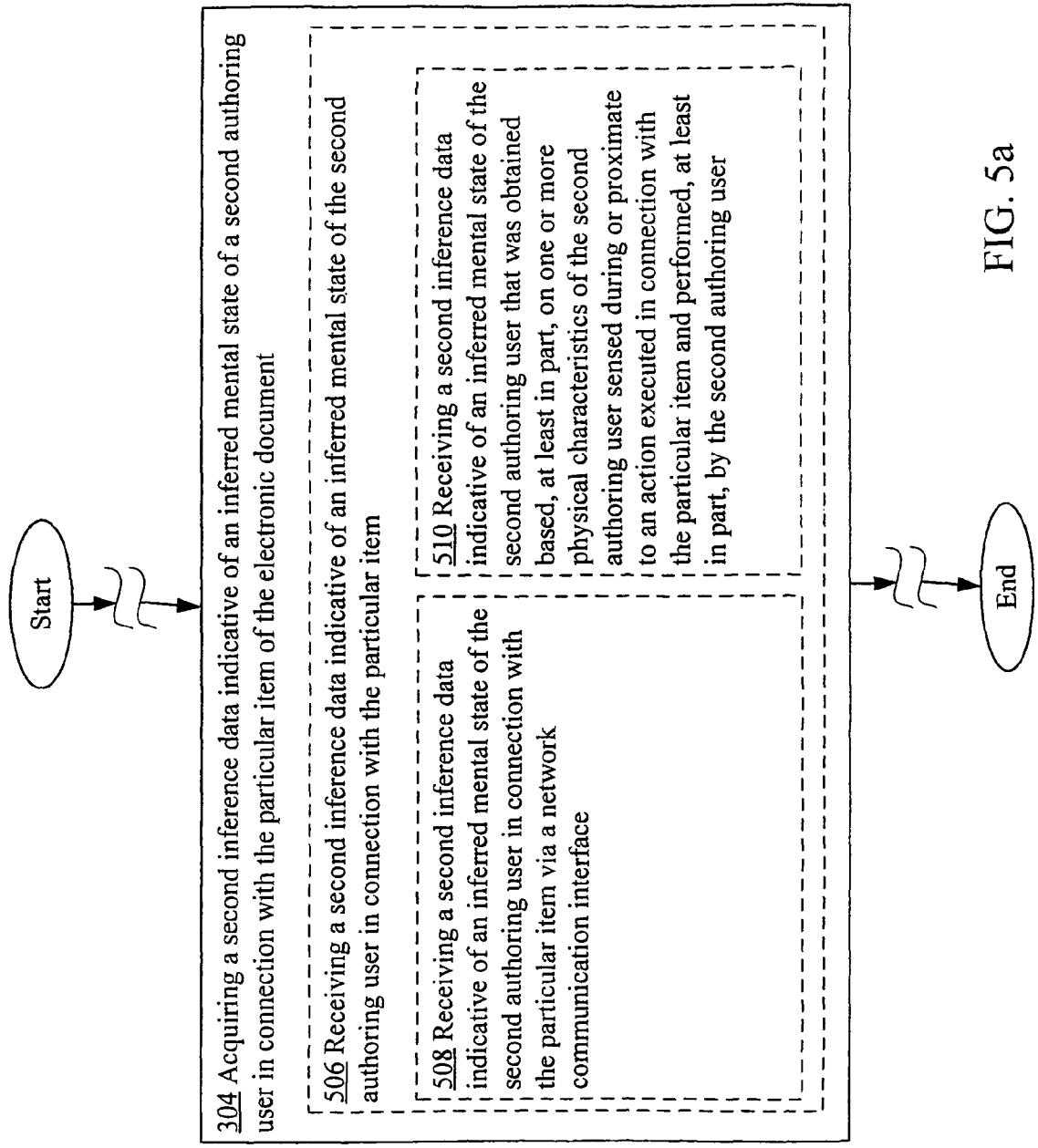

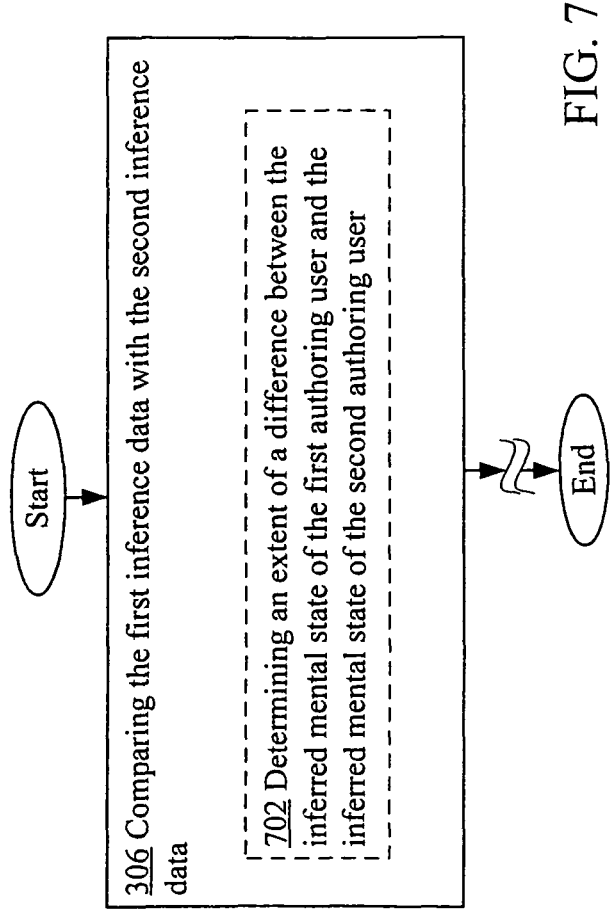

ACQUISITION AND PRESENTATION OF DATA INDICATIVE OF AN EXTENT OF CONGRUENCE BETWEEN INFERRED MENTAL STATES OF AUTHORING USERS

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

Related Applications

For purposes of the USPTO extra-statutory requirements, the present application constitutes a continuation-in-part of U.S. patent application Ser. No. 12/287,687, entitled ACQUISITION AND PRESENTATION OF DATA INDICATIVE OF AN EXTENT OF CONGRUENCE BETWEEN INFERRED MENTAL STATES OF AUTHORING USERS, naming Edward K. Y. Jung, Eric C. Leuthardt, Royce A. Levien, Robert W. Lord, Mark A. Malamud, John D. Rinaldo, Jr. and Lowell L. Wood, Jr. as inventors, filed 10 Oct. 2008, which is currently co-pending, or is an application of which a currently co-pending application is entitled to the benefit of the filing date.

For purposes of the USPTO extra-statutory requirements, the present application constitutes a continuation of U.S. patent application Ser. No. 12/288,008, entitled ACQUISITION AND PRESENTATION OF DATA INDICATIVE OF AN EXTENT OF CONGRUENCE BETWEEN INFERRED MENTAL STATES OF AUTHORING USERS, naming Edward K. Y. Jung, Eric C. Leuthardt, Royce A. Levien, Robert W. Lord, Mark A. Malamud, John D. Rinaldo, Jr. and Lowell L. Wood, Jr. as inventors, filed 14 Oct. 2008 now U.S. Pat. No. 8,005,894.

For purposes of the USPTO extra-statutory requirements, the present application constitutes a continuation-in-part of U.S. patent application Ser. No. 12/154,686, entitled DETERMINATION OF EXTENT OF CONGRUITY BETWEEN OBSERVATION OF AUTHORING USER AND OBSERVATION OF RECEIVING USER, naming Edward K. Y. Jung, Eric C. Leuthardt, Royce A. Levien, Robert W. Lord, Mark A. Malamud, John D. Rinaldo, Jr. and Lowell L. Wood, Jr. as inventors, filed 23 May 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/157,611, entitled DETERMINATION OF EXTENT OF CONGRUITY BETWEEN OBSERVATION OF AUTHORING USER AND OBSERVATION OF RECEIVING USER, naming Edward K. Y. Jung, Eric C. Leuthardt, Royce A. Levien, Robert W. Lord, Mark A. Malamud, John D. Rinaldo, Jr. and Lowell L. Wood, Jr. as inventors, filed 10 Jun. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/215,683, entitled ACQUISITION AND ASSOCIATION OF DATA INDICATIVE OF AN INFERRED MENTAL STATE OF AN AUTHORING USER, naming Edward K. Y. Jung, Eric C. Leuthardt, Royce A. Levien, Robert W. Lord, Mark A. Malamud, John D. Rinaldo, Jr. and Lowell L. Wood, Jr. as inventors, filed 26 Jun. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/217,131, entitled ACQUISITION AND ASSOCIATION OF DATA INDICATIVE OF AN INFERRED MENTAL STATE OF AN AUTHORING USER, naming Edward K. Y. Jung, Eric C. Leuthardt, Royce A. Levien, Robert W. Lord, Mark A. Malamud, John D. Rinaldo, Jr. and Lowell L. Wood, Jr. as inventors, filed 30 Jun. 2008 now U.S. Pat. No. 8,055,591.

For purposes of the USPTO extra-statutory requirements, the present application constitutes a continuation-in-part of U.S. patent application Ser. No. 12/221,253, entitled ACQUISITION AND PARTICULAR ASSOCIATION OF DATA INDICATIVE OF AN INFERRED MENTAL STATE OF AN AUTHORING USER, naming Edward K. Y. Jung, Eric C. Leuthardt, Royce A. Levien, Robert W. Lord, Mark A. Malamud, John D. Rinaldo, Jr. and Lowell L. Wood, Jr. as inventors, filed 29 Jul. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/221,197, entitled ACQUISITION AND PARTICULAR ASSOCIATION OF DATA INDICATIVE OF AN INFERRED MENTAL STATE OF AN AUTHORING USER, naming Edward K. Y. Jung, Eric C. Leuthardt, Royce A. Levien, Robert W. Lord, Mark A. Malamud, John D. Rinaldo, Jr. and Lowell L. Wood, Jr. as inventors, filed 30 Jul. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/229,517, entitled ACQUISITION AND PARTICULAR ASSOCIATION OF INFERENCE DATA INDICATIVE OF AN INFERRED MENTAL STATE OF AN AUTHORING USER AND SOURCE IDENTITY DATA, naming Edward K. Y. Jung, Eric C. Leuthardt, Royce A. Levien, Robert W. Lord, Mark A. Malamud, John D. Rinaldo, Jr. and Lowell L. Wood, Jr. as inventors, filed 21 Aug. 2008 U.S. Pat. No. 8,065,360.

For purposes of the USPTO extra-statutory requirements, the present application constitutes a continuation-in-part of U.S. patent application Ser. No. 12/231,302, entitled ACQUISITION AND PARTICULAR ASSOCIATION OF INFERENCE DATA INDICATIVE OF AN INFERRED MENTAL STATE OF AN AUTHORING USER AND SOURCE IDENTITY DATA, naming Edward K. Y. Jung, Eric C. Leuthardt, Royce A. Levien, Robert W. Lord, Mark A. Malamud, John D. Rinaldo, Jr. and Lowell L. Wood, Jr. as inventors, filed 29 Aug. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/284,348, entitled ACQUISITION AND PARTICULAR ASSOCIATION OF INFERENCE DATA INDICATIVE OF INFERRED MENTAL STATES OF AUTHORING USERS, naming Edward K. Y. Jung, Eric C. Leuthardt, Royce A. Levien, Robert W. Lord, Mark A. Malamud, John D. Rinaldo, Jr. and Lowell L. Wood, Jr. as inventors, filed 19 Sep. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/284,710, entitled ACQUISITION AND PARTICULAR ASSOCIATION OF INFERENCE DATA INDICATIVE OF INFERRED MENTAL STATES OF AUTHORING USERS, naming Edward K. Y. Jung, Eric C. Leuthardt, Royce A. Levien, Robert W. Lord, Mark A. Malamud, John D. Rinaldo, Jr. and Lowell L. Wood, Jr. as inventors, filed 23 Sep. 2008, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

SUMMARY

A computationally implemented method includes, but is not limited to: acquiring a first inference data indicative of an inferred mental state of a first authoring user in connection with a particular item of an electronic document; acquiring a second inference data indicative of an inferred mental state of a second authoring user in connection with the particular item of the electronic document; comparing the first inference data with the second inference data; and presenting data indicative of an extent of congruity between the inferred mental state of the first authoring user and the inferred mental state of the second authoring user based, at least in part, on said comparing. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

A computationally implemented system includes, but is not limited to: means for acquiring a first inference data indicative of an inferred mental state of a first authoring user in connection with a particular item of an electronic document; means for acquiring a second inference data indicative of an inferred mental state of a second authoring user in connection with the particular item of the electronic document; means for comparing the first inference data with the second inference data; and means for presenting data indicative of an extent of congruity between the inferred mental state of the first authoring user and the inferred mental state of the second authoring user based, at least in part, on said comparing. In addition to the foregoing, other system aspects are described in the claims, drawings, and text forming a part of the present disclosure.

A computationally implemented system includes, but is not limited to: circuitry for acquiring a first inference data indicative of an inferred mental state of a first authoring user in connection with a particular item of an electronic document; circuitry for acquiring a second inference data indicative of an inferred mental state of a second authoring user in connection with the particular item of the electronic document; circuitry for comparing the first inference data with the second inference data; and circuitry for presenting data indicative of an extent of congruity between the inferred mental state of the first authoring user and the inferred mental state of the second authoring user based, at least in part, on said comparing. In addition to the foregoing, other system aspects are described in the claims, drawings, and text forming a part of the present disclosure.

A computer program product including a signal-bearing medium bearing one or more instructions for acquiring a first inference data indicative of an inferred mental state of a first authoring user in connection with a particular item of an electronic document; one or more instructions for acquiring a second inference data indicative of an inferred mental state of a second authoring user in connection with the particular item of the electronic document; one or more instructions for comparing the first inference data with the second inference data; and one or more instructions for presenting data indicative of an extent of congruity between the inferred mental state of the first authoring user and the inferred mental state of the second authoring user based, at least in part, on said comparing. In addition to the foregoing, other computer program product aspects are described in the claims, drawings, and text forming a part of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 2b shows another perspective of the inference data acquisition module 30 of FIG. 2a.

FIG. 2c shows another perspective of the comparison module 37 of FIG. 2a.

FIG. 2d shows another perspective of the presentation module 38 of FIG. 2a.

FIG. 2f shows another perspective of the inference data association module 32 of FIG. 2a.

FIG. 2g shows another perspective of the source identity acquisition module 31 of FIG. 2a.

FIG. 2h shows another perspective of the source identity association module 33 of FIG. 2a.

FIG. 2i shows another perspective of the action module 34 of FIG. 2a.

FIG. 2j shows another perspective of the time module 36 of FIG. 2a.

FIG. 2k shows another perspective of the one or more applications 40 of FIG. 2a.

FIG. 2l shows another perspective of the user interface 44 of FIG. 2a.

FIG. 2m shows another perspective of the one or more sensors 48 of FIG. 2a.

FIG. 5a is a high-level logic flowchart of a process depicting alternate implementations of the second inference data acquisition operation 304 of FIG. 3.

FIG. 5b is a high-level logic flowchart of a process depicting alternate implementations of operation 510 of FIG. 5a.

FIG. 6b is a high-level logic flowchart of a process depicting alternate implementations of the observation operation 604 of FIG. 6a.

FIG. 6c is a high-level logic flowchart of a process depicting more alternate implementations of the observation operation 604 of FIG. 6a.

DETAILED DESCRIPTION

Figure 1:
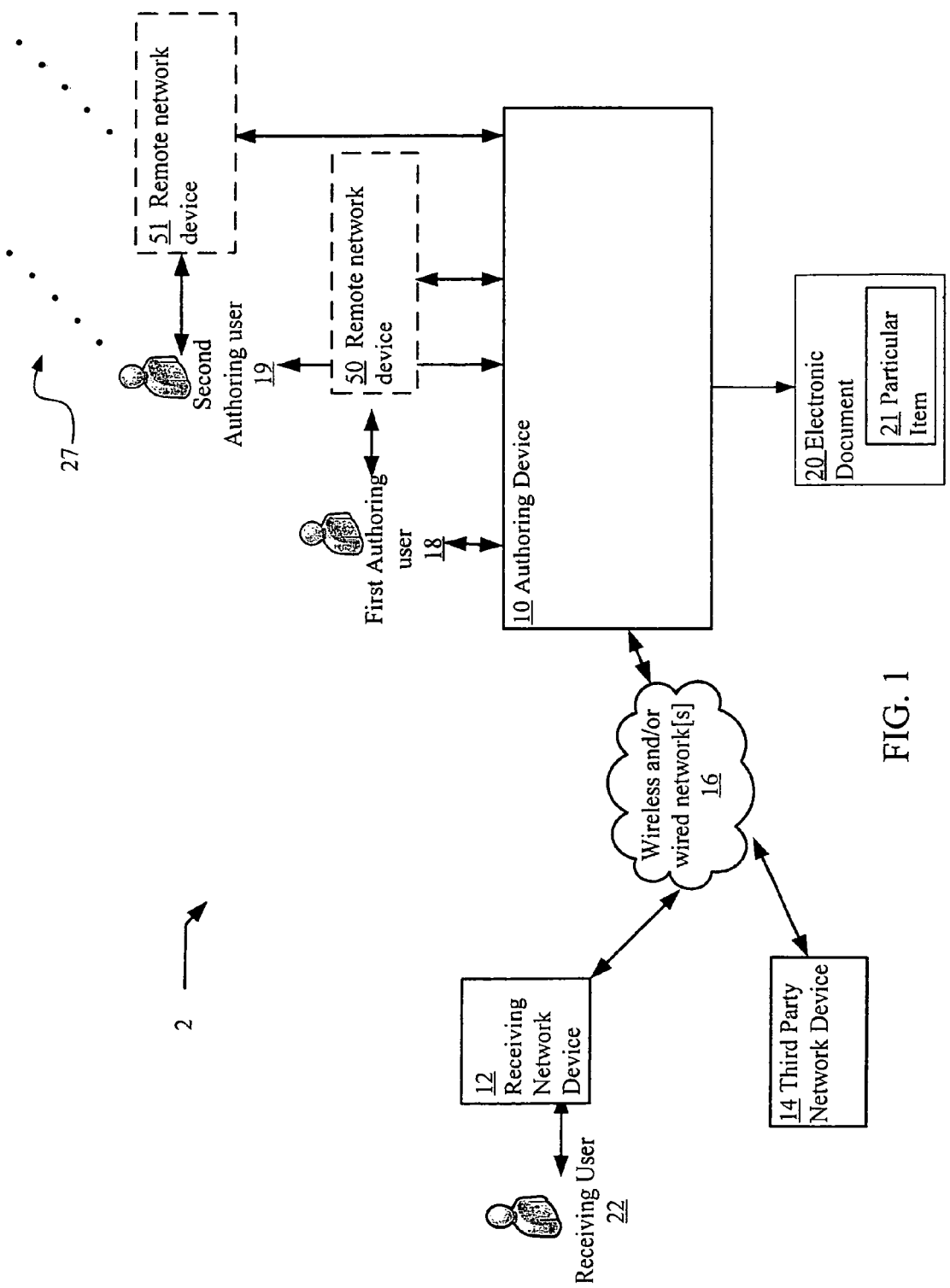
FIG. 1 shows a high-level block diagram of a network device operating in a network environment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Various embodiments of the present invention allows for the acquisition of inference data that may indicate the inferred mental states of two or more authoring users in connection with a particular item of an electronic document. Such data may then be associated with the particular item in order to, for example, facilitate the recipient of the electronic document in properly understanding the meaning and tone of the particular item when the particular item is presented to the recipient. In some embodiments, data indicative of the extent of congruity between the inferred mental states of the authoring users may be presented to the authoring users, the recipient, or a third party participant. By doing so, the proper intent and meaning of the particular item may be properly relayed to the recipient.

FIG. 1 illustrates an example environment in which one or more aspects of various embodiments may be implemented. In the illustrated environment, an exemplary system 2 may include at least an authoring device 10 that may be used by multiple authoring users (e.g., a first authoring user 18, a second authoring user 19, and/or other additional authoring users as indicated by ref. 27) in order to, for example, acquire and present data indicative of the extent of congruity between inferred mental states of the authoring users in connection with a particular item 21 of an electronic document 20.

In order to achieve such results, in some implementations, the authoring device 10 (and in some cases, remote network devices 50/51) may be particularly designed and configured to facilitate in the initial acquisition of inference data that may indicate the inferred mental states of multiple authoring users in connection with a particular item 21 of an electronic document 20. In various embodiments, the authoring device 10 may be further designed to associate the inference data to the particular item 21 and present data that indicate the level or degree of congruence between the inferred mental states of the authoring users. In some embodiments, the authoring device 10 may be particularly configured such that it may be used by the authoring users (e.g., authoring user 18, authoring user 19, and so forth) in order to communicate through one or more wireless and/or wired networks 16. The authoring device 10 may be any type of computing and/or communication device such as a server (e.g., network server), a personal computer (PC), a laptop computer, a personal digital assistant (PDA), a cellular telephone, a blackberry, and so forth. In the case where the authoring device 10 is a server, a remote network device 50/51 may be employed by an authoring user (e.g., first authoring user 18 or second authoring user 19) in order for the authoring user to communicate with the authoring device 10.

Unless indicated otherwise, the phrase "inference data," as will be used herein refers to data that may indicate the inferred mental state or states of one or more authoring users (e.g., first authoring user 18, second authoring user 19, and so forth) in connection with a particular item 21 of an electronic document 20. In contrast, the phrase "a first inference data," as used herein, may be in reference to inference data that may be specific to a particular authoring user, such as the first authoring user 18, that may indicate the inferred mental state of the first authoring user 18 in connection with the particular item 21. Likewise, the phrase "a second inference data," as used herein, may be in reference to inference data that is specific to, for example, the second authoring user 19 that may indicate the inferred mental state of the second authoring user 19 in connection with the particular item 21.

In various implementations, the authoring device 10 (as well as, in some cases, the remote network devices 50/51) may be further configured to acquire and associate source identity data that may provide one or more identities of one or more sources that may be the basis, at least in part, for the inference data acquired and associated by the authoring device 10. In doing so, a recipient of the electronic document 20, such as a receiving user 22 (e.g., via a receiving network device 12) or a third party (e.g., via a third party network device 14), may be facilitated in correctly interpreting the proper meaning and intent of the particular item 21 if and when the electronic document 20 is presented to the recipient. Note that for ease of illustration and explanation, the systems, processes, and operations to be described herein will be generally described with respect to only two authoring users (e.g., a first authoring user 18 and a second authoring user 19). However, those skilled in the art will recognize that these systems, processes, and operations may also be employed with respect to three or more authoring users in various alternative implementations.

In addition to acquiring and associating the inference data and source identity data, other types of information may also be acquired and associated with the particular item 21. For instance, and as will be further described herein, in some implementations the authoring device 10 may acquire and associate with the particular item 21 one or more time stamps and/or one or more indications of actions performed in connection with the particular item 21. In some cases, such information may be useful in associating inference data with the particular item 21.

In various implementations, the electronic document 20 may be any type of electronic file for storing and/or communicating data including, for example, a word processing document, a spread sheet, or an electronic message such as an email message, a text message, an instant message (IM), an audio message, a video message, or another type of electronic message. The particular item 21 may be any part or portion of the electronic document 20. For example, if the electronic document 20 is an email message or a word processing document, then the particular item 21 may be a passage, a paragraph, a sentence, a word, a phrase, an image, a symbol, an icon, a number, a letter; a format of a word or phrase (e.g., bold), or any other part or portion of the email message.

As will be further described, an inferred mental state of a subject (e.g., a first authoring user 18, a second authoring user 19, or a receiving user 22) may be a mental state that has been inferred based, at least in part, on one or more sensed or measured physical characteristics of the subject. The term "physical characteristics" as used herein may refer to external physical characteristics (e.g., facial expressions, skin characteristics, and/or iris characteristics) and/or physiological characteristics (e.g., blood oxygen or blood volume changes of a subject's brain, characteristics associated with the electrical activities of the subject's brain, cardiopulmonary characteristics, and so forth). In various embodiments, the sensing or measurement of the physical characteristics of the subject may be in connection with an "action" being executed by the subject with respect to a particular item 21.

For example, suppose the first authoring user 18 creates an electronic document 20 (e.g., an email message) containing a particular item 21, in this case, a passage that includes a humorous story, for transmission to the receiving user 22 with the intent to lighten the mood of the receiving user 22. Suppose further that after the electronic document 20 has been created by the first authoring user 18, and prior to the transmission of the electronic document 20, the particular item 21 is modified by the second authoring user 19 (e.g., the second authoring user 19 accessing and modifying via the authoring device 10 or via the remote network device 51) in order to make the humorous story (e.g., particular item 21) funnier. The authoring device 10 may then acquire a first inference data that may indicate an inferred mental state of the authoring user 18 in connection with the creation of the particular item 21 and a second inference data that may indicate an inferred mental state of the second authoring user 18 in connection with the modification of the particular item 21.

In some implementations, the acquisitions of the first and second inference data may be accomplished, at least in part, by sensing one or more physical characteristics of the first authoring user 18 during or proximate to the creation of the particular item 21 and sensing one or more physical characteristics of the second authoring user 19 during or proximate to the modification of the particular item 21. The sensing of the physical characteristics of the first and second authoring users 18 and 19 may be accomplished by the use of one or more sensors 48 that may be provided with the authoring device 10 and/or by the use of one or more sensors 48" (see FIG. 2t) provided with one or more remote network devices 50/51. The acquired first and second inference data may then be associated or tagged to the particular item 21 (e.g., passage). As will be further described, the association of the first and second inference data with the particular item 21 may be accomplished in any one of a number of ways including, for example, placing the first and the second inference data at specific locations in the electronic document 20.

In some implementations, after associating the first and second inference data to the particular item 21, the first and second inference data may then be provided or transmitted to a recipient (e.g., receiving user 22) by including the first and second inference data in the electronic document 20 or by other means (e.g., in another electronic message). In doing so, the receiving user 22 may determine an inferred mental state of the first authoring user 18 in connection with the creation of the particular item 21 and an inferred mental state of the second authoring user 19 in connection with the modification of the particular item 21. By determining the inferred mental states of the first and second authoring users 18 and 19, the receiving user 22 may then be made aware of whether he or she (i.e., the receiving user 22) is misunderstanding the intent, tone, and/or meaning of the particular item 21 when viewing the particular item 21 (e.g., the receiving user 22 becoming mistakenly distressed by the particular item 21 because the recipient misunderstood the tone of the humorous story). That is, and as will be further described, by comparing the inferred mental state of the first authoring user 18 in connection with the creation of the particular item 21 and/or the inferred mental state of the second authoring user 19 with a mental state of the receiving user 22 during or proximate to the presentation to the receiving user 22 of the particular item 21, a determination may be made as to whether the receiving user 22 is properly understanding the meaning and tone of the particular item 21.

The following example is provided that describes how inference data, such as the first inference data that indicates the inferred mental state of the first authoring user 18 in connection with a particular item 21 may be used by a recipient of the electronic document 20, such as receiving user 22, in accordance with some implementations. As described above, the receiving user 22 may be facilitated in understanding the proper intent and meaning of a particular item 21 in the electronic document 20 by being provided with the first inference data that is indicative of the inferred mental state of the first authoring user 18 in connection with an "action" (e.g., creation) performed, at least in part, by the first authoring user 18 and executed with respect to the particular item 21. As will be further described, an action executed in connection with the particular item 21 may be in reference to any one of a number of acts that can be executed, at least in part, by the first authoring user 18 including, for example, creating, modifying, deleting, relocating, extracting, forwarding, storing, activating or deactivating, tagging, associating, categorizing, substituting, inserting, and so forth in connection with the particular item 21. Note that unless indicated otherwise the term "particular item" as used herein merely refers to a specific item from, for example, a plurality of items that may be included in an electronic document 20 (see, for example, FIG. 2n).

After receiving the first inference data from the authoring device 10, a comparison of the inferred mental state of the first authoring user 18 (e.g., as derived from the first inference data) in connection with the particular item 21 and the inferred mental state of the receiving user 22, during or proximate to the presentation of the particular item 21 to the receiving user 22, may be made at the receiving network device 12. Note that the inferred mental state of the receiving user 22 with respect to the presentation of the particular item 21 may be determined based, at least in part, on observations of one or more physical characteristics of the receiving user 22 made during or proximate to the presentation of the particular item 21. The comparison of the inferred mental states of the first authoring user 18 and the receiving user 22 in connection with the particular item 21 may be made at the receiving network device 12 in order to determine the extent of congruity between the mental states of the first authoring user 18 and the receiving user 22 with respect to the particular item 21. Alternatively, such comparison and congruity determination may be made at a third party network device 14. By making such comparisons, the receiving user 22 may be made aware as to whether the receiving user 22 properly understood the intent and meaning of the particular item 21 when the particular item 21 was presented to the receiving user 22.

For instance, in some cases if it is determined that there is very little congruence between the inferred mental state of the first authoring user 18 and the inferred mental state of the receiving user 22 in connection with the particular item 21 then that may indicate that the receiving user 22 has misunderstood the intent and/or meaning of the particular item 21 when the particular item was presented to the receiving user 22. Alternatively, a determination of very little congruence between the inferred mental state of the first authoring user 18 and inferred mental state of the receiving user 22 may, in some cases, actually indicate that the receiver user 22 did indeed understand the intent and meaning of the particular item 21 when the particular item 21 was presented to the receiving user 22. For example, if the first authoring user 18 was in a sarcastic state of mind when creating the particular item 21 with the intent to anger the receiving user 22 then there may be very little congruence between the inferred mental state of the first authoring user 18 and the inferred mental state of the receiving user 22 if the receiving user 22 properly understood the intent and meaning of the particular item 21.

In order to facilitate the receiving network device 12 (and/or the third party network device 14) to correctly process and/or interpret the first inference data provided by the authoring device 10, the authoring device 10 may acquire a first source identity data providing one or more identities of one or more sources that may have been the basis for the first inference data. For example, the authoring device 10 acquiring a first identity data providing one or more identities of the one or more sensors 48 that may have been used to sense the physical characteristics of the first authoring user 18.

The acquired first source identity data may then be associated with the particular item 21 in order to make the first source identity data accessible or available to the receiving network device 12 (and/or the third party network device 14). In various implementations, by making available the first source identity data, the receiving network device 12 (and/or the third party network device 14) may be facilitated in properly interpreting the first inference data as provided by the authoring device 10.

Returning to FIG. 1, in some implementations, the authoring device 10 may communicate with the receiving network device 12, and in some instances, may alternatively or additionally communicate with a third party network device 14, via a wireless and/or wired network[s] 16. As described earlier, the authoring device 10 in various implementations may be any type of computing and/or communication device such as a server (e.g., network server), a personal computer (PC), a laptop computer, a personal digital assistant (PDA), a cellular telephone, a blackberry, and so forth. In some implementations, the authoring device 10 may b a workstation and may interface or communicate directly (e.g., without going through a remote network device 50/51) with both the first authoring user 18 and the second authoring user 19. In some alternative implementations, however, in which the authoring device 10 is, for example, a network server, the authoring device 10 may communicate with the first authoring user 18 and/or the second authoring user 19 through one or more remote network devices 50/51 via, for example, the wireless and/or wired network[s] 16.

As briefly indicated earlier, in some implementations, the authoring device 10 may be particularly configured to present data that may indicate the extent of congruity between the inferred mental states of authoring users (e.g., first authoring user 18 and second authoring user 19) in connection with a particular item 21 of an electronic document 20. In some implementations, such "congruence" data may be presented to one or more of the authoring users (e.g., first authoring user 18 and/or second authoring user 19) prior to the transmission of the inference data indicating the inferred mental states of the first authoring user 18 and/or the second authoring user 19 in connection with the particular item 21.

For example, in the above described example in which the first authoring user 18 creates the particular item 21 and the second authoring user 19 modifies the particular item 21, the authoring device 10 may compare the inferred mental state of the first authoring user 18 in connection with the creation of the particular item 21 with the inferred mental state of the second authoring user 19 in connection with the modification of the particular item 21. Based on the comparison, the authoring device 10 may present to the first authoring user 18 and/or the second authoring user 19 congruence data that indicates the extent of congruity between the inferred mental state of the first authoring user 18 and the inferred mental state of the second authoring user 19 in connection with the particular item 21. In doing so, the first authoring user 18 and/or the second authoring user 19 may be made aware of whether their inferred mental states match or are similar. For these implementations, the authoring device 10 may be further designed to provide to the one or more of the authoring users (e.g., first authoring user 18 and/or second authoring user 19), following the presentation of the congruence data, an option not to transmit the data indicating the inferred mental states of the authoring users or an option to transmit data that indicates alternative mental states for the authoring users.

In the same or different implementations, such congruence data may also be presented to a recipient (e.g., receiving user 22) of the electronic document 20. By doing so, the recipient may, for example, better understand the intent and meaning of the particular item 21.

Figure 2A:
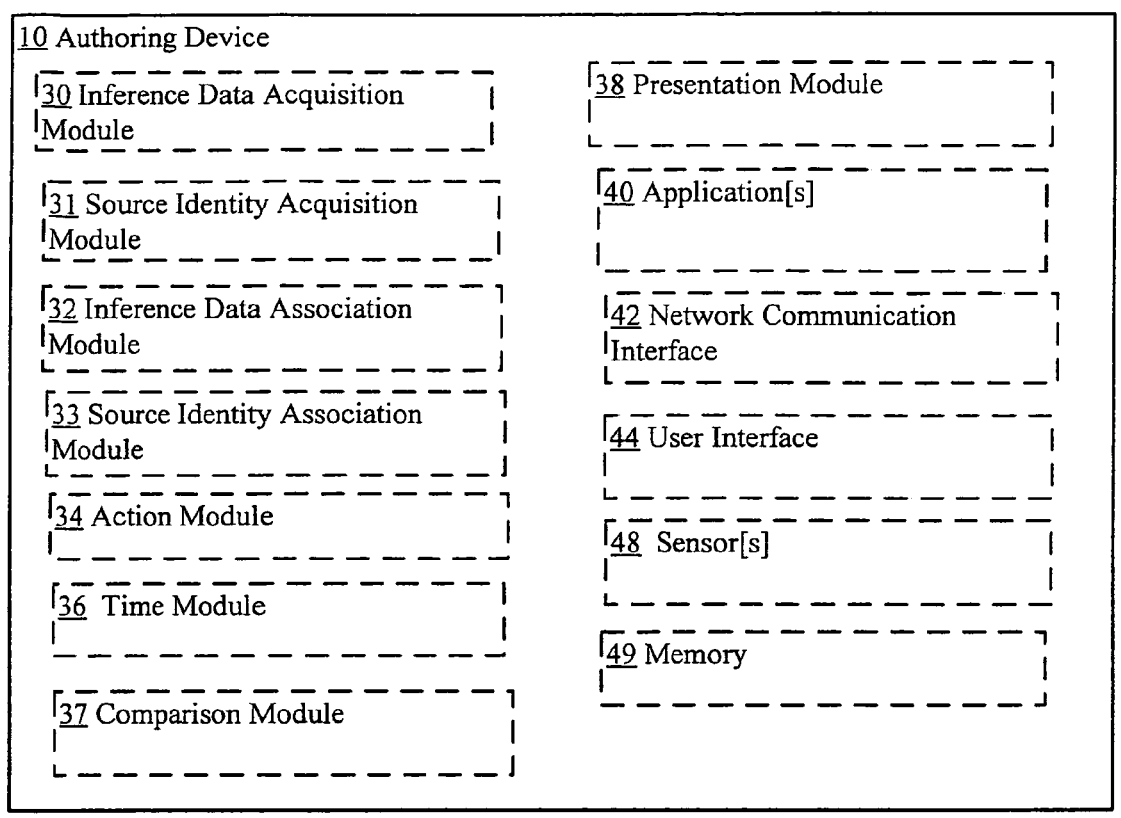
FIG. 2a shows another perspective of the authoring device 10 of FIG. 1.

Turning to FIG. 2a illustrating various implementations of the authoring device 10 of FIG. 1. The authoring device 10 may include various components including, for example, an inference data acquisition module 30, a source identity acquisition module 31, an inference data association module 32, a source identity association module 33, an action module 34, a time module 36, a comparison module 37, a presentation module 38, one or more applications 40, network communication interface 42, user interface 44, one or more sensors 48, and/or memory 49. In various alternative implementations, one or more of these components may be absent while in other implementations other components that are not depicted may be included in the authoring device 10.

In various embodiments, the inference data acquisition module 30 may be configured to acquire inference data that may indicate the inferred mental states of multiple authoring users in connection with at least a particular item 21 of an electronic document 20. For example, the inference data acquisition module 30 may be designed to acquire a first inference data that may indicate an inferred mental state of the first authoring user 18 and a second inference data that may indicate an inferred mental state of the second authoring user 19 in connection with the particular item 21. Unless indicated otherwise, the term "acquire" or "acquiring," as used herein, may be broadly construed and may be in reference to the determination, computation, reception, and/or other methods of obtaining, for example, inference data.

As briefly described above, the authoring device 10 may include, among other things, a source identity acquisition module 31 (e.g., for acquiring source identity data including, for example, a first source identity data associated with the first inference data and a second source identity data associated with the second inference data that provides one or more identities of one or more sources that are the bases, at least in part, for the first and second inference data acquired by the inference data acquisition module 30), an inference data association module 32 (e.g., for associating the first and second inference data with the particular item 21), a source identity association module 33 (e.g., for associating the first and second source identity data with the particular item 21), an action module 34 (e.g., for facilitating the authoring users in executing one or more actions in connection with the particular item 21), a time module 36 (e.g., for providing time stamps and/or time windows in connection with actions to be performed in connection with the particular item 21), a comparison module 37 (e.g., for comparing the inferred mental states of authoring users), a presentation module 38 (e.g., for presenting data indicative of extent of congruity between inferred mental states of authoring users in connection with the particular item 21), one or more of applications 40 (e.g., word processing, email, instant messaging (IM), audio, and/or video applications), a network communication interface 42, a user interface 44, one or more sensors 48 (e.g., for sensing physical characteristics of the first authoring user 18 and/or the second authoring user 19), and/or memory 49 (e.g., which may be one or more memories for storing, for example, the identities of one or more sources that provide a basis for the inference data acquired by the inference data acquisition module 30).

Figure 2B:
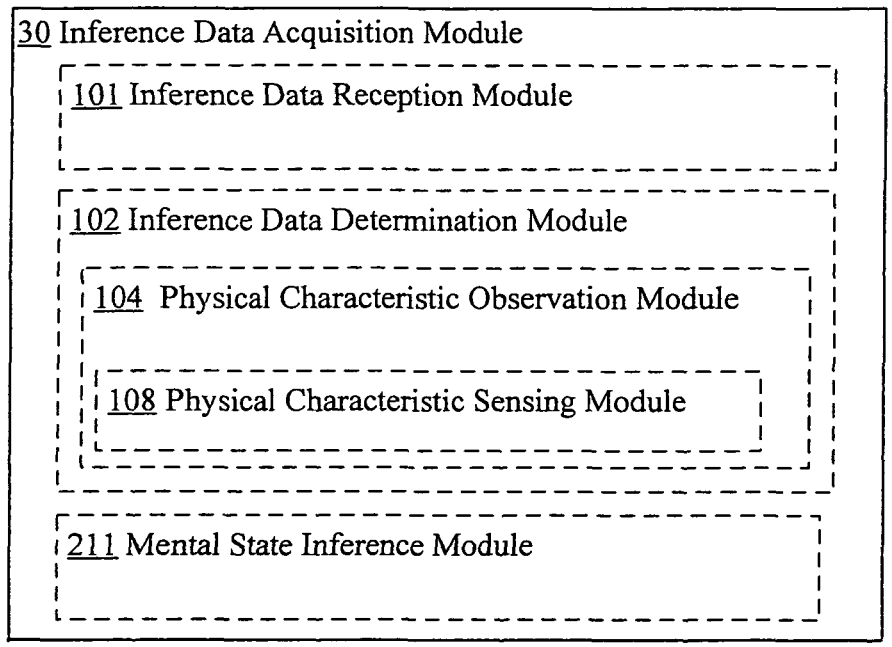

Referring now to FIG. 2b showing particular implementations of the inference data acquisition module 30 of the authoring device 10 of FIG. 1. As illustrated, the inference data acquisition module 30 may include one or more submodules including, for example, an inference data reception module 101 an inference data determination module 102, and/or a mental state inference module 211. In some implementations, the inference data determination module 102 may further include a physical characteristic observation module 104, which may further include a physical characteristic sensing module 108.

In brief, the inference data reception module 101 may be specifically configured to, among other things, receive inference data indicative of inferred mental state or states of one or more authoring users (e.g., first authoring user 18, second authoring user 19, and so forth) in connection with a particular item 21 of an electronic document 20. In some implementations, such inference data may be received from one or more remote network devices 50/51. The inference data reception module may also be employed in order to receive other types of information such as time stamps or indications of actions executed, at least in part, by authoring users (e.g., first authoring user 18 and second authoring user 19). In contrast, the inference data determination module 102 may be configured to derive or determine (as opposed to receiving) the inference data indicative of inferred mental states of multiple authoring users in connection with the particular item 21 of the electronic document 20. In various implementations, such a determination may be based, at least in part, on the observed physical characteristics of the multiple authoring users (e.g., first authoring user 18, second authoring user 19, and so forth).

The physical characteristic observation module 104 that may be included in the inference data determination module 102 may be configured to, for example, observe the physical characteristics of authoring users (e.g., first authoring user 18, second authoring user 19, and so forth) during or proximate to actions executed in connection with the particular item 21 and performed, at least in part, by the authoring users. In some implementations, the observance of the physical characteristics of the authoring users may be through one or more time windows that correspond to one or more time windows through which the actions that are executed in connection with the particular item 21 are performed, at least in part, by the authoring users.

Note that in various alternative implementations, the observance of the physical characteristics of the authoring users (e.g., first authoring user 18 and second authoring user 19) may be a continuous or semi continuous process in which case only data obtained through the one or more time windows may be used in order to, for example, derive the inference data (e.g., the first inference data and the second inference data). As will be further described, the actions to be executed may be any type of acts that may be executed by the authoring users in direct connection with the particular item 21. Examples of such acts may include, for example, creating, modifying, deleting, relocating, extracting, forwarding, storing, activating or deactivating, tagging, associating, categorizing, substituting, inserting, selecting, and so forth, in connection with the particular item 21. In some implementations, the authoring users may employ the action module 34 in order to execute such actions.

Alternatively, the actions to be executed may be other types of acts that may be performed, at least in part, by the authoring users (e.g., first authoring user 18, second authoring user 19, and so forth) and that may be indirectly connected to the particular item 21. For example, such indirect acts may include, for example, the movement of a user interface (UI) pointing device with respect to the particular item 21 being displayed on a user display, the specific movements of the authoring user's eyes (which may be detected using a gaze tracking device 151) during or proximate to the presentation of the particular item 21 through a user display, and the specific postures, gestures, and/or sounds (e.g., as detected though one or more sensors 48) made by the authoring user in connection with the presentation to the authoring user of the particular item 21 through the user interface 44.

The physical characteristic sensing module 108 of the physical characteristic observation module 104 may be configured to sense one or more physical characteristics of an authoring user (e.g., the first authoring user 18 or the second authoring user 19) during or proximate to an action executed in direct or indirect connection with the particular item 21 and performed, at least in part, by the authoring user. Various physical characteristics of the first authoring user 18 may be sensed using various sensors 48 in various alternative embodiments. For example, in some embodiments, the physical characteristic sensing module 108 employing one or more sensors 48 may sense, during or proximate to an action executed in connection with the particular item 21 and performed, at least in party, by an authoring user (e.g., first authoring user 18 or second authoring user 19), at least one of cerebral, cardiopulmonary, and/or systemic physiological characteristic associated with the authoring user.

For instance, in some implementations, the physical characteristic sensing module 108 may be configured to sense, at least during or proximate to an action executed in connection with the particular item 21 and performed, at least in part, by an authoring user (e.g., the first authoring user 18 or the second authoring user 19), at least one characteristic connected with electrical activity of a brain associated with the authoring user. In the same or different implementations, the physical characteristic sensing module 108 may be configured to sense, at least during or proximate to the action executed in connection with the particular item 21 and performed, at least in part, by the authoring user, at least one of blood oxygen or blood volume changes of a brain associated with the authoring user. In the same or different implementations, other types of physical characteristics of the authoring user may also be sensed by the physical characteristic sensing module 108.

In various implementations, the inference data acquisition module 30 may include a mental state inference module 211. In brief, the mental state inference module 211 may be configured to infer mental states of authoring users (e.g., first authoring user 18, second authoring user 19, and so forth) in connection with the particular item 21 based, at least in part, on physical characteristics of the authoring users observed via, for example, the sensors 48 (or via the sensors 48" of remote network devices 50/51—see FIG. 2*t*). In some implementations, this may mean processing the inference data that may have been collected by the inference data reception module 101 or by the inference data determination module 102.

In some implementations, the mental state inference module 211, based on one or more observed physical characteristics of an authoring user (e.g., the first authoring user 18 or the second authoring user 19), may be designed to infer a mental state for the authoring user that indicates that the authoring user was or is in at least one of state of anger, a state of distress, and/or a state of pain. In the same or different implementations, the mental state inference module 211 may be designed to infer, based on the one or more observed physical characteristics of the authoring user, a mental state for the authoring user that indicates that the authoring user was or is in at least one of a state of frustration, a state of approval or disapproval, a state of trust, a state of fear, a state of happiness, a state of surprise, a state of inattention, a state of arousal, a state of impatience, a state of confusion, a state of distraction, a state of overall mental activity, a state of alertness, and/or a state of acuity.

In various implementations, the authoring device 10 may include a source identity acquisition module 31 that may be configured to acquire source identity data that provides one or more identities of one or more sources that are the basis for the inference data (e.g., the first inference data associated with the first authoring user 18 and the second inference data associated with the second authoring user 19 in connection with the particular item 21) collected by the inference data acquisition module 30. As illustrated in FIG. 2*g*, the source identity acquisition module 31 may include one or more sub-modules including an authoring user identity (ID) acquisition module 201, an inference technique or model identity (ID) acquisition module 202, a database or library identity (ID) acquisition module 203, and/or a sensor identity (ID) acquisition module 204. These modules may perform one or more acquisition operations to acquire one or more identities of one or more sources that may be the basis for the inference data acquired by the inference data acquisition module 30.

For example, the authoring user ID acquisition module 201 may be configured to acquire the identities of the authoring users (e.g., first authoring user 18, second authoring user 19, and so forth) who may be the bases for the inference data acquired by the inference data acquisition module 30. The inference technique or model ID acquisition module 202, in contrast, may be configured to acquire the one or more identities of the one or more inference techniques and/or one or more inference models that may have been used to derive inferred mental states of the authoring users based on the sensed physical characteristics of the authoring users. Meanwhile the database or library ID acquisition module 203 may be configured to acquire the one or more identities of the one or more databases and/or one or more libraries (e.g., which, as will be further explained below, may store physical characteristic patterns) that may have been used by, for example, the mental state inference module 211 in order to determine the inferred mental states of authoring users (e.g., first authoring user 18, second authoring user 19, and so forth). Finally, the sensor identity ID acquisition module 204 may be configured to acquire the one or more identities of one or more sensors 48 used to sense physical characteristics of the authoring users (e.g., first authoring user 18, second authoring user 19, and so forth). Note that the above-mentioned inference techniques, inference models, databases, and libraries will be described in greater detail below.

In various implementations, the source identity acquisition module 31 and its sub-modules may obtain the one or more identities of the one or more sources from various locations. For example, in some implementations, the identities may be obtained from memory 49, while in other implementations the identities may be obtained from the sources themselves.

Referring back to FIG. 2a, the authoring device 10 may include an inference data association module 32 that may be configured to associate inference data (e.g., as acquired by the inference data acquisition module 30) indicative of the inferred mental states of authoring users (e.g., first authoring user 18, second authoring user 19, and so forth) with respect to a particular item 21 of an electronic document 20. Different approaches for associating the inference data with the particular item 21 may be employed in various alternative implementations.

For example, in some implementations, in order to associate the inference data with the particular item 21 the inference data may be inserted into the particular item 21 itself or at a particular location or locations (e.g., at a location proximate to the location where the particular item 21 is located) of the electronic document 20. In alternative embodiments, however, the inference data may be inserted anywhere in the electronic document 20, and association information (e.g., in the form of a link or name) that identifies the inference data may be provided or included with the particular item 21. In still other embodiments, the inference data may be inserted anywhere in the electronic document 20, and information (e.g., in the form of a link or name) that identifies the particular item 21 may be provided to the inference data.

In still other embodiments, the inference data may be inserted into another electronic message (e.g., a different electronic message from electronic document 20 that includes the particular item 21) and the inference data and/or the particular item 21 may be provided with information that links or associates the inference data with the particular item 21. In yet other implementations, the inference data may be stored or placed in, for example, a network server and the particular item 21 may be provided with a network link such as a hyperlink to the inference data. Other approaches may be employed in various other alterative embodiments for associating the inference data with the particular item 21.

In some implementations, and as illustrated in FIG. 2f, the inference data association module 32 may include an inference data inclusion module 110 for inserting various data including inference data (e.g., as acquired by the inference data acquisition module 30) into the electronic document 20. For example, in some implementations, the inference data inclusion module 110 may be configured to include into the electronic document 20 one or more time stamps associated with the inference data included in the electronic document 20. In some implementations, the inference data inclusion module 110 may be configured to include into the electronic document 20, one or more indications of one or more actions performed by one or more authoring users (e.g., first authoring user 18, second authoring user 19, and/or other authoring users) in connection with the particular item 21. For instance the inference data inclusion module 110 including into the electronic document 20, an indication of the creation, modification, or deletion, of the particular item 21 as performed, at least in part, by the first authoring user 18 or the second authoring user 19. The inference data inclusion module 110 may also be further designed to include into the electronic document 20 various other types of data in various alternative implementations as will be further described herein.

In various implementations, the authoring device 10 may include a source identity association module 33 for associating source identity data (e.g., as acquired by the source identity acquisition module 31) with the particular item 21. As in the case of the inference data association module 32 described above, the source identity association module 33 may similarly employ various techniques in various alternative implementations for associating source identity data with the particular item 21 including, for example, inserting the source identity data into the particular item 21 or inserting the source identity data elsewhere in the electronic document 20. As illustrated in FIG. 2h, the source identity association module 33 may include, in various implementations, a source identity inclusion module 111 for including into the electronic document 20 the source identity data (e.g., source identity data providing one or more identities of one or more sources that may be the basis for the inference data acquired by the inference data acquisition module 30) as acquired by the source identity acquisition module 31.

Figure 2C:
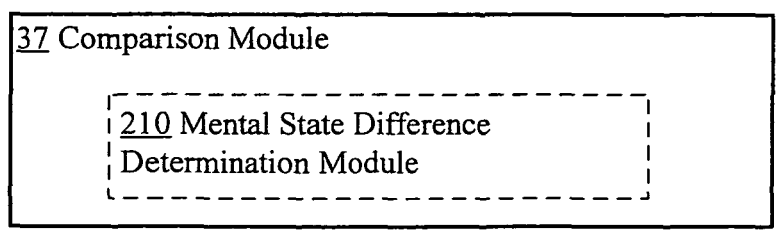
Figure 2H:
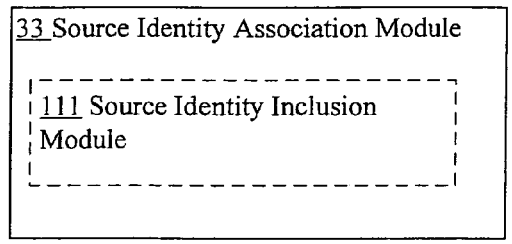

The authoring device 10, as illustrated in FIG. 2a, may also include an action module 34, which may be employed for executing one or more actions in connection with the particular item 21. More particularly, the action module 34 may facilitate authoring users (e.g., first authoring user 18, second authoring user 19, and so forth) in executing various actions with respect to one or more items (e.g., particular item 21, another particular item 22, and so forth of an electronic document 20 as illustrated in FIG. 2n) of an electronic document 20. In some implementations, the action module 34 may be embodied, at least in part, by one or more applications such as a word processing application, a text messaging application, an email application, an instant messaging (IM) application, an audio application, and/or a video application.

Figure 2I:
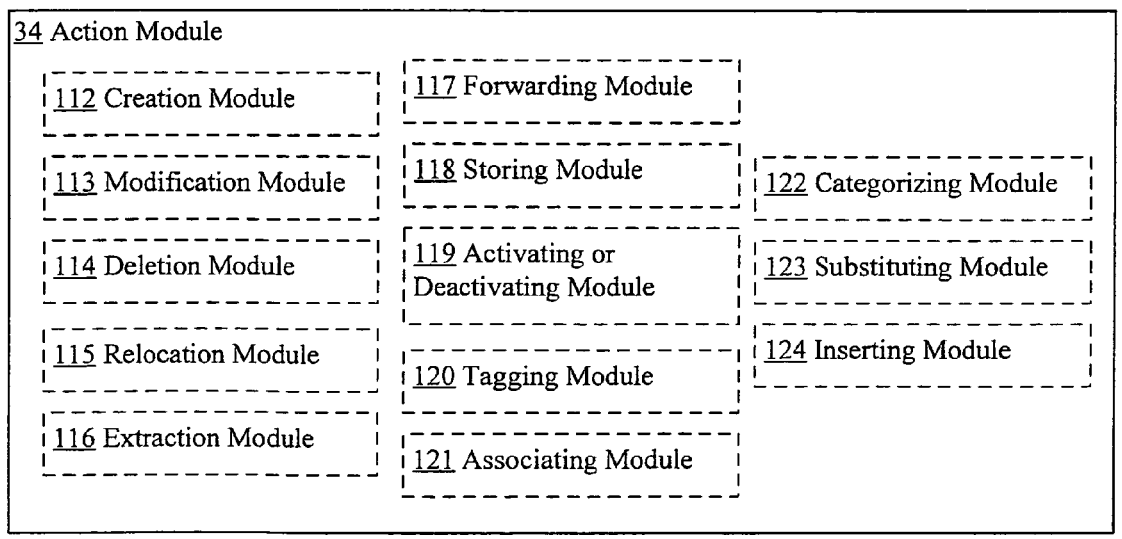

Turning to FIG. 2i illustrating various implementations of the action module 34 of FIG. 2a. As depicted, the action module 34 may include, in various implementations, one or more sub-modules including, for example, a creation module 112, a modification module 113, a deletion module 114, a relocation module 115, an extraction module 116, a forwarding module 117, a storing module 118, an activating or deactivating module 119, a tagging module 120, an associating module 121, a categorizing module 122, a substituting module 123, and/or an inserting module 124. In various implementations, these sub-modules may be used by authoring users (e.g., first authoring user 18, second authoring user 19, and so forth) in order to execute various actions (e.g., creating, modifying, deleting, relocating, extracting, forwarding, storing, activating or deactivating, tagging, associating, categorizing, substituting, and/or inserting) with respect to one or more items of an electronic document 20.

In some embodiments, the action module 34 may provide indications of actions (e.g., creating, modifying, deleting, relocating, extracting, and so forth) that have been executed by the authoring users using the action module 34. Such indications may be in the form of, for example, identifiers (e.g., names) or symbolic representations of the actions performed.

In various implementations, the creation module 112 of the action module 34 may be employed in order to, among other things, create a particular item 21. The modification module 113 may be employed in order to modify the particular item 21. Modification in this context may refer to a number of functions including, for example, changing the format of the particular item 21 (e.g., highlighting or bolding a word), adding or subtracting components into or from the particular item 21, and so forth. The deletion module 114 may be employed to, among other things, delete the particular item 21 from the electronic document 20. The relocation module 115 may be used in order to relocate the particular item 21 from, for example, a first location in the electronic document 20 to a second location in the electronic document 20.

The extraction module 116 may be used in order to extract the particular item 21 from the electronic document 20. In some implementations, extraction of the particular item 21 from the electronic document 20 may involve merely copying of the particular item 21 from the electronic document 20. The forwarding module 117 may be employed in order to, among other things, forward or send the particular item 21 to one or more recipients. The storing module 118 may be used in order to store or save the particular item 21. For instance, in some implementations, the storing module 118 may be used in order to store the particular item 21 into memory 49. The activating or deactivating module 119 may be employed in order to, among other things, activate or deactivate the particular item 21. For example, if the electronic document 20 is an email message and the particular item 21 is some sort of video/animation image that can be activated or deactivated, then the activating or deactivating module 119 may be used in order to activate or deactivate the video/animation image.

The tagging module 120 may be employed in order to, among other things, tag or attach data or information to the particular item 21. For example, in some implementation, the tagging module 120 may be used in order to add some sort of indicator to the particular item 21 to, for example, flag the particular item 21. In contrast, the associating module 121 may be employed in order to associate the particular item 21 with, for example, another item. For instance, in some implementations, the associating module 121 may be used in order to associate the particular item 21 to another item by providing to the particular item 21 an identity or link (e.g., hyperlink) to the another item that may or may not be included in the electronic document 20.

The categorizing module 122 may be employed in order to categorize the particular item 21. For instance, the categorizing module 122 may be used to in order to associate the particular item 21 to a group of items that may or may not be included in the electronic document 20. Categorizing using the categorizing module 122 may also include labeling or tagging, for example, the particular item 21 in order to identify the particular item 21 as belonging to a particular group or class. The substituting module 123 may be employed in order to substitute or replace the particular item 21 in the electronic document 20. And finally, the inserting module 124 may be employed in order to insert the particular item 21 into the electronic document 20

Figure 2J:
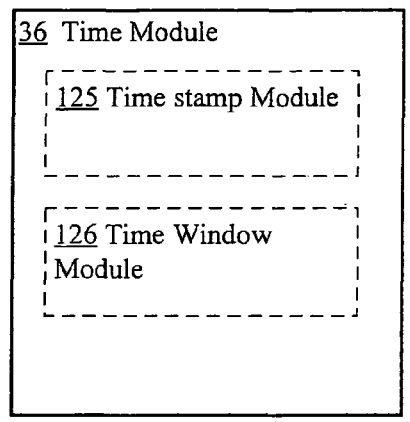

Referring now to FIG. 2j showing particular implementations of the time module 36 of FIG. 2a. In brief, the time module 36 may be configured to provide various time elements that may be used in order to acquire and associate inference data indicative of the inferred mental states of authoring users (e.g., first authoring user 18, second authoring user 19, and so forth) in connection with actions that may be performed, at least in part, by the authoring users with respect to the particular item 21. As depicted, the time module 36 may include one or more sub-modules including, for example, a time stamp module 125 (e.g., for providing one or more time stamps for the observations of physical characteristics of the first authoring user 18 and the second authoring user 19) and/or a time window module 126 (e.g., for providing one or more time windows through which physical characteristics of the first authoring user 18 and the second authoring user 19 may be observed using, for example, one or more sensors 48). The functional roles of these sub-modules will be described in greater detail below in the context of the operations and processes to be described herein.

FIG. 2c shows particular implementations of the comparison module 37 of FIG. 2a. As depicted, the comparison module 37 may include a mental state difference determination module 210. As will be further described herein, the mental state difference determination module 210 may be designed to determine the extent of difference between inferred mental states of multiple authoring users (e.g., first authoring user 18 and second authoring user 19) in connection with a particular item 21 of an electronic document 20. Different types of data may be processed by the mental state difference determination module 210 in various alternative implementations in order to determine the extent of difference between the inferred mental states of authoring users. For example, in some implementations, this may mean, for example, comparing a first inference data of the first authoring user 18 collected by the inference data reception module 101 with a second inference data of the second authoring user 19 collected by the inference data reception module 101. Alternatively, the mental state difference determination module 210 may compare a first inference data of the first authoring user 18 collected by the inference data determination module 102 with a second inference data of the second authoring user 19 collected by the inference data determination module 102. In still other implementations, the mental state difference determination module 210 may compare the inferred mental state of the first authoring user 18, as obtained by the mental state inference module 211, with the inferred mental state of the second authoring user 19, as obtained by the mental state inference module 211.

FIG. 2d shows various implementations of the presentation module 38 depicted in FIG. 2a. As briefly described earlier, the presentation module 38 may be configured to present data indicative of extent of congruity between inferred mental states of authoring users (or simply "congruence" data) in connection with a particular item 21 of an electronic document 20. Such congruence data, in various implementations, may be presented to one or more of the authoring users (e.g., the first authoring user 18 and/or the second authoring user 19), a receiving user 22, and/or a third party participant. In various implementations, the presentation module 38 may include a transmission module 212 and/or a display module 213. In particular implementations, the transmission module 212 may be designed to transmit (e.g., via a network communication interface 42) the congruence data to one or more of the authoring users, a receiving user 22, and/or a third party participant. In contrast, the display module 213 may be designed to display (e.g., via a user interface 44) the congruence data to one or more of the authoring users (e.g., the first authoring user 18 and/or the second authoring user 19).

Figure 2K:
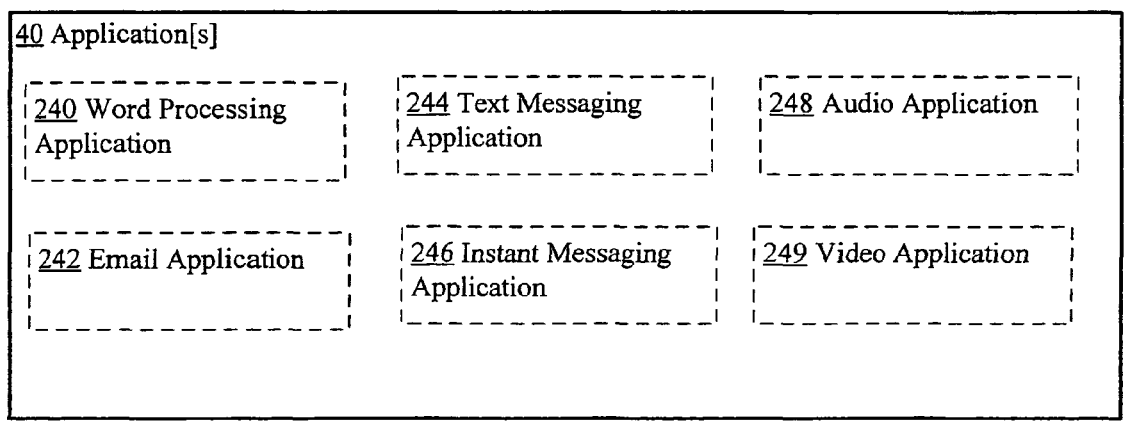

FIG. 2k shows particular implementations of the one or more applications 40 depicted in FIG. 2a. As illustrated, the one or more applications 40 may include a word processing application 240, an email application 242, a text messaging application 244, an instant messaging application 246, an audio application 248, and/or a video application 249.

Figure 2L:
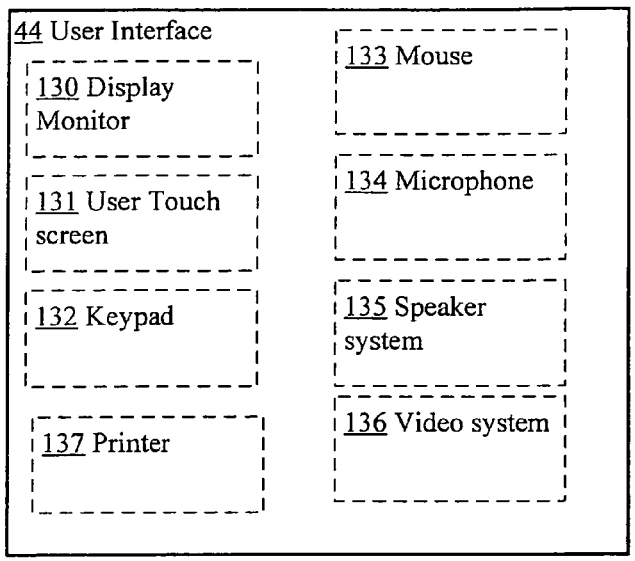

FIG. 2l shows particular implementations of the user interface 44 of the authoring device 10 of FIG. 2a. As illustrated, the user interface 44, which may actually be one or more user interfaces, may include one or more of a display monitor 130, a user touch screen 131, a keypad 132, a mouse 133, a microphone 134, a speaker system 135, a video system 136, and/or a printer 137.

In some implementations, the authoring device 10 as illustrated in FIG. 2a may include a memory 49, which may actually be comprised of one or more volatile and/or nonvolatile memories (e.g., SRAM, DRAM, flash memory, hard or disk drives, and so forth). The memory 49 may be employed in order to store one or more identities of one or more sources that are the basis for inference data (e.g., inference data indicative of the inferred mental state of the first authoring user 18 and/or the second authoring user 19 in connection with the particular item 21) acquired by, for example, the inference data acquisition module 30. In some implementations, the memory 49 may also be used in order to store a database or library of physical characteristic patterns used to derive the inferred mental states of the authoring users (e.g., the first authoring user 18, the second authoring user 19, and so forth). Other relevant information may also be stored in the memory 49 in various alternative embodiments.

Figure 2M:
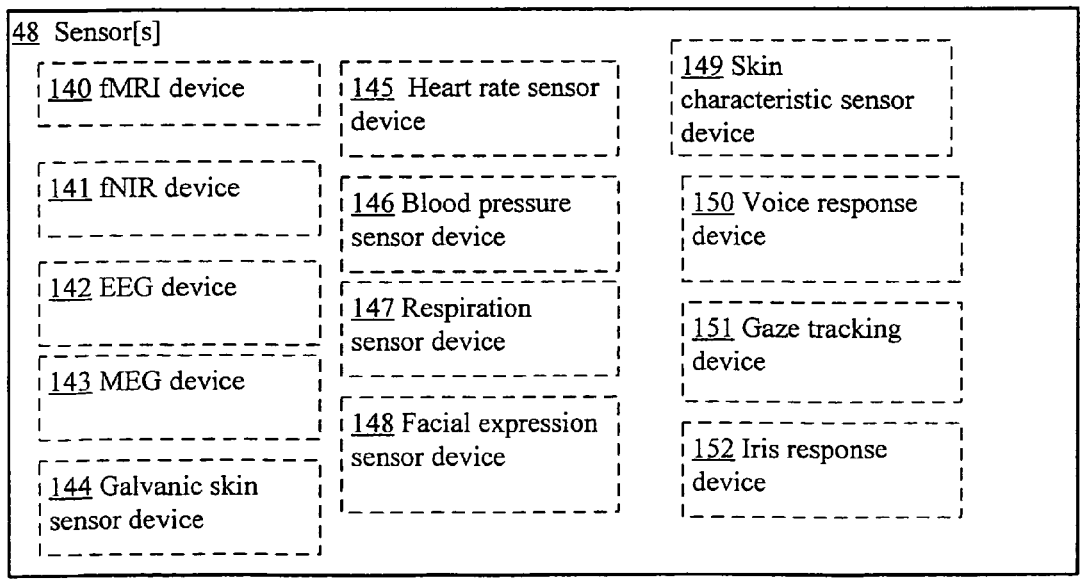
Figure 2N:
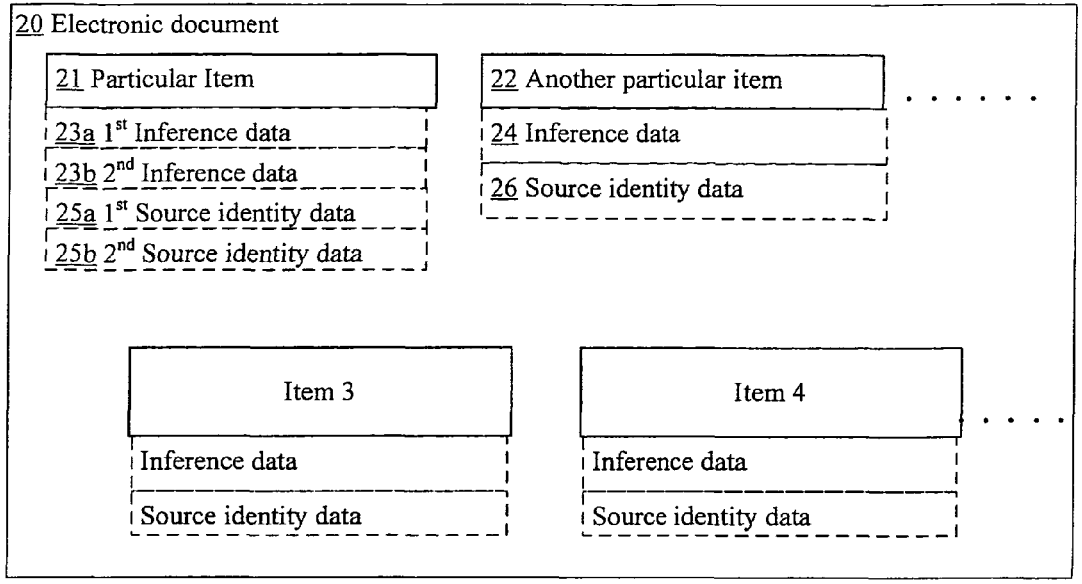
FIG. 2n shows another perspective of the electronic document 20 of FIG. 1.

Turning now to FIG. 2m showing particular implementations of the one or more sensors 48 of FIG. 2a. The one or more sensors 48, which may be one or more integrated and/or external sensors of the authoring device 10, may be employed in order to sense one or more physical characteristics of the first authoring user 18 during or proximate to an action performed by the first authoring user 18 in connection with the particular item 21. For example, and as will be further described, in some implementations, the one or more sensors 48 may be designed to sense one or more of cerebral, cardiopulmonary, and/or systemic physiological characteristics of an authoring user (e.g., first authoring user 18 or second authoring user 19) during or proximate to an action executed in connection with the particular item 21 and performed, at least in part, by the authoring user. In various embodiments, the one or more sensors 48 may include a functional magnetic resonance imaging (fMRI) device 140, a functional near-infrared imaging (fNIR) device 141, an electroencephalography (EEG) device 142, a magnetoencephalography (MEG) device 143, a galvanic skin sensor device 144, a heart rate sensor device 145, a blood pressure sensor device 146, a respiration sensor device 147, a facial expression sensor device 148, a skin characteristic sensor device 149, a voice response device 150, a gaze tracking device 151, and/or an iris response device 152.

In some implementations, the one or more sensors 48 may include one or more sensors that are capable of measuring various brain or cerebral characteristics of an authoring user (e.g., a first authoring user 18 or a second authoring user 19) during or proximate to an action performed by the authoring user in connection with the particular item 21. These sensors may include, for example, a functional magnetic resonance imaging (fMRI) device 140, a functional near-infrared imaging (fNIR) device 141, an electroencephalography (EEG) device 142, and/or a magnetoencephalography (MEG) device 143. In some implementations, an fMRI device 140 and/or an fNIR device 141 may be employed in order to measure particular physiological characteristics of the brain of the authoring user including, for example, blood oxygen or blood volume changes of the brain of the authoring user. In the same or different implementations, an EEG device 142 may be used to sense and measure the electrical activities of the brain of an authoring user while an MEG device 143 may be employed in order to sense and measure the magnetic fields produced by electrical activities of the brain of an authoring user.

Other type of devices may also be employed in order to measure the brain or cerebral activities of an authoring user (e.g., a first authoring user 18 or a second authoring user 19) during or proximate to an action performed by the authoring user in connection with the particular item 21. Such devices may include, for example, a positron emission topography device. In various embodiments, the data collected from these sensor devices may be further processed (e.g., by the mental state inference module 211) in order to determine an "inferred" mental state of an authoring user during or proximate to an action performed by the authoring user in connection with the particular item 21.

As will be further described, in still other implementations, other types of sensors such as those that measure other types of physical characteristics (e.g., cardiopulmonary and/or systemic physiological characteristics) may be employed as sensor[s] 48 (e.g., a galvanic skin sensor device 144, a heart rate sensor device 145, a blood pressure sensor device 146, a respiration sensor device 147, a facial expression sensor device 148, a skin characteristic sensor device 149, a voice response device 150, a gaze tracking device 151, and/or an iris response device 152) in order to obtain data that may be used (e.g., by the mental state inference module 211) to determine the inferred mental state or states of an authoring user during or proximate to an action performed by the authoring user in connection with the particular item 21.

As previously indicated, the one or more sensors 48 may be used in order to observe one or more physical characteristics of an authoring user (e.g., the first authoring user 18 or the second authoring user 19) in connection with an action executed in connection with a particular item 21 and performed, at least in part, by the authoring user. For example, the one or more sensors 48 may be used to sense one or more physical characteristics of the authoring user during or proximate to a modification (e.g., action) by the authoring user of the particular item 21. In order to observe the one or more physical characteristics of the authoring user in some implementations this may mean selectively "switching on" or activating the one or more sensors 48 only during or proximate to the modification (e.g., action) of the particular item 21 of the electronic document 20. In contrast, the one or more sensors 48 may be switched off or deactivated during or proximate to other actions that may be performed by the authoring user in connection with other items (e.g., another particular item 22, item 3, item 4, and so forth of the electronic document 20 as illustrated in FIG. 2n) of the electronic document 20.

In alternative implementations, however, the one or more sensors 48 may be continuously operated (e.g., not switched off and on as described above) in order to, for example, continuously sense the physical characteristics of the authoring user (e.g., a first authoring user 18 or a second authoring user 19) in which case only data provided by the one or more sensors 48 during or proximate to the modification of the particular item 21 may be collected or used (e.g., by the mental state inference module 211). Note that the term "proximate" as used herein may refer to, partly during, immediately subsequent, or immediately preceding the action to be taken (e.g., modification) with respect to the particular item 21.

In any event, data obtained from observations made using one or more such sensors 48 may be collected by, for example, the inference data acquisition module 30 in order to obtain inference data that may indicate an inferred mental state of the authoring user (e.g., a first authoring user 18 or a second authoring user 19) during or proximate to an action executed in connection with the particular item 21 and performed, at least in part, by the authoring user. In some embodiments, raw data collected from the one or more sensors 48 may be further processed by a mental state inference module such as the mental state inference module 211 (see FIG. 2b) in order to provide an inferred mental state for the first authoring user 18 in connection with the particular item 21. The above described process for acquiring inference data via the inference data acquisition module 30 and the one or more sensors 48 may be repeated for each authoring user (e.g., first authoring user 18, second authoring user 19, and so forth) executing an action with respect to the particular item 21.

As briefly described earlier, in addition to being associated with or connected to the particular item 21, an inference data (e.g., a first inference data as acquired by the inference data acquisition module 30) may also be associated with a particular action that is performed, at least in part, by a particular authoring user (e.g., a first authoring user 18). Such an action may include, for example, any one or more of creation, modification, deletion, relocation, extraction, forwarding, storing, activating or deactivating, tagging, associating, categorizing, substituting, or inserting of the particular item 21 by the particular authoring user.

FIG. 2n shows particular implementations of the electronic document 20 of FIG. 1. The electronic document 20 may be any type of an electronic file that may be electronically created including a word processing document. In some implementations, the electronic document 20 may be an electronic message that can be electronically communicated including, for example, an email message, a text message, an instant message (IM), an audio message, a video message, and so forth. As illustrated, the electronic document 20 may include multiple items, which are depicted as a particular item 21, another particular item 22, item 3, item 4, and so forth. An "item" may be any part or portion of the electronic document 20. For example, if the electronic document 20 is an email message or a word processing document, an item could be a passage, a sentence, a paragraph, a word, a letter, a number, a symbol (e.g., icon), an image, the format of text (e.g., bold, highlighting, font size, and so forth), In various embodiments, the electronic document 20 may include inference data indicative of inferred mental states of authoring users (e.g., first authoring user 18, second authoring user 19, and so forth) in connection with the particular item 21, which is depicted in FIG. 2n as a first inference data 23a (e.g., that is associated with the first authoring user 18) and a second inference data 23b (e.g., that is associated with the second authoring user 19). The electronic document 20 may also include source identity data providing one or more identities of one or more sources that are, at least in part, the basis for the first inference data 23a and the second inference data 23b. In FIG. 2n, the source identity data is depicted as a first source identity data 25a and a second source identity data 25b. The first source identity data 25a providing one or more identities of the one or more sources that are, at least in part, the basis for the first inference data 23a and the second source identity data 25b providing one or more identities of the one or more sources that are, at least in part, the basis for the second inference data 23b. Note that in some instances, the first source identity data 25a and the second source identity data 25b may identify the same sources since the same sources (e.g., sensors 48 or inference technique) may have been the basis for the first inference data 23a and the second inference data 23b.

In some implementations, the first inference data 23a and the second inference data 23b may only be associated with the particular item 21 without being associated with the other items (e.g., another particular item 22, item 3, item 4, and so forth) of the electronic document 20. For these implementations, each item (e.g., particular item 21, another particular item 22, item 3, item 4, and so forth) in the electronic document 20 may only be associated with a corresponding inference data/source identity data pair. For example, inference data 24 may only be associated with another particular item 22 and may only indicate the inferred mental state or states of one or more authoring users (e.g., first authoring user 18 and/or second authoring user 19) in connection with the another particular item 22. Correspondingly, source identity data 26 may only identify the sources for the inference data 24 associated with another particular item 22.

An inference data/source identity data pair (e.g., first inference data 23a/first source identity data 25a) may be associated with their associated item (e.g., particular item 21) in any number of different ways in various alternative implementations. For instance, in various implementations the particular item 21 may be associated with the first inference data 23a and the first source identity data 25a by locating or placing the first inference data 23a and the first source identity data 25a at specified locations in the electronic document 20. In some implementations, this may mean locating the first inference data 23a and the first source identity data 25a within the particular item 21 or proximate (e.g., nearby) to the location of the particular item 21 in the electronic document 20. Similarly, the other inference data (e.g., inference data 24) and the other source identity data (e.g., source identity data 26) included in the electronic document 20 may also be associated with their corresponding item (e.g., another particular item 22) by locating them at specified locations in the electronic document 20.

In other alternative implementations, an inference data/source identity data pair (e.g., first inference data 23a/first source identity data 25a) may be located anywhere (e.g., randomly) in the electronic document 20 and may be associated with a corresponding item (e.g., particular item 21) by providing to the inference data/source identity data pair (e.g., first inference data 23a/first source identity data 25a) an identifier that identifies the corresponding item (e.g., particular item 21). In other implementations, however, rather than providing an identifier for the corresponding item (e.g., particular item 21) to the inference data/source identity data pair (e.g., first inference data 23a/first source identity data 25a), an identifier or identifiers of the inference data/source identity data pair may be provided to the corresponding item (e.g., particular item 21).

In some alternative implementations, an inference data/source identity data pair may be associated with more than one item. For instance, in some implementations, the first inference data 23a, which may be an inference data indicative of an inferred mental state of the authoring user 18, may be associated to both the particular item 21 and the another particular item 22. Note that although first inference data 23a and the first source identity data 25a are depicted as being located adjacent or in the vicinity of the particular item 21 in the example electronic document 20 of FIG. 2n, in alternative implementations, the first inference data 23a and/or the first source identity data 25a may be located elsewhere in the electronic document 20 as described above. In yet other implementations, the first inference data 23a and/or the first source identity data 25a may be placed in another electronic document such as, an electronic message (not depicted) instead of in the electronic document 20. In some implementations, first inference data 23a and/or the first source identity data 25a may be included in the electronic document 20 in the form of metadata.

Figure 2P:
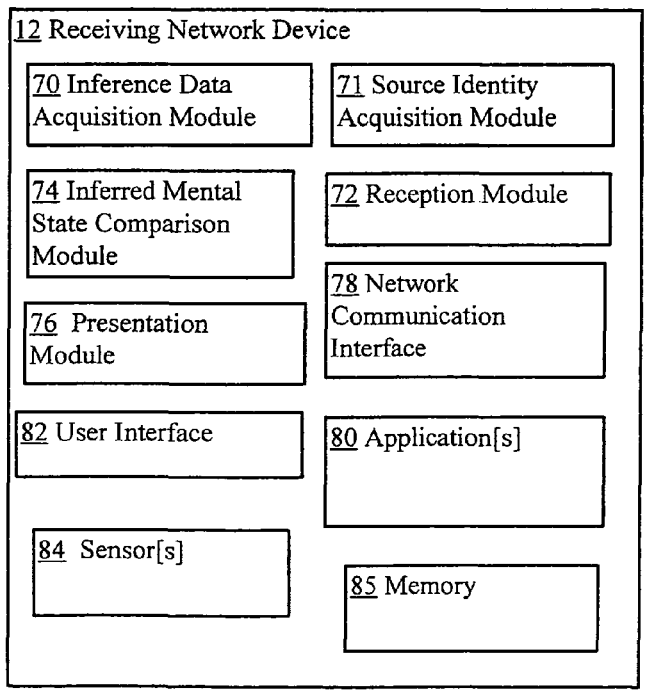
FIG. 2p shows another perspective of the receiving network device 12 of FIG. 1.

Turning now to FIG. 2p, which shows the receiving network device 12 of FIG. 1 in accordance with various implementations. More particularly, FIG. 2p depicts the receiving network device 12 having some of the same components as the authoring device 10 depicted in FIG. 1. For instance, and similar to the authoring device 10, the receiving network device 12 may include an inference data acquisition module 70, source identity acquisition module 71, a network communication interface 78, one or more of email, IM, audio, and/or video applications 80, user interface 82, one or more sensors 84, and memory 85. As will be explained, with certain exceptions, each of these components may include the same sub-components or sub-modules as those included in their counterparts in the authoring device 10. For example, the one or more sensors 84 may include (see FIG. 2q) one or more of an fMRI device 140', an fNIR device 141', an EEG device 142', an MEG device 143', and so forth, while the inference data acquisition module 70 may include (see FIG. 2s) an inference data determination module 102', a mental state inference module 211, a physical characteristic observation module 104', and/or a physical characteristic sensing module 108' similar to their counterparts in the authoring device 10. Further, these components may serve the same or similar functions as those functions performed by their counterparts in the authoring networking device 10.

Figure 2Q:
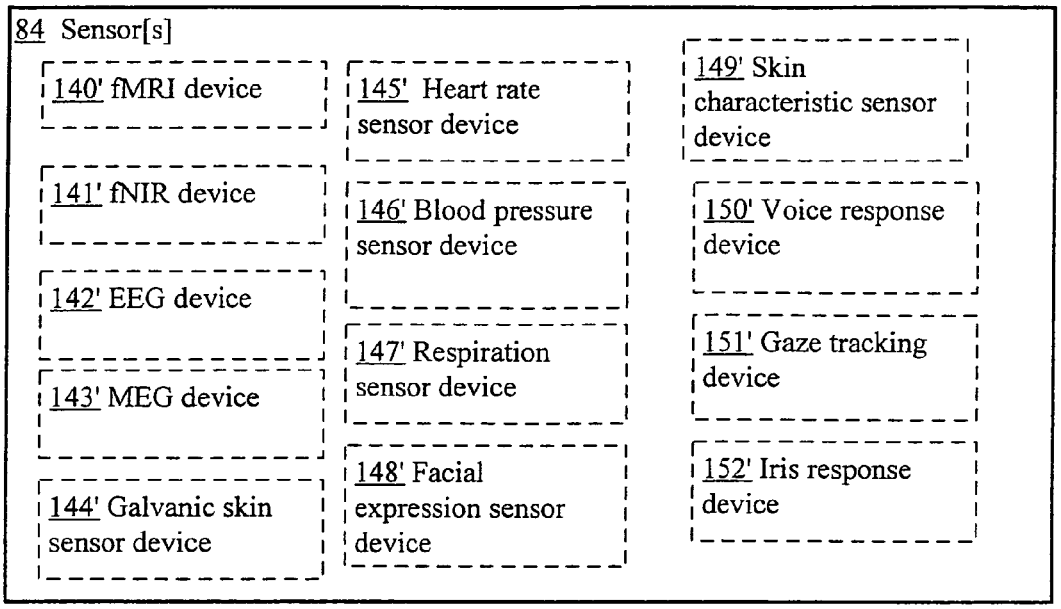
FIG. 2q shows another perspective of the one or more sensors 84 of the receiving network device 12 of FIG. 2p.
Figure 2R:
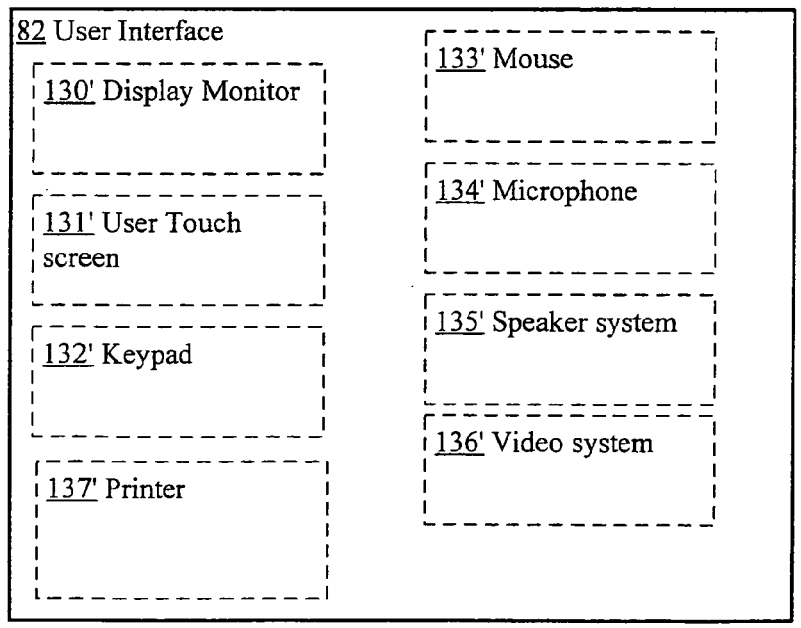
FIG. 2r shows another perspective of the user interface 82 of the receiving network device 12 of FIG. 2p.

Similarly, the user interface 82 of the receiving network device 12 as illustrated in FIG. 2r may include the same type of components as included in the user interface 44 of the authoring device 10. For instance, in various embodiments, user interface 82 may include a display monitor 130', a user touch screen 131', a keypad 132', a mouse 133', a microphone 134', a speaker system 135', a video system 136', and/or a printer 137'.

In addition to the above described components, the receiving network device 12 may also include a reception module 72, an inferred mental state comparison module 74, and a presentation module 76. In brief, the reception module 72 may be configured to receive, among other things, a particular item 21 of an electronic document 20 and inference data (e.g., first inference data and second inference data) indicative of the inferred mental states of authoring users (e.g., first authoring user 18 and second authoring user 19) in connection with the particular item 21 (which may be included in the electronic document 20). The reception module 72 may also be designed to receive source identity data providing one or more identities of one or more sources that may, at least in part, be the basis for the inference data received by the reception module 72, a time stamp associated with the particular item 21, and/or indications of actions performed by the authoring users (e.g., first authoring user 18 and second authoring user 19) in connection with the particular item 21. The inferred mental state comparison module 74 may be configured to, for example, compare the inferred mental state of the receiving user 22 (e.g., in connection with the presentation of the particular item 21 to the receiving user 22) with the inferred mental state of authoring users (e.g., in connection with actions performed with respect to the particular item 21).

Note that the inference data (e.g., inference data 23a and inference data 23b) that is received by the reception module 72 may be in at least one of two different forms. In the first form, the received inference data may be sensor provided data (e.g., "raw" data) of the physical characteristics of authoring users (e.g., first authoring user 18 and second authoring user 19). In some implementations, such data may be further processed by the receiving network device 12 in order to derive the inferred mental states of the authoring users. In the second form, the received inference data may be "processed" data (e.g., as processed by the authoring device 10 via, for example, a mental state inference module) that may directly indicate or identify the inferred mental states of the authoring users in connection with actions performed by the authoring users with respect to the particular item 21.

Referring back to FIG. 2p, the receiving network device 12 may further include an inferred mental state comparison module 74. The inferred mental state comparison module 74 may be employed in order to compare the inferred mental states of one or more authoring users (e.g., first authoring user 18 and/or second authoring user 19) with an inferred mental state of the receiving user 22 in connection with the presentation of the particular item 21 to the receiving user 22. Such a comparison may be used in order to determine the congruence or congruity between the inferred mental states of the one or more authoring users and the inferred mental state of the receiving user 22 in connection with the particular item 21. The results of the comparison and/or the congruence determination may then be presented to the receiving user 22 via the presentation module 76. Note that in various implementations the inferred mental state of the receiving user 22 may be obtained, at least in part, by using one or more sensors 84 in order to observe one or more physical characteristics of the receiving user 22 during or proximate to the presentation of the particular item 21.

In order to derive an inferred mental state of the receiving user 22 during or proximate to the presentation (e.g., display) of the particular item 21 to the receiving user 22, one or more physical characteristics of the receiving user 22 may be observed during or proximate to the presentation of the particular item 21 to the receiving user 22 using the one or more sensors 84. Referring to FIG. 2q which shows the one or more sensors 84 of the receiving network device 12 in accordance with various embodiments. The one or more sensors 84 may include a functional magnetic resonance imaging (fMRI) device 140', a functional near-infrared imaging (fNIR) device 141', an electroencephalography (EEG) device 142', a magnetoencephalography (MEG) device 143', a galvanic skin sensor device 144', a heart rate sensor device 145', a blood pressure sensor device 146', a respiration sensor device 147', a facial expression sensor device 148', a skin characteristic sensor device 149', a voice response device 150', a gaze tracking device 151', and/or an iris response device 152'.

Figure 2S:
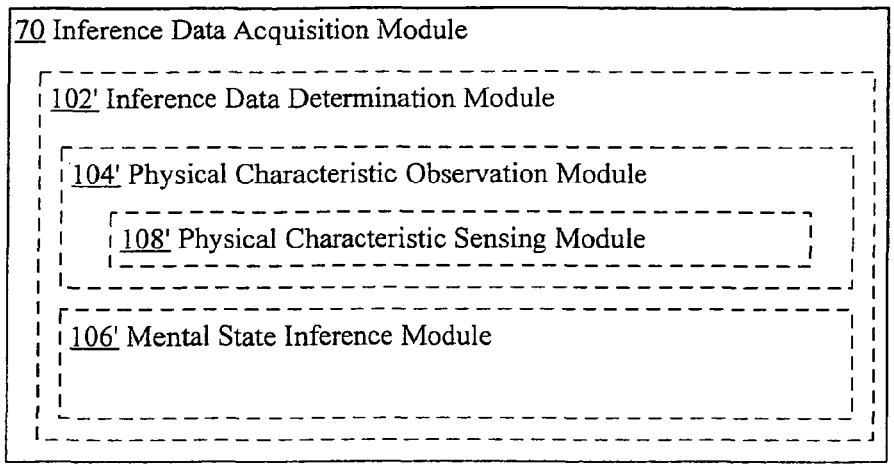
FIG. 2s shows another perspective of the inference data acquisition module 70 of the receiving network device 12 of FIG. 2p.

FIG. 2s illustrates various implementations of the inference data acquisition module 70 of FIG. 2p. As illustrated, the acquisition module 70 may include one or more sub-modules including an inference data determination module 102', a physical characteristic observation module 104', a mental state inference module 106', and/or a physical characteristic sensing module 108', similar to the sub-modules that may be included in the inference data acquisition module 30 of the authoring device 10. These sub-modules may perform functions similar to the functions performed by their counterparts in the inference data acquisition module 30 of the authoring device 10. For example, the inference data determination module 102' may be employed in order to determine inference data indicative of an inferred mental state of the receiving user 22 based on one or more sensed physical characteristics of the receiving user 22. The physical characteristic observation module 104' may be employed in order to observe the one or more physical characteristics of the receiving user 22. The mental state inference module 106' may be employed in order to infer a mental state for the receiving user 22 in connection with the particular item 21. And the physical characteristic sensing module 108' may be employed in order to sense one or more physical characteristics of the receiving user 22 in connection with, for example, the presentation to the receiving user 22 of the particular item 21.

In various embodiments, the mental state inference modules 211 of the authoring device 10 and the receiving network device 12 may employ various techniques or models in order to infer one or more mental states from observed physical characteristics of a subject (e.g., authoring user 18 or receiving user 22). In some implementations, this may mean associating particular physical characteristics or patterns of physical characteristics of a subject that have been sensed via, for example sensors 48/84, to one or more mental states (i.e., inferred mental states).

For example, if the one or more sensors 48 depicted in FIG. 2a include an fMRI device 140, then the fMRI device 140 may be used in order to scan the brain of the subject (e.g., first authoring user 18) during or proximate to an action (e.g., creation, modification, deletion, and so forth) performed by the first authoring user 18 in connection with the particular item 21. As a result of the functional magnetic resonance imaging (fMRI) procedure performed using the fMRI device 140, a profile or a pattern of brain activities (e.g., blood oxygen and/or blood volume changes of the brain) of the first authoring user 18 during or proximate to the execution of the action may be obtained. The determined "brain activity pattern" may then be compared to brain activity patterns (i.e., physical characteristic patterns) that may have been previously recorded and stored in a database or library (each of the stored brain activity patterns being linked with, for example, corresponding mental states). In some implementations, such a database or library may include information relative to the subject (e.g., in this case, the first authoring user 18) including, for example, log of raw sensor data or data of mappings between sensor data and known or inferred mental states that may be used in order to "calibrate" data received from the one or more sensors 48. Alternatively, a model may be employed that associates, for example, different patterns of brain activities with different mental states. Such a model may be used in conjunction with data received from other types of sensors (e.g., those types of sensors that do not measure brain activities) in order to associate, for example, a pattern of brain activity with one or more mental states.

Such a database or library may contain numerous brain activity patterns that may have been obtained by sampling a number of people from the general population, having, for example, similar metrics (e.g., age, gender, race, education, and so forth) as the subject (e.g., first authoring user 18). By asking each person what they felt (e.g., mental state) at the time when their brain activity pattern was recorded, or by using, for example, some other established testing procedures, each brain activity pattern stored in the library or database may be associated with one or more mental states. As a result, by comparing the determined brain activity pattern of the first authoring user 18 with the brain activity patterns (e.g., physical characteristic patterns) stored in the database or library, one or more mental states may be inferred from the observed physical characteristics of the first authoring user 18.

Figure 2T:
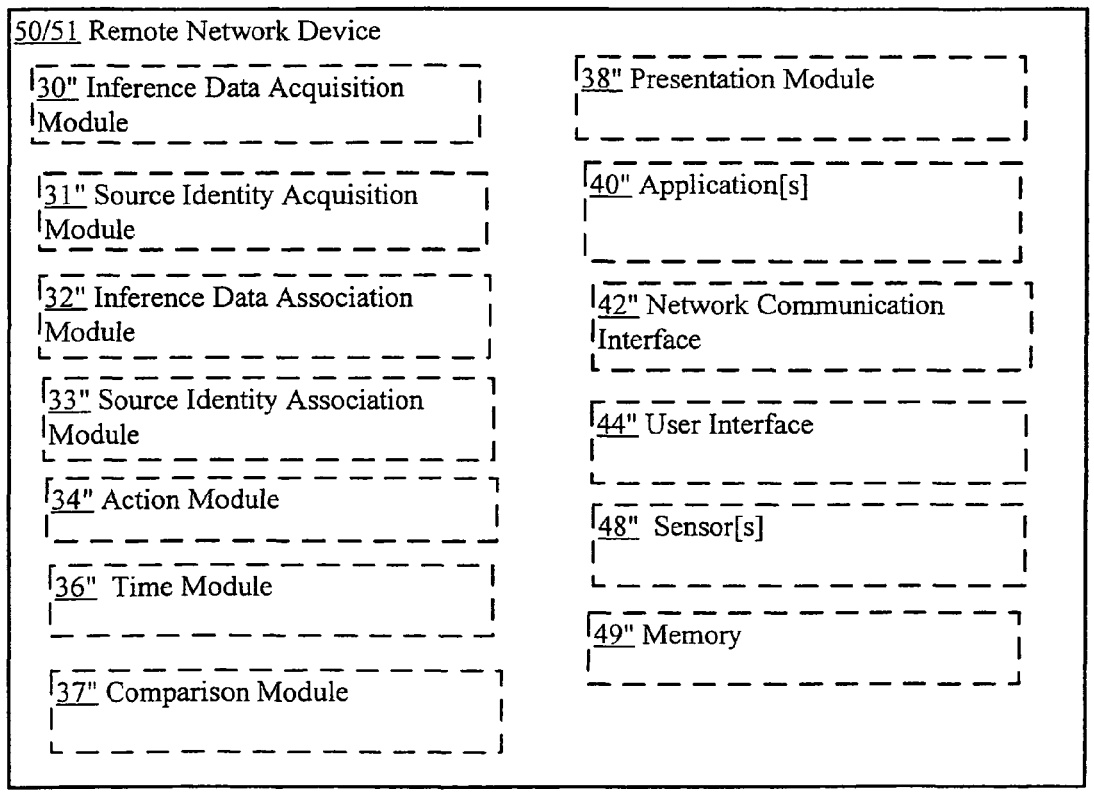
FIG. 2t shows another perspective of a remote network device 50/51 of FIG. 1.

Referring to FIG. 2t, which illustrates one of the remote network devices 50/51 of FIG. 1, in accordance with various embodiments. As briefly described earlier, one or more remote network devices 50/51 may be employed in some circumstances when, for example, the authoring device 10 is a network server and the one or more remote network devices 50/51 may be needed in order to collect inference data indicative of inferred mental states of authoring users (e.g., first authoring user 18 and second authoring user 19) in connection with the particular item 21. As depicted, each of the remote network devices 50/51 may include components similar to those components depicted in the authoring device 10 of FIG. 2a. For example, and as illustrated, the remote network devices 50/51 may each include an inference data acquisition module 30", a source identity acquisition module 31", an inference data association module 32," a source identity association module 33", an action module 34", a time module 36", a comparison module 37", a presentation module 38", one or more applications 40", a network communication interface 42", a user interface 44", one or more sensors 48", and/or memory 49". These components may further include sub-components and/or sub-modules similar to the sub-components and sub-modules previously depicted for the authoring device 10.

The various components (e.g., inference data acquisition module 30/30", source identity acquisition module 31/31", inference data association module 32/32", source identity association module 33/33", action module 34/34", time module 36/36", and so forth) along with their sub-components or sub-modules that may be included with the authoring device 10 or the remote network devices 50/51 may be embodied by hardware, software and/or firmware. For example, in some implementations the inference data acquisition module 30/30", the source identity acquisition module 31/31", the inference data association module 32/32", the source identity association module 33/33", the action module 34/34", the time module 36/36", the comparison module 37/37", and the presentation module 38/38" may be implemented with a processor (e.g., microprocessor, controller, and so forth) executing computer readable instructions (e.g., computer program product) stored in a storage medium (e.g., volatile or non-volatile memory) such as a signal-bearing medium. Alternatively, hardware such as application specific integrated circuit (ASIC) may be employed in order to implement such modules in some alternative implementations.

Figure 3:
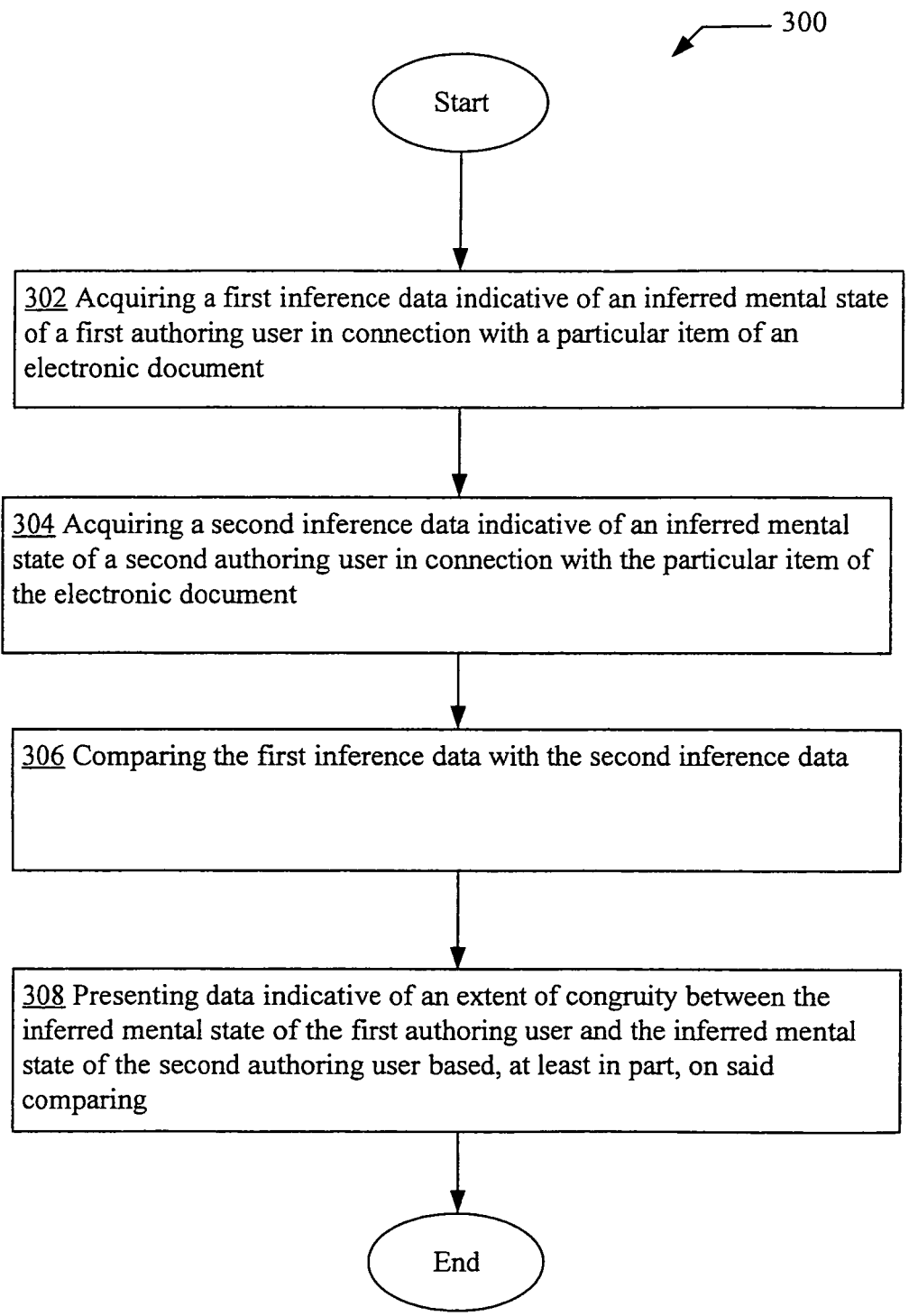
FIG. 3 is a high-level logic flowchart of a process.

FIG. 3 illustrates an operational flow 300 representing example operations related to acquisition and presentation of data indicative of an extent of congruence between inferred mental states of authoring users in connection with at least a particular item of an electronic document. An electronic document, as described herein, may be in reference to an electronic message (e.g., an email, an instant message (IM), a text message, a video message, an audio message, and so forth), a word processing document, or other types of electronic files. In various embodiments, various aspects of the operational flow 300 may be executed by, for example, the authoring device 10 or one or more of the remote network devices 50/51 of FIG. 1. That is, although operational flow 300 and the subsequent processes and operations (e.g., see FIGS. 4a to 20) will be generally described in the context of the authoring device 10 executing such processes and operations, one or more of these processes and operations may also be executed via the one or more remote network devices 50/51 in various alternative implementations.

In FIG. 3 and in the following figures that include various examples of operational flows, discussions and explanations may be provided with respect to the above-described exemplary environment of FIG. 1, and/or with respect to other examples (e.g., as provided in FIGS. 2a-2t) and contexts. However, it should be understood that the operational flows may be executed in a number of other environments and contexts, and/or in modified versions of FIGS. 1 and 2a-2t. Also, although the various operational flows are presented in the sequence(s) illustrated, it should be understood that the various operations may be performed in other orders than those which are illustrated, or may be performed concurrently.

Further, in FIG. 3 and in following figures, various operations may be depicted in a box-within-a-box manner. Such depictions may indicate that an operation in an internal box may comprise an optional example embodiment of the operational step illustrated in one or more external boxes. However, it should be understood that internal box operations may be viewed as independent operations separate from any associated external boxes and may be performed in any sequence with respect to all other illustrated operations, or may be performed concurrently.

In any event, after a start operation, the operational flow 300 may move to a first inference data acquisition operation 302, where acquiring a first inference data indicative of an inferred mental state of a first authoring user in connection with a particular item of an electronic document may be performed by, for example, the authoring device 10 of FIG. 1. For instance, the inference data acquisition module 30 (see FIG. 2a) of the authoring device 10 acquiring (e.g., by receiving from a remote network device 50 or by deriving locally at the authoring device 10) a first inference data indicative of an inferred mental state (e.g., state of happiness, state of anger, state of distress, or some other mental state) of a first authoring user 18 in connection with a particular item 21 of an electronic document 20.

The first inference data to be acquired may be in the form of raw or unprocessed data collected from, for example, one or more sensors 48 (e.g., one or more of an fMRI device 140, an fNIR device 141, an EEG device 142, an MEG device 143, and so forth), which when processed, may provide data that identifies one or more inferred mental states (e.g., state of frustration, state of trust, state of fear, and so forth) of the first authoring user 18. Alternatively, the first inference data to be acquired may be in the form of data that may directly identify one or more inferred mental states of the first authoring user 18.

Operational flow 300 may further include a second inference data acquisition operation 304 in which acquiring a second inference data indicative of an inferred mental state of a second authoring user in connection with the particular item of the electronic document may be executed by the authoring device 10. For instance, the inference data acquisition module 30 of the authoring device 10 acquiring (e.g., by receiving from a remote network device 51 or by deriving locally at the authoring device 10) a second inference data indicative of an inferred mental state (e.g., state of frustration, state of approval, state of disapproval, state of trust, and so forth) of a second authoring user 19 in connection with the particular item 21 of the electronic document 20.

Similar to the first inference data, the second inference data may be in the form of raw or unprocessed data collected from, for example, one or more sensors 48 (e.g., galvanic skin sensor device 144, heart rate sensor device 145, blood pressure sensor device 146, respiration sensor device 147, and so forth), which when processed, may provide data that identifies one or more inferred mental states (e.g., state of fear, state of surprise, state of inattention, and so forth) of the second authoring user 19. Alternatively, the second inference data to be acquired may be in the form of data that may directly identify one or more inferred mental states of the second authoring user 19.

After the first inference data acquisition operation 302 and the second inference data acquisition operation 304, the operational flow 300 may move to a comparison operation 306 in which comparing the first inference data with the second inference data may be executed by, for example, the authoring device 10. For instance, the comparison module 37 of the authoring device 10 comparing (e.g., determining the extent of difference) the first inference data (e.g., data as provided by the inference data reception module 101, by the inference data determination module 102, or by the mental state inference module 211) with the second inference data (e.g., data as provided by the inference data reception module 101, by the inference data determination module 102, or by the mental state inference module 211).

Once the comparison is made, a presentation operation 308 for presenting data indicative of an extent of congruity between the inferred mental state of the first authoring user and the inferred mental state of the second authoring user based, at least in part, on said comparing may be executed. For instance, the presentation module 38 of the authoring device 10 presenting (e.g., via the transmission module 212 or via the display module 213 through user interface 44) data indicative of an extent of congruity between the inferred mental state of the first authoring user 18 and the inferred mental state of the second authoring user 19 based, at least in part, on said comparing.

Figure 4A:
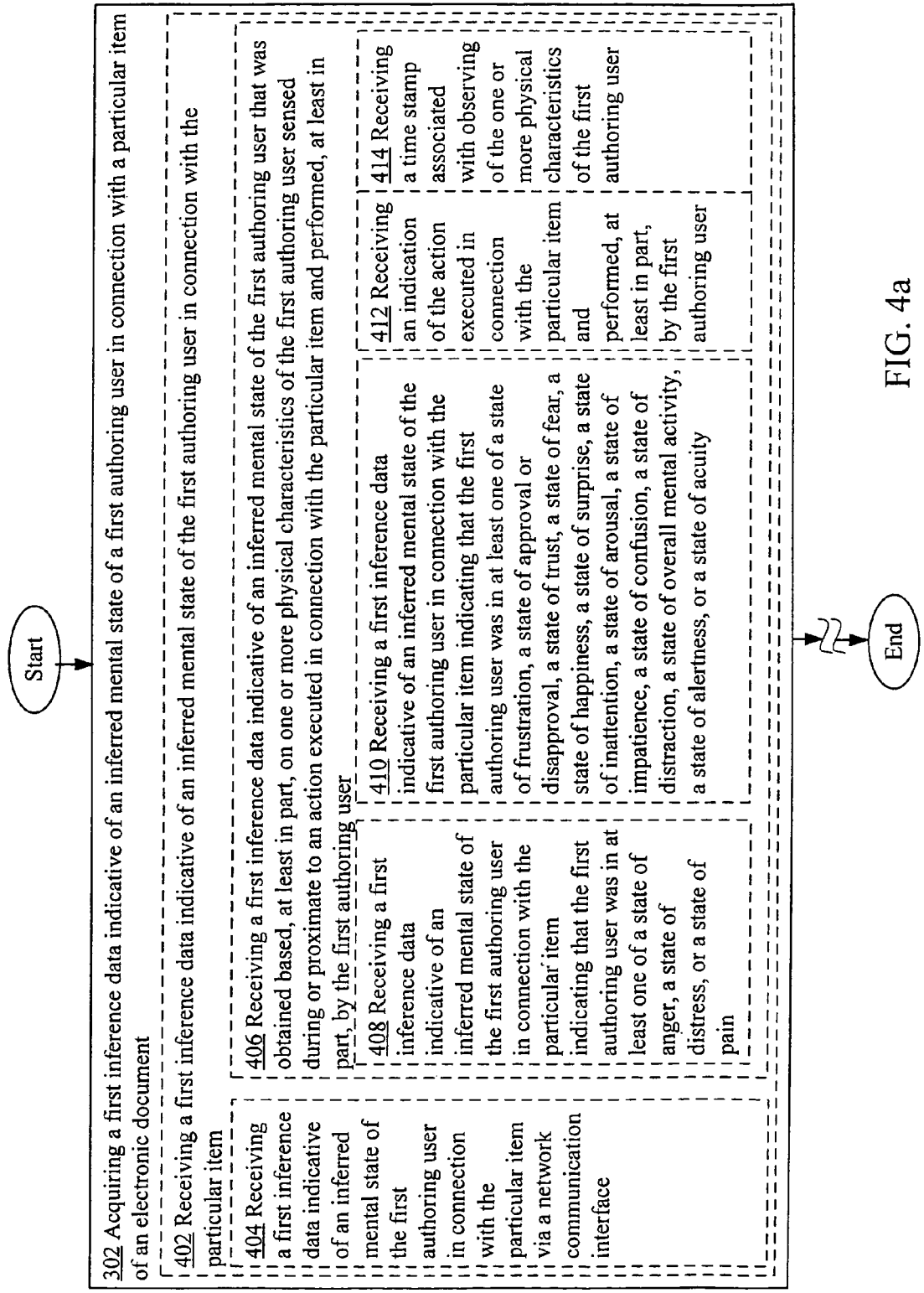
FIG. 4a is a high-level logic flowchart of a process depicting alternate implementations of the first inference data acquisition operation 302 of FIG. 3.

In various implementations, the first inference data acquisition operation 302 of FIG. 3 may include one or more additional operations as illustrated in, for example, FIGS. 4a to 4e. For example, in some implementations, the first inference data acquisition operation 302 may include a reception operation 402 for receiving a first inference data indicative of an inferred mental state of the first authoring user in connection with the particular item as illustrated in FIG. 4a. For instance, in some implementations, the inference data reception module 101 (see FIG. 2b) of the authoring device 10 receiving (e.g., from the remote network device 50) a first inference data (e.g., a first inference data that was derived based, at least in part, on data provided by one or more sensors 48" of a remote network device 50) indicative of an inferred mental state (e.g., state of anger, state of distress, and/or state of pain) of the first authoring user 18 in connection with the particular item 21.

In some implementations, the reception operation 402 may further include an operation 404 for receiving a first inference data indicative of an inferred mental state of the first authoring user in connection with the particular item via a network communication interface as illustrated in FIG. 4a. For instance, the inference data reception module 101 of the authoring device 10 receiving (e.g., via a wired and/or wireless network 16) a first inference data indicative of an inferred mental state (e.g., a state of frustration, a state of approval or disapproval, a state of trust, a state of fear, a state of happiness, a state of surprise, a state of inattention, a state of arousal, a state of impatience, a state of confusion, a state of distraction, a state of overall mental activity, a state of alertness, or a state of acuity) of the first authoring user 18 in connection with the particular item 21 via a network communication interface 42.

In the same or different implementations, the reception operation 402 may further include an operation 406 for receiving a first inference data indicative of an inferred mental state of the first authoring user that was obtained based, at least in part, on one or more physical characteristics of the first authoring user sensed during or proximate to an action executed in connection with the particular item and performed, at least in part, by the first authoring user as illustrated in FIG. 4a. For instance, the inference data reception module 101 of the authoring device 10 receiving a first inference data indicative of an inferred mental state (e.g., state of anger, state of distress, or state of pain) of the first authoring user 18 that was obtained based, at least in part, on one or more physical characteristics (e.g., cerebral characteristics) of the first authoring user 18 that was sensed (e.g., via one or more sensors 48" of remote network device 50) during or proximate to an action (e.g., creating, modifying, deleting, relocating, extracting, forwarding, storing activating, deactivating, tagging, associating, categorizing, substituting, inserting, or some other action) executed in connection with the particular item 21 and performed, at least in part, by the first authoring user 18.

In some implementations, operation 406 may further include an operation 408 for receiving a first inference data indicative of an inferred mental state of the first authoring user in connection with the particular item indicating that the first authoring user was in at least one of a state of anger, a state of distress, or a state of pain as illustrated in FIG. 4a. For instance, the inference data reception module 101 of the authoring device 10 receiving (e.g., via the network communication interface 42) a first inference data (e.g., first inference data that was derived based, at least in part, on data provided by one or more sensors 48" of the remote network device 50) indicative of an inferred mental state of the first authoring user 18 in connection with the particular item 21 indicating that the first authoring user 18 was in at least one of a state of anger, a state of distress, or a state of pain.

In some implementations, operation 406 may include an operation 410 for receiving a first inference data indicative of an inferred mental state of the first authoring user in connection with the particular item indicating that the first authoring user was in at least one of a state of frustration, a state of approval or disapproval, a state of trust, a state of fear, a state of happiness, a state of surprise, a state of inattention, a state of arousal, a state of impatience, a state of confusion, a state of distraction, a state of overall mental activity, a state of alertness, or a state of acuity as illustrated in FIG. 4a. For instance, the inference data reception module 101 of the authoring device 10 receiving (e.g., via the network communication interface 42) a first inference data (e.g., first inference data that was derived based, at least in part, on data provided by one or more sensors 48" of the remote network device 50) indicative of an inferred mental state of the first authoring user 18 in connection with the particular item 21 indicating that the first authoring user 18 was in at least one of a state of frustration, a state of approval or disapproval, a state of trust, a state of fear, a state of happiness, a state of surprise, a state of inattention, a state of arousal, a state of impatience, a state of confusion, a state of distraction, a state of overall mental activity, a state of alertness, or a state of acuity.

In the same or different implementations, operation 406 may include an operation 412 for receiving an indication of the action executed in connection with the particular item and performed, at least in part, by the first authoring user as illustrated in FIG. 4a. For instance, the inference data reception module 101 of the authoring device 10 receiving (e.g., via the network communication interface 42) an indication of the action (e.g., creating, modifying, deleting, relocating, extracting, forwarding, storing, activating, deactivating, tagging, associating, categorizing, substituting, or inserting) executed (e.g., via the action module 34" of the remote network device 50) in connection with the particular item 21 and performed, at least in part, by the first authoring user 18.

In the same or different implementations, operation 406 may also include an operation 414 for receiving a time stamp associated with observing of the one or more physical characteristics of the first authoring user as illustrated in FIG. 4a. For instance, the inference data reception module 101 of the authoring device 10 receiving (e.g., via the network communication interface 42) a time stamp (e.g., as provided by the time module 36" of the remote network device 50) associated with observing (e.g., via the one or more sensors 48" of the remote network device 50) of the one or more physical characteristic (e.g., cardiopulmonary characteristics) of the first authoring user 18.

Figure 4B:
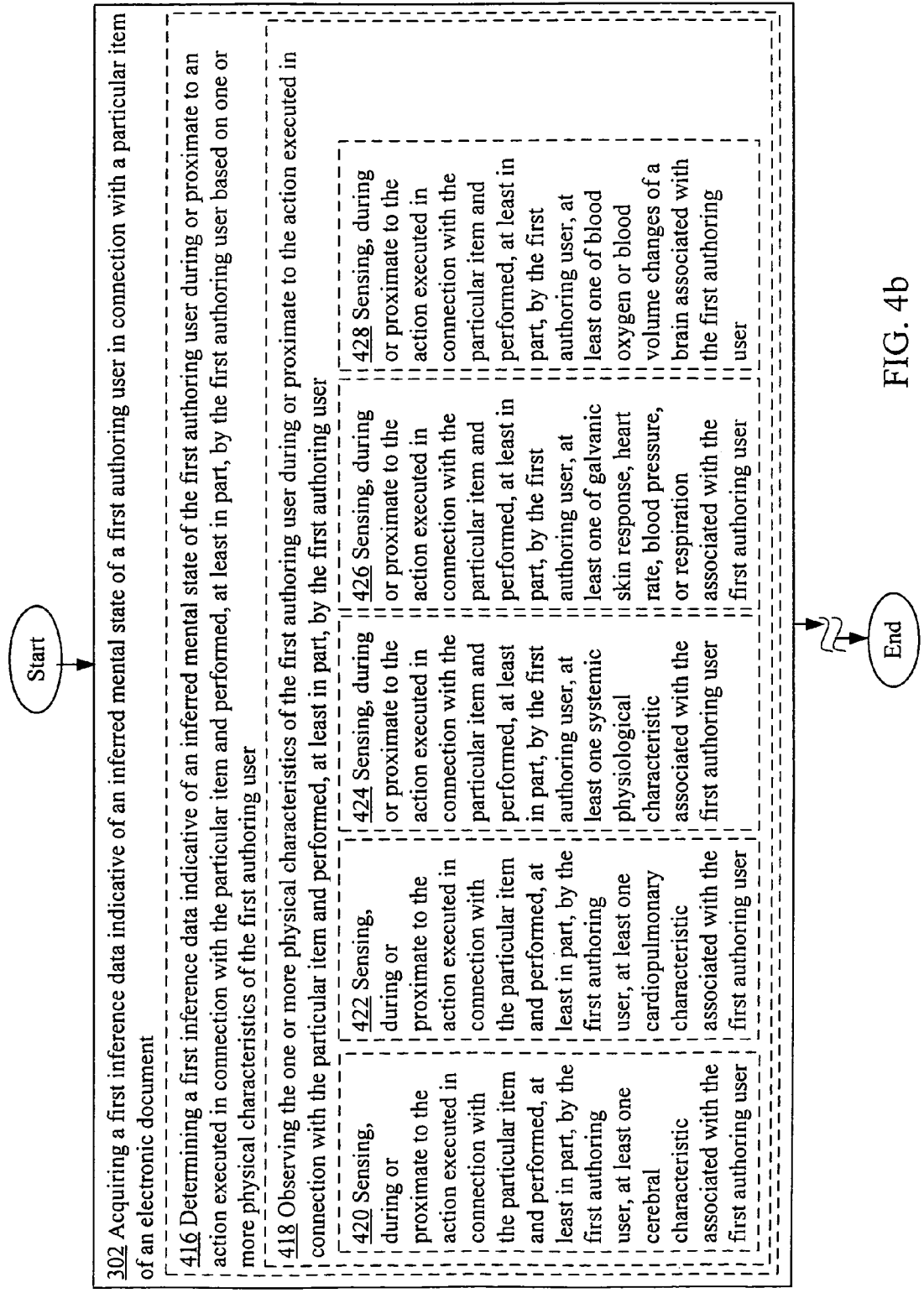
FIG. 4b is a high-level logic flowchart of a process depicting more alternate implementations of the first inference data acquisition operation 302 of FIG. 3.

In some implementations, the first inference data acquisition operation 302 may include a determination operation 416 for determining a first inference data indicative of an inferred mental state of the first authoring user during or proximate to an action executed in connection with the particular item and performed, at least in part, by the first authoring user based on one or more physical characteristics of the first authoring user as illustrated in FIG. 4b. For instance, the inference data determination module 102 of the authoring device 10 determining (e.g., deriving or computing based on data provided by one or more sensors 48) a first inference data indicative of an inferred mental state (e.g., a state of frustration, a state of approval or disapproval, a state of trust, a state of fear, a state of happiness, a state of surprise, a state of inattention, a state of arousal, a state of impatience, a state of confusion, a state of distraction, a state of overall mental activity, a state of alertness, or a state of acuity) of the first authoring user 18 during or proximate to an action (e.g., relocating, extracting, forwarding, storing, activating or deactivating, tagging, associating, or some other action) executed in connection with the particular item 21 and performed, at least in part, by the first authoring user 18 based on one or more physical characteristics (e.g., one or more systemic physiological characteristics) of the first authoring user 18.

Figure 4C:
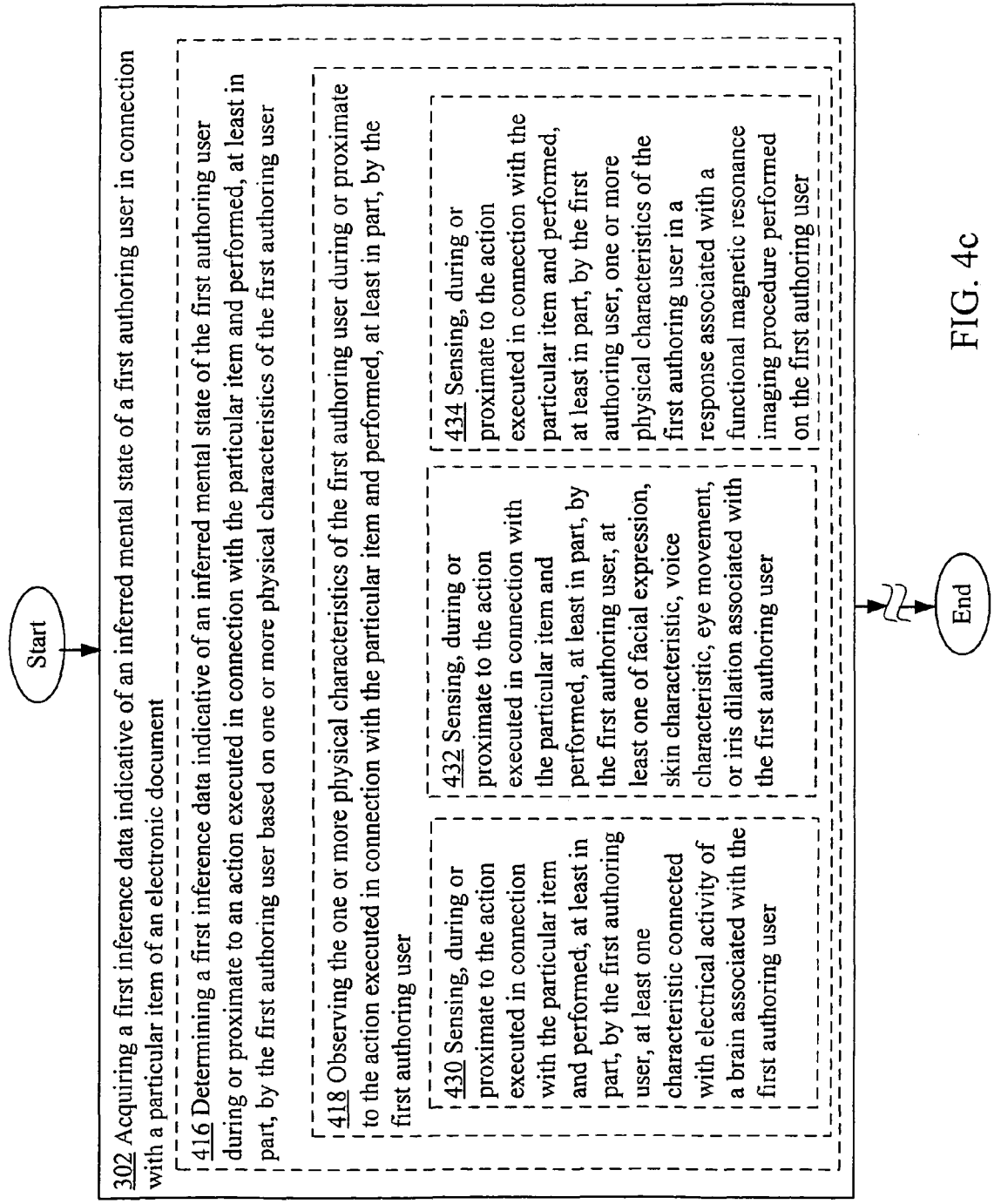
FIG. 4c is a high-level logic flowchart of a process depicting more alternate implementations of the first inference data acquisition operation 302 of FIG. 3.
Figure 4D:
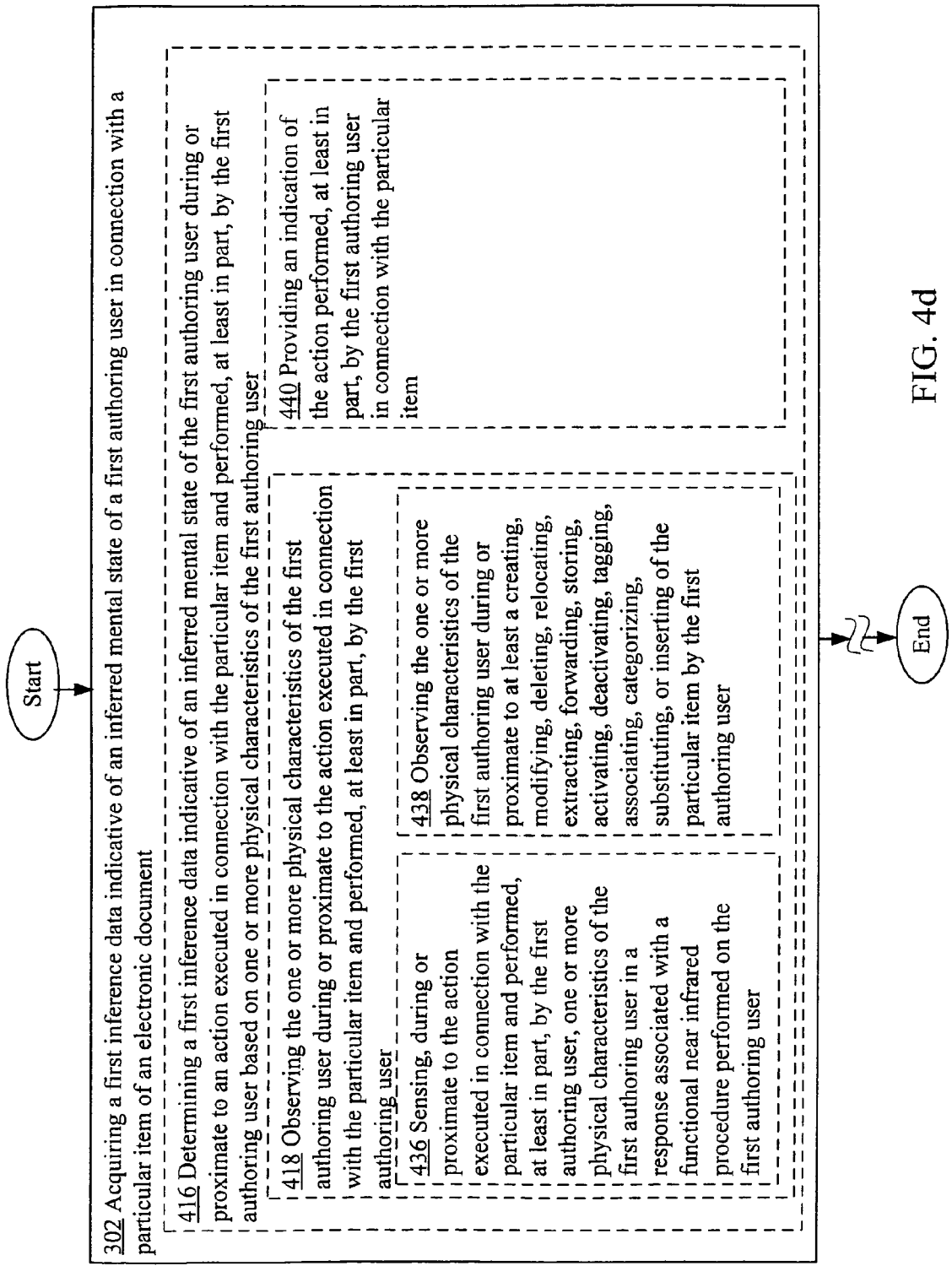
FIG. 4d is a high-level logic flowchart of a process depicting more alternate implementations of the first inference data acquisition operation 302 of FIG. 3.

In various implementations, the determination operation 416 may include one or more additional operations as illustrated in FIGS. 4b to 4d. For example, in some implementations, the determination operation 416 may include an observation operation 418 for observing the one or more physical characteristics of the first authoring user during or proximate to the action executed in connection with the particular item and performed, at least in part, by the first authoring user as illustrated in FIG. 4b. For instance, the physical characteristic observation module 104 (see FIG. 2b) of the authoring device 10 observing (e.g., via an fMRI device 140, an fNIR device 141, an EEG device 142, and/or an MEG device 143) the one or more physical characteristics (e.g., one or more cerebral, cardiopulmonary, and/or systemic physiological characteristics) of the first authoring user 18 during or proximate to the action (e.g., categorizing, substituting, inserting, or some other action) executed in connection with the particular item 21 and performed, at least in part, by the first authoring user 18.

In various implementations, the observation operation 418 may further include one or more additional operations. For example, in some implementations, the observation operation 418 may include an operation 420 for sensing, during or proximate to the action executed in connection with the particular item and performed, at least in part, by the first authoring user, at least one cerebral characteristic associated with the first authoring user as illustrated in FIG. 4b. For instance, the physical characteristic sensing module 108 (see FIG. 2b) of the authoring device 10 sensing (e.g., via an fMRI device 140, an fNIR device 141, an EEG device 142, and/or an MEG device 143), during or proximate to the action (e.g., categorizing, substituting, inserting, or some other action) executed in connection with the particular item 21 and performed, at least in part, by the first authoring user 18, at least one cerebral characteristic (e.g., blood volume changes or characteristics associated with electrical activities of the brain) associated with the first authoring user 18.

In some implementations, the observation operation 418 may also include an operation 422 for sensing, during or proximate to the action executed in connection with the particular item and performed, at least in part, by the first authoring user, at least one cardiopulmonary characteristic associated with the first authoring user as illustrated in FIG. 4b. For instance, the physical characteristic sensing module 108 of the authoring device 10 sensing (e.g., via a heart rate sensor device 145), during or proximate to the action (e.g., creating, modifying, deleting, or some other action) executed in connection with the particular item 21 and performed, at least in part, by the first authoring user 18, at least one cardiopulmonary characteristic (e.g., heart rate) associated with the first authoring user 18.

In some implementations, the observation operation 418 may also include an operation 424 for sensing, during or proximate to the action executed in connection with the particular item and performed, at least in part, by the first authoring user, at least one systemic physiological characteristic associated with the first authoring user as illustrated in FIG. 4b. For instance, the physical characteristic sensing module 108 of the authoring device 10 sensing (e.g., via a blood pressure sensor device 146), during or proximate to the action (e.g., relocating, extracting, activating, deactivating, associating, or some other action) executed in connection with the particular item 21 and performed, at least in part, by the first authoring user 18, at least one systemic physiological characteristic (e.g., blood pressure) associated with the first authoring user 18.

In some implementations, the observation operation 418 may include an operation 426 for sensing, during or proximate to the action executed in connection with the particular item and performed, at least in part, by the first authoring user, at least one of galvanic skin response, heart rate, blood pressure, or respiration associated with the first authoring user as illustrated in FIG. 4b. For instance, the physical characteristic sensing module 108 of the authoring device 10 sensing (e.g., via a galvanic skin sensor device 144, a heart rate sensor device 145, a blood pressure sensor device 146, or a respiration sensor device 147), during or proximate to the action (e.g., forwarding, storing, tagging, or some other action) executed in connection with the particular item 21 and performed, at least in part, by the first authoring user 18, at least one of galvanic skin response, heart rate, blood pressure, or respiration associated with the first authoring user 18.

In some implementations, the observation operation 418 may also include an operation 428 for sensing, during or proximate to the action executed in connection with the particular item and performed, at least in part, by the first authoring user, at least one of blood oxygen or blood volume changes of a brain associated with the first authoring user as illustrated in FIG. 4b. For instance, the physical characteristic sensing module 108 of the authoring device 10 sensing (e.g., via an fMRI device 140 or an fNIR device 141), during or proximate to the action (e.g., categorizing, substituting, inserting, or some other action) executed in connection with the particular item 21 and performed, at least in part, by the first authoring user 18, at least one of blood oxygen or blood volume changes of a brain associated with the first authoring user 18.

In some implementations, the observation operation 418 may also include an operation 430 for sensing, during or proximate to the action executed in connection with the particular item and performed, at least in part, by the first authoring user, at least one characteristic connected with electrical activity of a brain associated with the first authoring user as illustrated in FIG. 4c. For instance, the physical characteristic sensing module 108 of the authoring device 10 sensing (e.g., via an EEG device 142 or an MEG device 143), during or proximate to the action (e.g., creating, modifying, deleting, or some other action) executed in connection with the particular item 21 and performed, at least in part, by the first authoring user 18, at least one characteristic connected with electrical activity of a brain associated with the first authoring user 18.

In some implementations, the observation operation 418 may also include an operation 432 for sensing, during or proximate to the action executed in connection with the particular item and performed, at least in part, by the first authoring user, at least one of facial expression, skin characteristic, voice characteristic, eye movement, or iris dilation associated with the first authoring user as illustrated in FIG. 4c. For instance, the physical characteristic sensing module 108 of the authoring device 10 sensing (e.g., via a facial expression sensor device 148, a skin characteristic sensor device 149, a voice response device 150, gaze tracking device 151, or an iris response device 152), during or proximate to the action (e.g., relocating, extracting, activating, deactivating, associating, or some other action) executed in connection with the particular item 21 and performed, at least in part, by the first authoring user 18, at least one of facial expression, skin characteristic, voice characteristic, eye movement, or iris dilation associated with the first authoring user 18.

In some implementations, the observation operation 418 may also include an operation 434 for sensing, during or proximate to the action executed in connection with the particular item and performed, at least in part, by the first authoring user, one or more physical characteristics of the first authoring user in a response associated with a functional magnetic resonance imaging procedure performed on the first authoring user as illustrated in FIG. 4c. For instance, the physical characteristic sensing module 108 of the authoring device 10 sensing (e.g., via an fMRI device 140), during or proximate to the action (e.g., forwarding, storing, tagging, or some other action) executed in connection with the particular item 21 and performed, at least in part, by the first authoring user 18, one or more physical characteristics (e.g., cerebral characteristics) of the first authoring user 18 in a response associated with a functional magnetic resonance imaging procedure performed on the first authoring user 18.

In some implementations, the observation operation 418 may also include an operation 436 for sensing, during or proximate to the action executed in connection with the particular item and performed, at least in part, by the first authoring user, one or more physical characteristics of the first authoring user in a response associated with a functional near infrared procedure performed on the first authoring user as illustrated in FIG. 4d. For instance, the physical characteristic sensing module 108 of the authoring device 10 sensing (e.g., via an fNIR device 141), during or proximate to the action (e.g., categorizing, substituting, inserting, or some other action) executed in connection with the particular item 21 and performed, at least in part, by the first authoring user 18, one or more physical characteristics (e.g., cerebral characteristics) of the first authoring user 18 in a response associated with a functional near infrared procedure performed on the first authoring user 18.

In some implementations, the observation operation 418 may also include an operation 438 for observing the one or more physical characteristics of the first authoring user during or proximate to at least a creating, modifying, deleting, relocating, extracting, forwarding, storing, activating, deactivating, tagging, associating, categorizing, substituting, or inserting of the particular item by the first authoring user as illustrated in FIG. 4d. For instance, the physical characteristic observation module 104 of the authoring device 10 observing (e.g., via the physical characteristic observation module 104) the one or more physical characteristics (e.g., one or more cerebral characteristics) of the first authoring user 18 during or proximate to at least a creating, modifying, deleting, relocating, extracting, forwarding, storing, activating, deactivating, tagging, associating, categorizing, substituting, or inserting of the particular item 21 by the first authoring user 18.

In various alternative implementations, the observation of the one or more physical characteristics of the first authoring user 18 may occur during or proximate to other types of actions (which may be directly or indirectly connected to the particular item 21) other than those described above (e.g., creating, deleting, modifying, and so forth). For instance, in some alternative implementations, the observation of the one or more physical characteristics of the first authoring user 18 may occur during or proximate to a searching operation (e.g., in order to find particular information) initiated by the first authoring user 18 and that may have been prompted while accessing the particular item 21.

In various implementations, the determination operation 416 may also include an operation 440 for providing an indication of the action performed, at least in part, by the first authoring user in connection with the particular item as illustrated in FIG. 4d. For instance, the action module 34 of the authoring device 10 providing an indication (e.g., name or symbolic representation) of the action (e.g., creating, modifying, deleting, relocating, extracting, forwarding, storing, activating, deactivating, tagging, associating, categorizing, substituting, or inserting) performed, at least in part, by the first authoring user 18 in connection with the particular item 21.

Figure 4E:
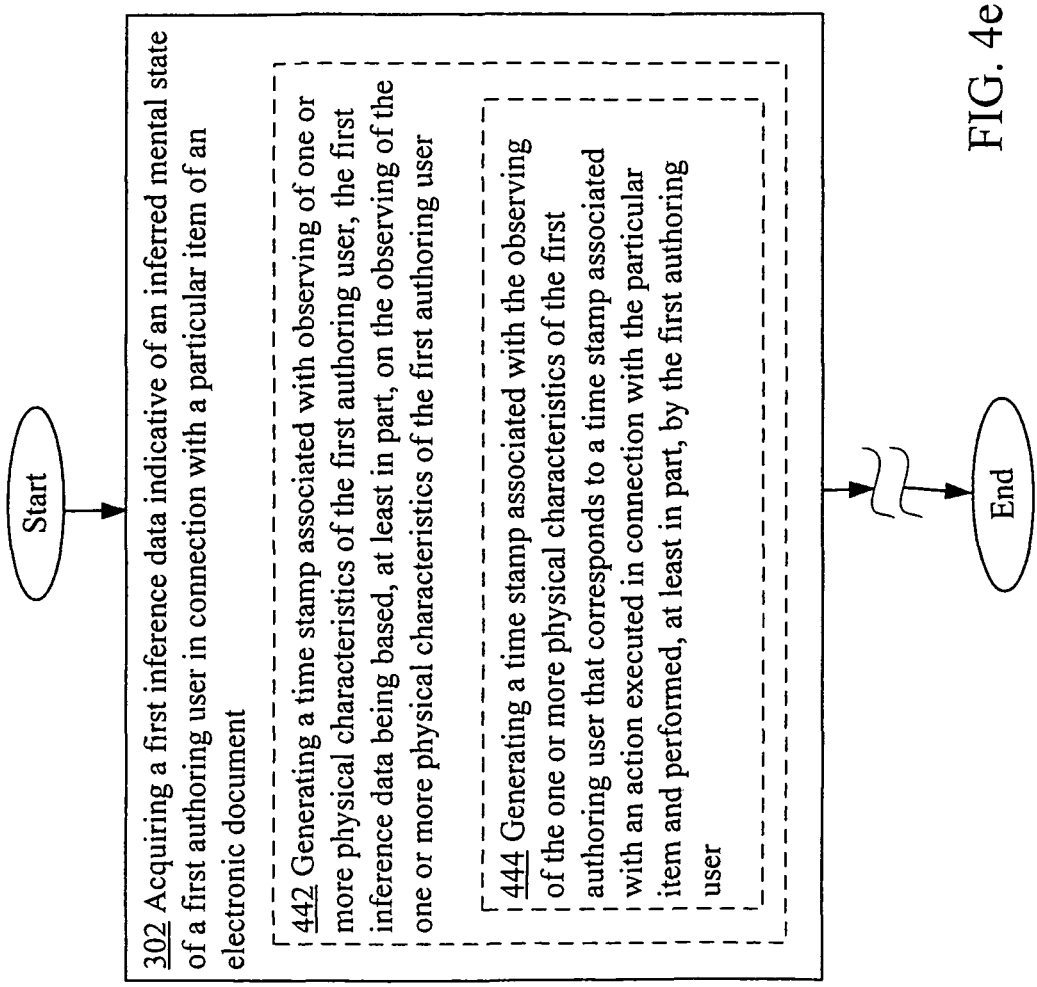
FIG. 4e is a high-level logic flowchart of a process depicting more alternate implementations of the first inference data acquisition operation 302 of FIG. 3.

In some implementations, the first inference data acquisition operation 302 of FIG. 3 may further include an operation 442 for generating a time stamp associated with observing of one or more physical characteristics of the first authoring user, the first inference data being based, at least in part, on the observing of the one or more physical characteristics of the first authoring user as illustrated in FIG. 4e. For instance, the time stamp module 125 (see FIG. 2j) of the authoring device 10 generating a time stamp associated with observing (e.g., via an fMRI device 140, an fNIR device 141, an EEG device 142, and/or an MEG device 143) of one or more physical characteristics (e.g., one or more cerebral characteristics) of the first authoring user 18, the first inference data being based, at least in part, on the observing of the one or more physical characteristics of the first authoring user 18.

In some implementations, operation 442 may further include an operation 444 for generating a time stamp associated with the observing of the one or more physical characteristics of the first authoring user that corresponds to a time stamp associated with an action executed in connection with the particular item and performed, at least in part, by the first authoring user as illustrated in FIG. 4e. For instance, the time stamp module 125 of the authoring device 10 generating a time stamp associated with the observing of the one or more physical characteristics of the first authoring user 18 that corresponds to a time stamp associated with an action (e.g., creating, modifying, deleting, or some other action) executed in connection with the particular item 21 and performed, at least in part, by the first authoring user 18.

Figure 4F:
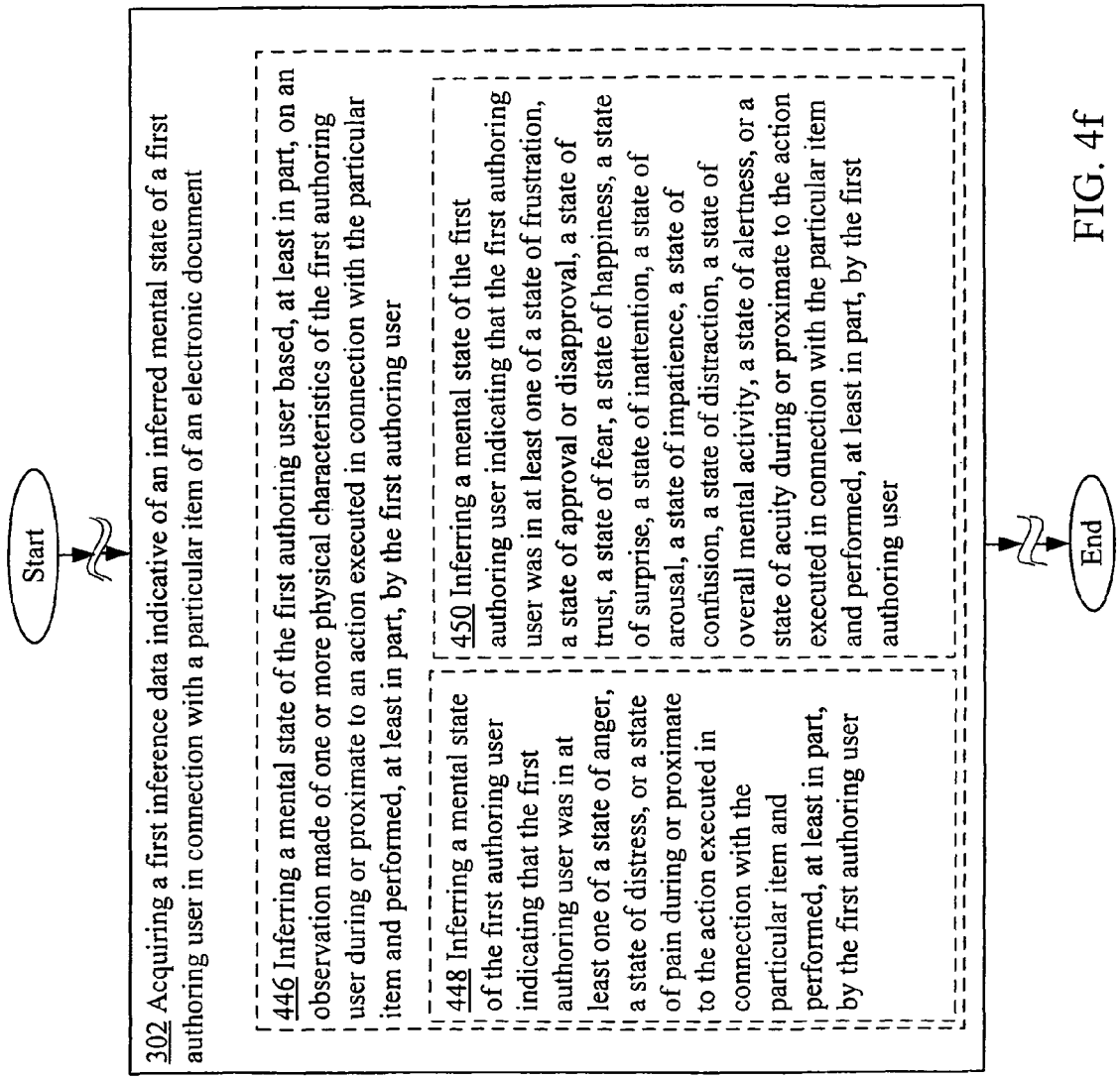
FIG. 4f is a high-level logic flowchart of a process depicting more alternate implementations of the first inference data acquisition operation 302 of FIG. 3.

In some implementations, the first inference data acquisition operation 302 of FIG. 3 may include an inference operation 446 for inferring a mental state of the first authoring user based, at least in part, on an observation made of one or more physical characteristics of the first authoring user during or proximate to an action executed in connection with the particular item and performed, at least in part, by the first authoring user as illustrated in FIG. 4f. For instance, the mental state inference module 211 (see FIG. 2b) of the authoring device 10 inferring (e.g., determining or deriving) a mental state of the first authoring user 18 based, at least in part, on an observation made (e.g., via a galvanic skin sensor device 144, a heart rate sensor device 145, a blood pressure sensor device 146, a respiration sensor device 147, a facial expression sensor device 148, a skin characteristic sensor device 149, a voice response device 150, a gaze tracking device 151, or an iris response device 152) of one or more physical characteristics (e.g., cardiopulmonary characteristics, systemic physiological characteristics, or some other physical characteristics) of the first authoring user 18 during or proximate to an action (e.g., creating, modifying, deleting, or some other action) executed in connection with the particular item 21 and performed, at least in part, by the first authoring user 18.

In some implementations, the inference operation 446 may further include an operation 448 for inferring a mental state of the first authoring user indicating that the first authoring user was in at least one of a state of anger, a state of distress, or a state of pain during or proximate to the action executed in connection with the particular item and performed, at least in part, by the first authoring user as illustrated in FIG. 4f. For instance, the mental state inference module 211 of the authoring device 10 inferring (e.g., determining or deriving based on data provided by an fMRI device 140, an fNIR device 141, an EEG device 142, an MEG device 143, and/or some other sensor) a mental state of the first authoring user 18 indicating that the first authoring user 18 was in at least one of a state of anger, a state of distress, or a state of pain during or proximate to the action (e.g., relocating, extracting, activating, deactivating, associating, or some other action) executed in connection with the particular item 21 and performed, at least in part, by the first authoring user 18.

In some implementations, the inference operation 446 may include an operation 450 for inferring a mental state of the first authoring user indicating that the first authoring user was in at least one of a state of frustration, a state of approval or disapproval, a state of trust, a state of fear, a state of happiness, a state of surprise, a state of inattention, a state of arousal, a state of impatience, a state of confusion, a state of distraction, a state of overall mental activity, a state of alertness, or a state of acuity during or proximate to the action executed in connection with the particular item and performed, at least in part, by the first authoring user as illustrated in FIG. 4f. For instance, the mental state inference module 211 of the authoring device 10 inferring (e.g., determining or deriving based on data provided by a galvanic skin sensor device 144, a heart rate sensor device 145, a blood pressure sensor device 146, a respiration sensor device 147, a facial expression sensor device 148, a skin characteristic sensor device 149, a voice response device 150, a gaze tracking device 151, an iris response device 152, and/or some other sensor) a mental state of the first authoring user 18 indicating that the first authoring user 18 was in at least one of a state of frustration, a state of approval or disapproval, a state of trust, a state of fear, a state of happiness, a state of surprise, a state of inattention, a state of arousal, a state of impatience, a state of confusion, a state of distraction, a state of overall mental activity, a state of alertness, or a state of acuity during or proximate to the action (e.g., forwarding, storing, tagging, or some other action) executed in connection with the particular item 21 and performed, at least in part, by the first authoring user 18.

Referring back to FIG. 3, in various implementations the second inference data acquisition operation 304 may include one or more additional operations as illustrated in, for example, FIGS. 5a to 6d. For example, in some implementations, the second inference data acquisition operation 304 may include a reception operation 506 for receiving a second inference data indicative of an inferred mental state of the second authoring user in connection with the particular item as illustrated in FIG. 5a. For instance, the inference data reception module 101 (see FIG. 2b) of the authoring device 10 receiving (e.g., via a network communication interface 42) a second inference data (e.g., second inference data that was derived based, at least in part, on data provided by one or more sensors 48" of a remote network device 51) indicative of an inferred mental state of the second authoring user 19 in connection with the particular item 21.

The reception operation 506 may further include one or more additional operations in various alternative implementations. For instance, in some implementations, the reception operation 506 may include an operation 508 for receiving a second inference data indicative of an inferred mental state of the second authoring user in connection with the particular item via a network communication interface as illustrated in FIG. 5a. For instance, the inference data reception module 101 of the authoring device 10 receiving (e.g., via a wired and/or wireless network 16) a second inference data indicative of an inferred mental state (e.g., a state of frustration, a state of approval or disapproval, a state of trust, a state of fear, a state of happiness, a state of surprise, a state of inattention, a state of arousal, a state of impatience, a state of confusion, a state of distraction, a state of overall mental activity, a state of alertness, or a state of acuity) of the second authoring user 19 in connection with the particular item 21 via a network communication interface 42.

In the same or different implementations, the reception operation 506 may also include an operation 510 for receiving a second inference data indicative of an inferred mental state of the second authoring user that was obtained based, at least in part, on one or more physical characteristics of the second authoring user sensed during or proximate to an action executed in connection with the particular item and performed, at least in part, by the second authoring user as illustrated in FIG. 5a. For instance, the inference data reception module 101 of the authoring device 10 receiving a second inference data indicative of an inferred mental state (e.g., state of anger, state of distress, or state of pain) of the second authoring user 19 that was obtained based, at least in part, on one or more physical characteristics (e.g., cerebral characteristics) of the second authoring user 19 that was sensed (e.g., via one or more sensors 48" of remote network device 51) during or proximate to an action (e.g., creating, modifying, deleting, relocating, extracting, forwarding, storing, activating, deactivating, tagging, associating, categorizing, substituting, inserting, or some other action) executed in connection with the particular item 21 and performed, at least in part, by the second authoring user 19. Alternatively, the reception operation 506 may include an operation for receiving a second inference data indicative of an inferred mental state of the second authoring user that was obtained based, at least in part, on one or more physical characteristics of the second authoring user sensed during or proximate to an action executed in connection with another item of the electronic document and performed, at least in part, by the second authoring user. For example, the inference data reception module 101 of the authoring device 10 receiving a second inference data indicative of an inferred mental state of the second authoring user 19 that was obtained based, at least in part, on one or more physical characteristics of the second authoring user 19 sensed during or proximate to an action (e.g., creating) executed in connection with another particular item 22 of the electronic document 20 and performed, at least in part, by the second authoring user 19 in response, by the second authoring user 19, to the creation of the parituclar item 21 by the first authoring user 18.

Figure 5B:
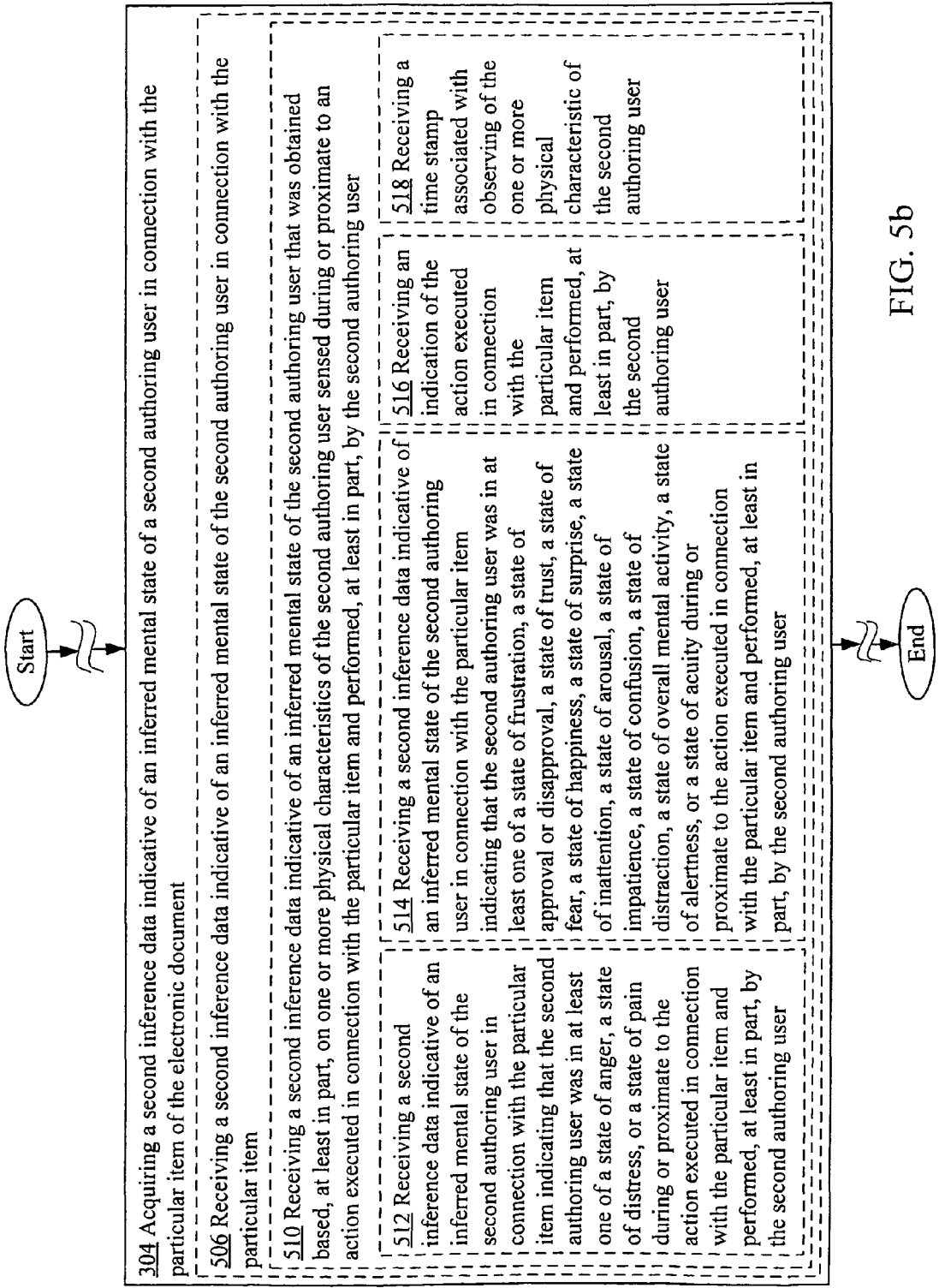

In various implementations, operation 510 may include one or more additional operations. For example, in some implementations, operation 510 may include an operation 512 for receiving a second inference data indicative of an inferred mental state of the second authoring user in connection with the particular item indicating that the second authoring user was in at least one of a state of anger, a state of distress, or a state of pain during or proximate to the action executed in connection with the particular item and performed, at least in part, by the second authoring user as illustrated in FIG. 5b. For instance, the inference data reception module 101 of the authoring device 10 receiving (e.g., via the network communication interface 42) a second inference data (e.g., second inference data that was derived based, at least in part, on data provided by one or more sensors 48" of the remote network device 51) indicative of an inferred mental state of the second authoring user 19 in connection with the particular item 21 indicating that the second authoring user 19 was in at least one of a state of anger, a state of distress, or a state of pain during or proximate to the action (e.g., creating, modifying, inserting, or some other action) executed (e.g., via the remote network device 51) in connection with the particular item 21 and performed, at least in part, by the second authoring user 19.

In some implementations, operation 510 may include an operation 514 for receiving a second inference data indicative of an inferred mental state of the second authoring user in connection with the particular item indicating that the second authoring user was in at least one of a state of frustration, a state of approval or disapproval, a state of trust, a state of fear, a state of happiness, a state of surprise, a state of inattention, a state of arousal, a state of impatience, a state of confusion, a state of distraction, a state of overall mental activity, a state of alertness, or a state of acuity during or proximate to the action executed in connection with the particular item and performed, at least in part, by the second authoring user as illustrated in FIG. 5b. For instance, the inference data reception module 101 of the authoring device 10 receiving (e.g., via the network communication interface 42) a second inference data (e.g., second inference data that was derived based, at least in part, on data provided by one or more sensors 48" of the remote network device 51) indicative of an inferred mental state of the second authoring user 19 in connection with the particular item 21 indicating that the second authoring user 19 was in at least one of a state of frustration, a state of approval or disapproval, a state of trust, a state of fear, a state of happiness, a state of surprise, a state of inattention, a state of arousal, a state of impatience, a state of confusion, a state of distraction, a state of overall mental activity, a state of alertness, or a state of acuity during or proximate to the action (e.g., relocating, extracting, forwarding, or some other action) executed (e.g., via the remote network device 51) in connection with the particular item 21 and performed, at least in part, by the second authoring user 19.

In some implementations, operation 510 may include an operation 516 for receiving an indication of the action executed in connection with the particular item and performed, at least in part, by the second authoring user as illustrated in FIG. 5b. For instance, the inference data reception module 101 of the authoring device 10 receiving (e.g., via the network communication interface 42) an indication of the action (e.g., creating, modifying, deleting, relocating, extracting, forwarding, storing, activating, deactivating, tagging, associating, categorizing, substituting, or inserting) executed (e.g., via the action module 34" of the remote network device 51) in connection with the particular item 21 and performed, at least in part, by the second authoring user 19.

In some implementations, operation 510 may further include an operation 518 for receiving a time stamp associated with observing of the one or more physical characteristics of the second authoring user as illustrated in FIG. 5b. For instance, the inference data reception module 101 of the authoring device 10 receiving (e.g., via the network communication interface 42) a time stamp (e.g., as provided by the time module 36" of the remote network device 51) associated with observing (e.g., via the one or more sensors 48" of the remote network device 51) of the one or more physical characteristic (e.g., cardiopulmonary characteristics) of the second authoring user 19.

Figure 6A:
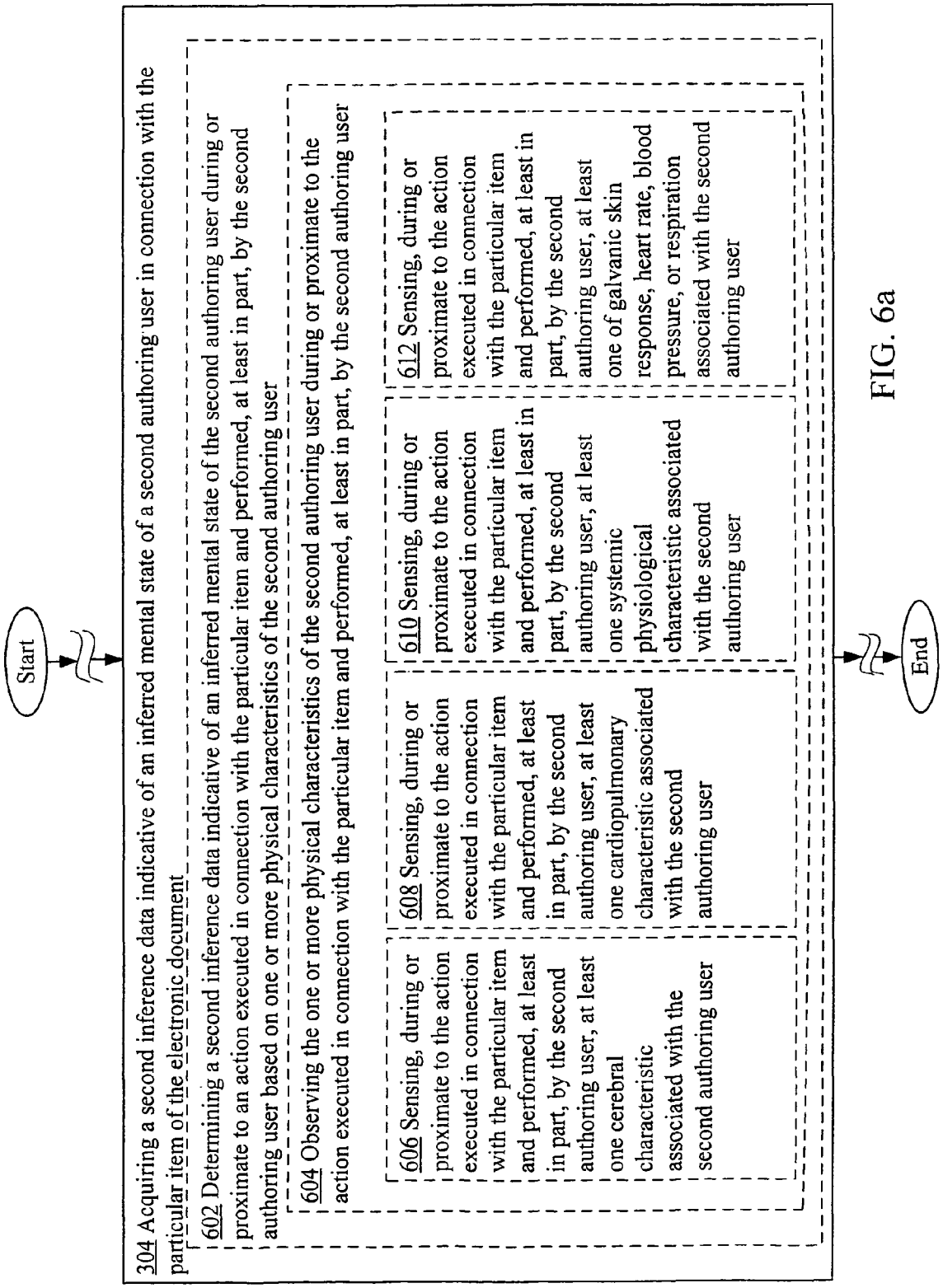
FIG. 6a is a high-level logic flowchart of a process depicting more alternate implementations of the second inference data acquisition operation 304 of FIG. 3.

In various embodiments, the second inference data acquisition operation 304 of FIG. 3 may include a determination operation 602 for determining a second inference data indicative of an inferred mental state of the second authoring user during or proximate to an action executed in connection with the particular item and performed, at least in part, by the second authoring user based on one or more physical characteristics of the second authoring user as illustrated in FIG. 6a. For instance, the inference data determination module 102 (see FIG. 2b) of the authoring device 10 determining (e.g., deriving or computing based on data provided by one or more sensors 48) a second inference data indicative of an inferred mental state (e.g., a state of frustration, a state of approval or disapproval, a state of trust, a state of fear, a state of happiness, a state of surprise, a state of inattention, a state of arousal, a state of impatience, a state of confusion, a state of distraction, a state of overall mental activity, a state of alertness, or a state of acuity) of the second authoring user 19 during or proximate to an action (e.g., relocating, extracting, forwarding, storing, activating or deactivating, tagging, associating, or some other action) executed in connection with the particular item 21 and performed, at least in part, by the second authoring user 19 based on one or more physical characteristics (e.g., one or more systemic physiological characteristics) of the second authoring user 19. Alternatively, the second inference data acquisition operation 304 of FIG. 3 may include a determination operation for determining a second inference data indicative of an inferred mental state of the second authoring user during or proximate to an action executed in connection with another item of the electronic document and performed, at least in part, by the second authoring user based on one or more physical characteristics of the second authoring user. For instance, the inference data determination module 102 of the authoring device 10 determining a second inference data indicative of an inferred mental state of the second authoring user 19 during or proximate to an action (e.g., creating of another particular item 22) executed in connection with the another particular item 22 of the electronic document 20 and performed, at least in part, by the second authoring user 19 in response, by the second authoring user 19, to the creation of the particular item 21 by the first authoring user 18.

The determination operation 602 may further include, in various alternative implementations, one or more additional operations. For example, in some implementations, the determination operation 602 may include an observation operation 604 for observing the one or more physical characteristics of the second authoring user during or proximate to the action executed in connection with the particular item and performed, at least in part, by the second authoring user as illustrated in FIG. 6a. For instance, the physical characteristic observation module 104 (see FIG. 2b) of the authoring device 10 observing (e.g., via an fMRI device 140, an fNIR device 141, an EEG device 142, and/or an MEG device 143) the one or more physical characteristics (e.g., one or more cerebral characteristics) of the second authoring user 19 during or proximate to the action (e.g., categorizing, substituting, inserting, or some other action) executed in connection with the particular item 21 and performed, at least in part, by the second authoring user 19.

In some alternative implementations, the observation of the one or more physical characteristics of the second authoring user 19 may occur during a second time period that may be a later time period than a first time period in which the action in connection with the particular item 21 is executed by the second authoring user 19. For example, this may be the case when changes to the one or more physical characteristics (e.g., cerebral state) of the second authoring user 19 occur several minutes after the action has been performed. Under these circumstances, the one or more physical characteristics of the second authoring user 19 may or may not be observed during the first time period since the observations of the one or more physical characteristics during the first time period may not be needed at least with respect to the acquisition of the second inference data. In still other implementations, the observation of the one or more physical characteristics of the second authoring user 19 in order to acquire the second inference may occur at different points or increments of time in order to provide, for example, a more "accurate picture" of the one or physical characteristics of the second authoring user 19 with respect to the action executed in connection with the particular item 21 and performed, at least in part, by the second authoring user 19.

In some implementations, the observation operation 604 may include an operation 606 for sensing, during or proximate to the action executed in connection with the particular item and performed, at least in part, by the second authoring user, at least one cerebral characteristic associated with the second authoring user as illustrated in FIG. 6a. For instance, the physical characteristic sensing module 108 (see FIG. 2b) of the authoring device 10 sensing (e.g., via an fMRI device 140, an fNIR device 141, an EEG device 142, and/or an MEG device 143), during or proximate to the action (e.g., categorizing, substituting, inserting, or some other action) executed in connection with the particular item 21 and performed, at least in part, by the second authoring user 19, at least one cerebral characteristic associated with the second authoring user 19.

In some implementations, the observation operation 604 may include an operation 608 for sensing, during or proximate to the action executed in connection with the particular item and performed, at least in part, by the second authoring user, at least one cardiopulmonary characteristic associated with the second authoring user as illustrated in FIG. 6a. For instance, the physical characteristic sensing module 108 of the authoring device 10 sensing (e.g., via a heart sensor device 145), during or proximate to the action (e.g., creating, modifying, deleting, or some other action) executed in connection with the particular item 21 and performed, at least in part, by the second authoring user 19, at least one cardiopulmonary characteristic (e.g. heart rate) associated with the second authoring user 19.

In some implementations, the observation operation 604 may include an operation 610 for sensing, during or proximate to the action executed in connection with the particular item and performed, at least in part, by the second authoring user, at least one systemic physiological characteristic associated with the second authoring user as illustrated in FIG. 6a. For instance, the physical characteristic sensing module 108 of the authoring device 10 sensing (e.g., via a blood pressure sensor device 146), during or proximate to the action (e.g., relocating, extracting, activating, deactivating, associating, or some other action) executed in connection with the particular item 21 and performed, at least in part, by the second authoring user 19, at least one systemic physiological characteristic (e.g., blood pressure) associated with the second authoring user 19.

In some implementations, the observation operation 604 may include an operation 612 for sensing, during or proximate to the action executed in connection with the particular item and performed, at least in part, by the second authoring user, at least one of galvanic skin response, heart rate, blood pressure, or respiration associated with the second authoring user as illustrated in FIG. 6a. For instance, the physical characteristic sensing module 108 of the authoring device 10 sensing (e.g., via a galvanic skin sensor device 144, a heart rate sensor device 145, a blood pressure sensor device 146, or a respiration sensor device 147), during or proximate to the action (e.g., forwarding, storing, tagging, or some other action) executed in connection with the particular item 21 and performed, at least in part, by the second authoring user 19, at least one of galvanic skin response, heart rate, blood pressure, or respiration associated with the second authoring user 19.

Figure 6B:
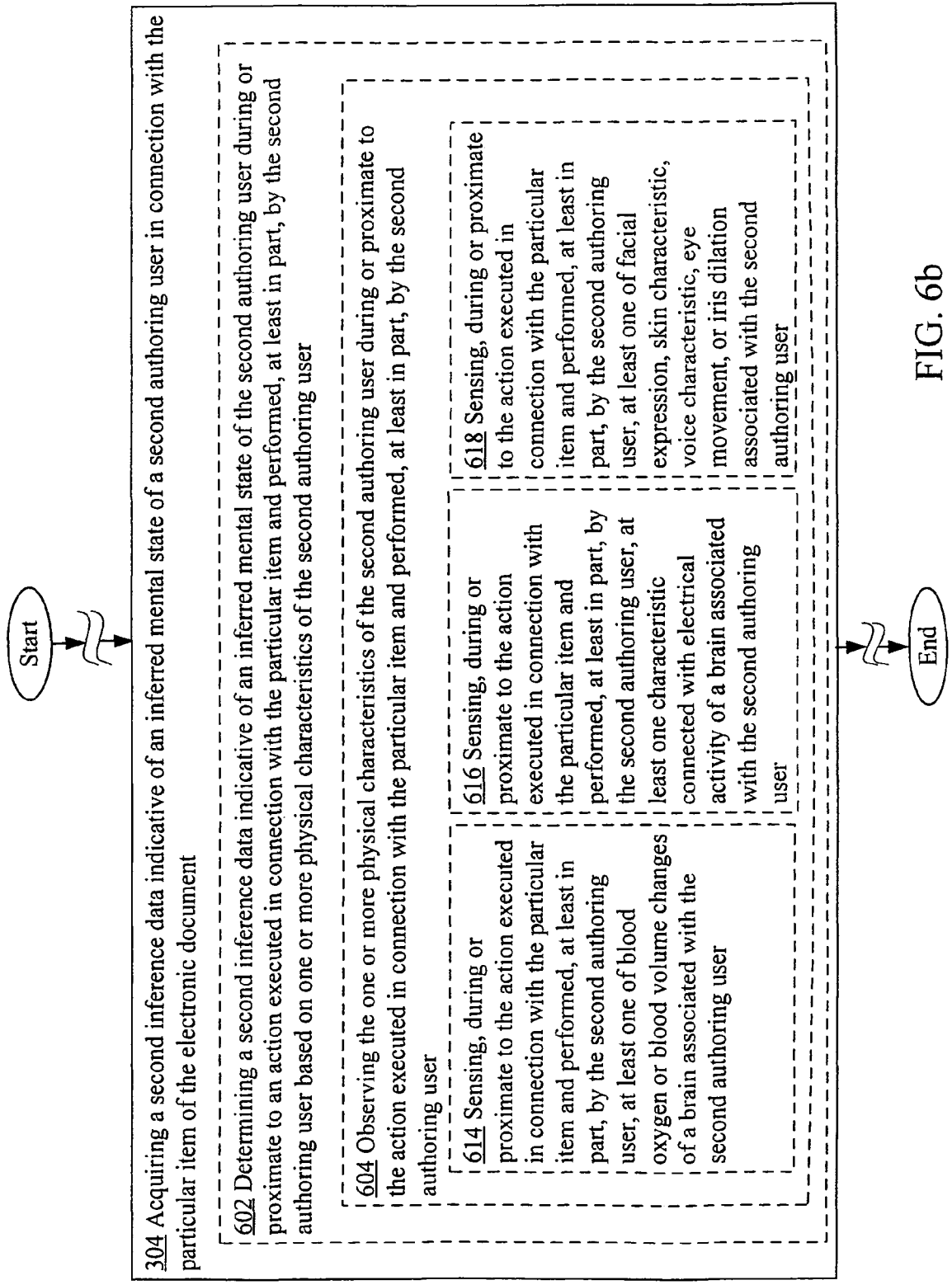

In some implementations, the observation operation 604 may include an operation 614 for sensing, during or proximate to the action executed in connection with the particular item and performed, at least in part, by the second authoring user, at least one of blood oxygen or blood volume changes of a brain associated with the second authoring user as illustrated in FIG. 6b. For instance, the physical characteristic sensing module 108 of the authoring device 10 sensing (e.g., via an fMRI device 140 or an fNIR device 141), during or proximate to the action (e.g., categorizing, substituting, inserting, or some other action) executed in connection with the particular item 21 and performed, at least in part, by the second authoring user 19, at least one of blood oxygen or blood volume changes of a brain associated with the second authoring user 19.

In some implementations, the observation operation 604 may include an operation 616 for sensing, during or proximate to the action executed in connection with the particular item and performed, at least in part, by the second authoring user, at least one characteristic connected with electrical activity of a brain associated with the second authoring user as illustrated in FIG. 6b. For instance, the physical characteristic sensing module 108 of the authoring device 10 sensing (e.g., via an EEG device 142 or an MEG device 143), during or proximate to the action (e.g., creating, modifying, deleting, or some other action) executed in connection with the particular item 21 and performed, at least in part, by the second authoring user 19, at least one characteristic connected with electrical activity of a brain associated with the second authoring user 19.

In some implementations, the observation operation 604 may include an operation 618 for sensing, during or proximate to the action executed in connection with the particular item and performed, at least in part, by the second authoring user, at least one of facial expression, skin characteristic, voice characteristic, eye movement, or iris dilation associated with the second authoring user as illustrated in FIG. 6b. For instance, the physical characteristic sensing module 108 of the authoring device 10 sensing (e.g., via a facial expression sensor device 148, a skin characteristic sensor device 149, a voice response device 150, gaze tracking device 151, or an iris response device 152), during or proximate to the action (e.g., relocating, extracting, activating, deactivating, associating, or some other action) executed in connection with the particular item 21 and performed, at least in part, by the second authoring user 19, at least one of facial expression, skin characteristic, voice characteristic, eye movement, or iris dilation associated with the second authoring user 19.

Figure 6C:
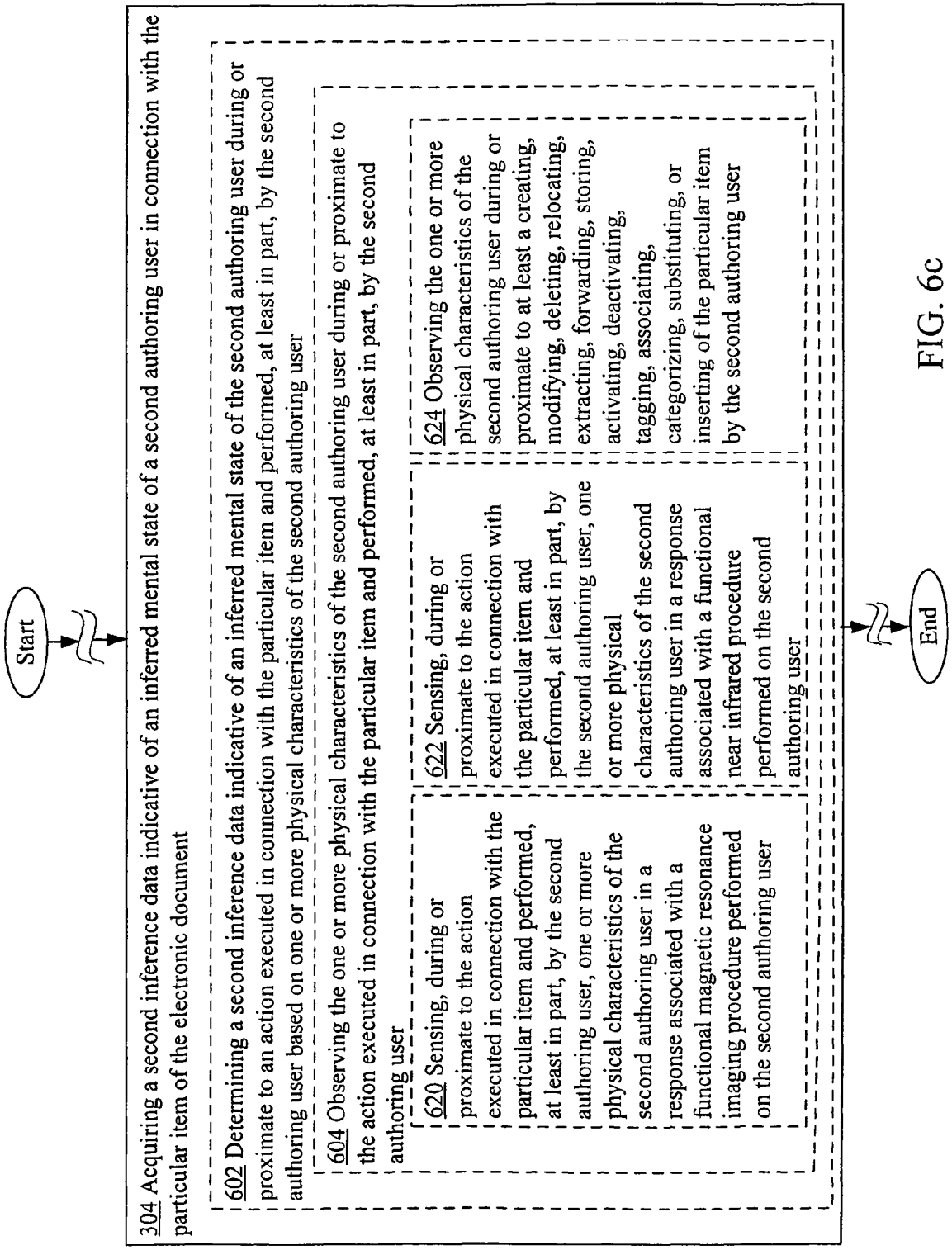

In some implementations, the observation operation 604 may include an operation 620 for sensing, during or proximate to the action executed in connection with the particular item and performed, at least in part, by the second authoring user, one or more physical characteristics of the second authoring user in a response associated with a functional magnetic resonance imaging procedure performed on the second authoring user as illustrated in FIG. 6c. For instance, the physical characteristic sensing module 108 of the authoring device 10 sensing (e.g., via an fMRI device 140), during or proximate to the action (e.g., forwarding, storing, tagging, or some other action) executed in connection with the particular item 21 and performed, at least in part, by the second authoring user 19, one or more physical characteristics (e.g., cerebral characteristics) of the second authoring user 19 in a response associated with a functional magnetic resonance imaging procedure performed on the second authoring user 19.

In some implementations, the observation operation 604 may include an operation 622 for sensing, during or proximate to the action executed in connection with the particular item and performed, at least in part, by the second authoring user, one or more physical characteristics of the second authoring user in a response associated with a functional near infrared procedure performed on the second authoring user as illustrated in FIG. 6c. For instance, the physical characteristic sensing module 108 of the authoring device 10 sensing (e.g., via an fNIR device 141), during or proximate to the action (e.g., categorizing, substituting, inserting, or some other action) executed in connection with the particular item 21 and performed, at least in part, by the second authoring user 19, one or more physical characteristics (e.g., cerebral characteristics) of the second authoring user 19 in a response associated with a functional near infrared procedure performed on the second authoring user 19.

In some implementations, the observation operation 604 may include an operation 624 for observing the one or more physical characteristics of the second authoring user during or proximate to at least a creating, modifying, deleting, relocating, extracting, forwarding, storing, activating, deactivating, tagging, associating, categorizing, substituting, or inserting of the particular item by the second authoring user as illustrated in FIG. 6c. For instance, the physical characteristic observation module 104 of the authoring device 10 observing (e.g., via the physical characteristic observation module 104) the one or more physical characteristics (e.g., one or more of cerebral, cardiopulmonary, and/or systemic physiological characteristics) of the second authoring user 19 during or proximate to at least a creating, modifying, deleting, relocating, extracting, forwarding, storing, activating, deactivating, tagging, associating, categorizing, substituting, or inserting of the particular item 21 by the second authoring user 19.

In the same or alternative implementations, the observation of the one or more physical characteristics of the second authoring user 19 may occur during or proximate to other types of actions (which may be indirectly connected to the particular item 21) other than those described above (e.g., creating, deleting, modifying, and so forth). For instance, in some alternative implementations, the observation of the one or more physical characteristics of the second authoring user 19 may occur during or proximate to a searching operation (e.g., in order to find particular information) initiated by the second authoring user 19 and that may have been prompted while accessing the particular item 21.

Figure 6D:
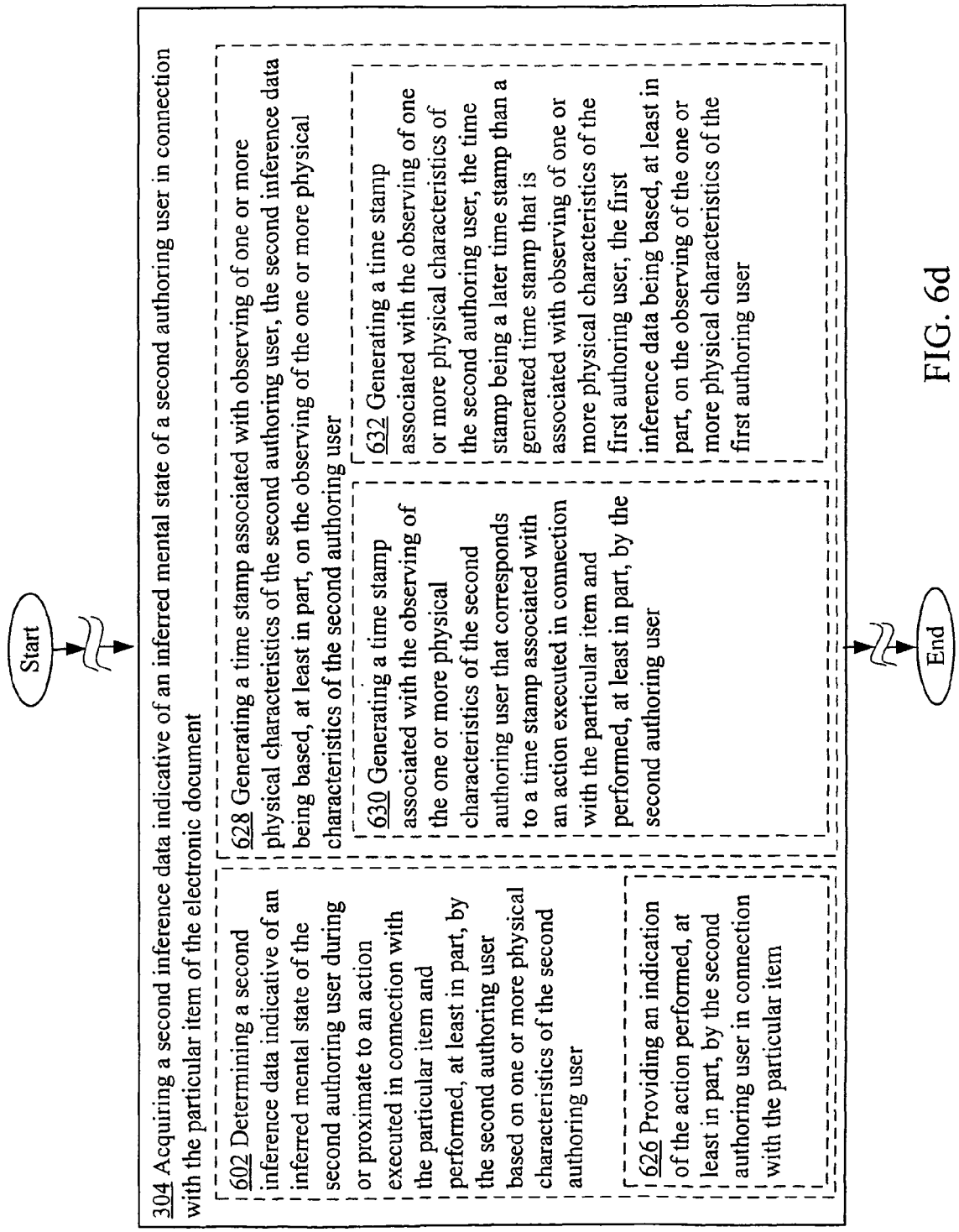
FIG. 6d is a high-level logic flowchart of a process depicting more alternate implementations of the second inference data acquisition operation 304 of FIG. 3.

In various implementations, the determination operation 602 of FIG. 6a may include an operation 626 for providing an indication of the action performed, at least in part, by the second authoring user in connection with the particular item as illustrated in FIG. 6d. For instance, the action module 34 of the authoring device 10 providing an indication (e.g., name or symbolic representation) of the action (e.g., creating, modifying, deleting, relocating, extracting, forwarding, storing, activating, deactivating, tagging, associating, categorizing, substituting, or inserting) performed, at least in part, by the second authoring user 19 in connection with the particular item 21.

In various implementations, the second inference acquisition operation 304 of FIG. 3 may include an operation 628 for generating a time stamp associated with observing of one or more physical characteristics of the second authoring user, the second inference data being based, at least in part, on the observing of the one or more physical characteristics of the second authoring user as illustrated in FIG. 6d. For instance, the time stamp module 125 (see FIG. 2j) of the authoring device 10 generating a time stamp associated with observing (e.g., via an fMRI device 140, an fNIR device 141, an EEG device 142, and/or an MEG device 143) of one or more physical characteristics (e.g., cerebral characteristics) of the second authoring user 19, the second inference data being based, at least in part, on the observing of the one or more physical characteristics of the second authoring user 19.

In some implementations, operation 628 may further include an operation 630 for generating a time stamp associated with the observing of the one or more physical characteristics of the second authoring user that corresponds to a time stamp associated with an action executed in connection with the particular item and performed, at least in part, by the second authoring user as illustrated in FIG. 6d. For instance, the time stamp module 125 of the authoring device 10 generating a time stamp associated with the observing of the one or more physical characteristics of the second authoring user 19 that corresponds to a time stamp associated with an action (e.g., creating, modifying, deleting, or some other action) executed in connection with the particular item 21 and performed, at least in part, by the second authoring user 19.

In some implementations, operation 628 may include an operation 632 for generating a time stamp associated with the observing of one or more physical characteristics of the second authoring user, the time stamp being a later time stamp than a generated time stamp that is associated with observing of one or more physical characteristics of the first authoring user, the first inference data being based, at least in part, on the observing of the one or more physical characteristics of the first authoring user as illustrated in FIG. 6d. For instance, the time stamp module 125 of the authoring device 10 generating a time stamp associated with the observing (e.g., via an fMRI device 140, an fNIR device 141, an EEG device 142, and/or an MEG device 143) of one or more physical characteristics (e.g., cerebral characteristics) of the second authoring user 19, the time stamp being a later time stamp than a generated time stamp that is associated with observing (e.g., via an fMRI device 140, an fNIR device 141, an EEG device 142, and/or an MEG device 143) of one or more physical characteristics (e.g., cerebral characteristics) of the first authoring user 18, the first inference data being based, at least in part, on the observing of the one or more physical characteristics of the first authoring user 18.

In various implementations, the second inference acquisition operation 304 of FIG. 3 may include an inference operation 634 for inferring a mental state of the second authoring user based, at least in part, on an observation made of one or more physical characteristics of the second authoring user during or proximate to an action executed in connection with the particular item and performed, at least in part, by the second authoring user as illustrated in FIG. 6e. For instance, the mental state inference module 211 (see FIG. 2b) of the authoring device 10 inferring (e.g., determining or deriving) a mental state of the second authoring user 19 based, at least in part, on an observation made (e.g., via a galvanic skin sensor device 144, a heart rate sensor device 145, a blood pressure sensor device 146, a respiration sensor device 147, a facial expression sensor device 148, a skin characteristics sensor device 149, a voice response device 150, a gaze tracking device 151, or an iris response device 152) of one or more physical characteristics (e.g., cardiopulmonary characteristics, systemic physiological characteristics, or some other characteristics) of the second authoring user 19 during or proximate to an action (e.g., creating, modifying, or deleting) executed in connection with the particular item 21 and performed, at least in part, by the second authoring user 19.

In various implementations, the inference operation 634 may further include one or more additional operations. For example, in some implementations, the inference operation 634 may include an operation 636 for inferring a mental state of the second authoring user indicating that the second authoring user was in at least one of a state of anger, a state of distress, or a state of pain during or proximate to the action executed in connection with the particular item and performed, at least in part, by the second authoring user as illustrated in FIG. 6e. For instance, the mental state inference module 211 of the authoring device 10 inferring (e.g., determining or deriving based on data provided by an fMRI device 140, an fNIR device 141, an EEG device 142, an MEG device 143, and/or some other sensor) a mental state of the second authoring user 19 indicating that the second authoring user 19 was in at least one of a state of anger, a state of distress, or a state of pain during or proximate to the action (e.g., relocating, extracting, activating, deactivating, associating, or some other action) executed in connection with the particular item 21 and performed, at least in part, by the second authoring user 19.

In some implementations, the inference operation 634 may include an operation 638 for inferring a mental state of the second authoring user indicating that the second authoring user was in at least one of a state of frustration, a state of approval or disapproval, a state of trust, a state of fear, a state of happiness, a state of surprise, a state of inattention, a state of arousal, a state of impatience, a state of confusion, a state of distraction, a state of overall mental activity, a state of alertness, or a state of acuity during or proximate to the action executed in connection with the particular item and performed, at least in part, by the second authoring user as illustrated in FIG. 6e. For instance, the mental state inference module 211 of the authoring device 10 inferring (e.g., determining or deriving based on data provided by a galvanic skin sensor device 144, a heart rate sensor device 145, a blood pressure sensor device 146, a respiration sensor device 147, a facial expression sensor device 148, a skin characteristic sensor device 149, a voice response device 150, a gaze tracking device 151, an iris response device 152, and/or some other sensor) a mental state of the second authoring user 19 indicating that the second authoring user 19 was in at least one of a state of frustration, a state of approval or disapproval, a state of trust, a state of fear, a state of happiness, a state of surprise, a state of inattention, a state of arousal, a state of impatience, a state of confusion, a state of distraction, a state of overall mental activity, a state of alertness, or a state of acuity during or proximate to the action (e.g., forwarding, storing, tagging, or some other action) executed in connection with the particular item 21 and performed, at least in part, by the second authoring user 19.

Figure 7B:
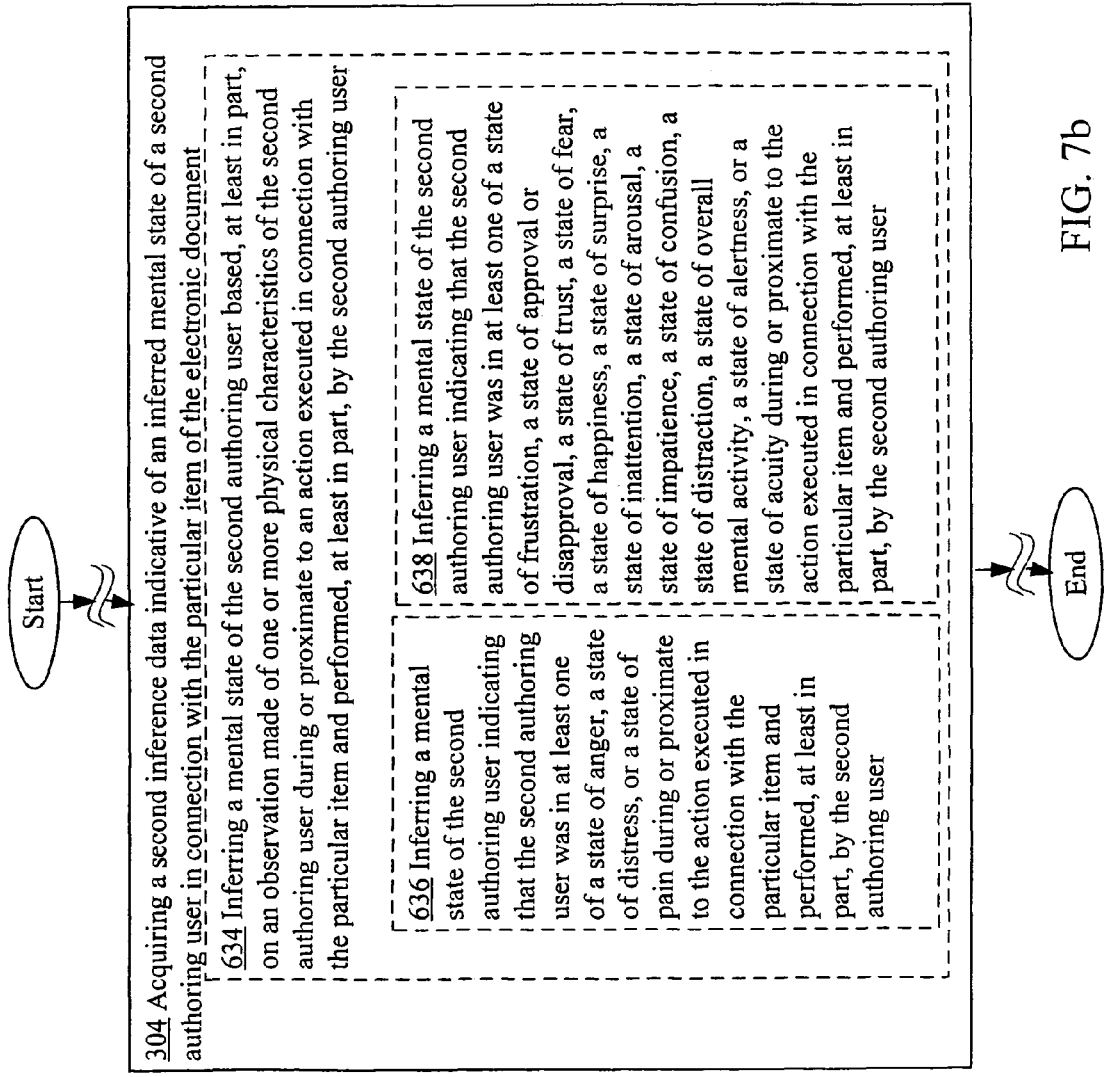
FIG. 7 is a high-level logic flowchart of a process depicting alternate implementations of the comparison operation 306 of FIG. 3.

In various implementations, the comparison operation 306 of FIG. 3 may include at least one additional operation as illustrated in FIG. 7. For example, in some implementations, the comparison operation 306 may include an operation 702 for determining an extent of a difference between the inferred mental state of the first authoring user and the inferred mental state of the second authoring user as illustrated in FIG. 7. For instance, the mental state difference determination module 210 (see FIG. 2c) of the authoring device 10 determining an extent of a difference between the inferred mental state (e.g., as provided by the mental state inference module 211) of the first authoring user 18 and the inferred mental state (e.g., as provided by the mental state inference module 211) of the second authoring user 19.

Figure 8A:
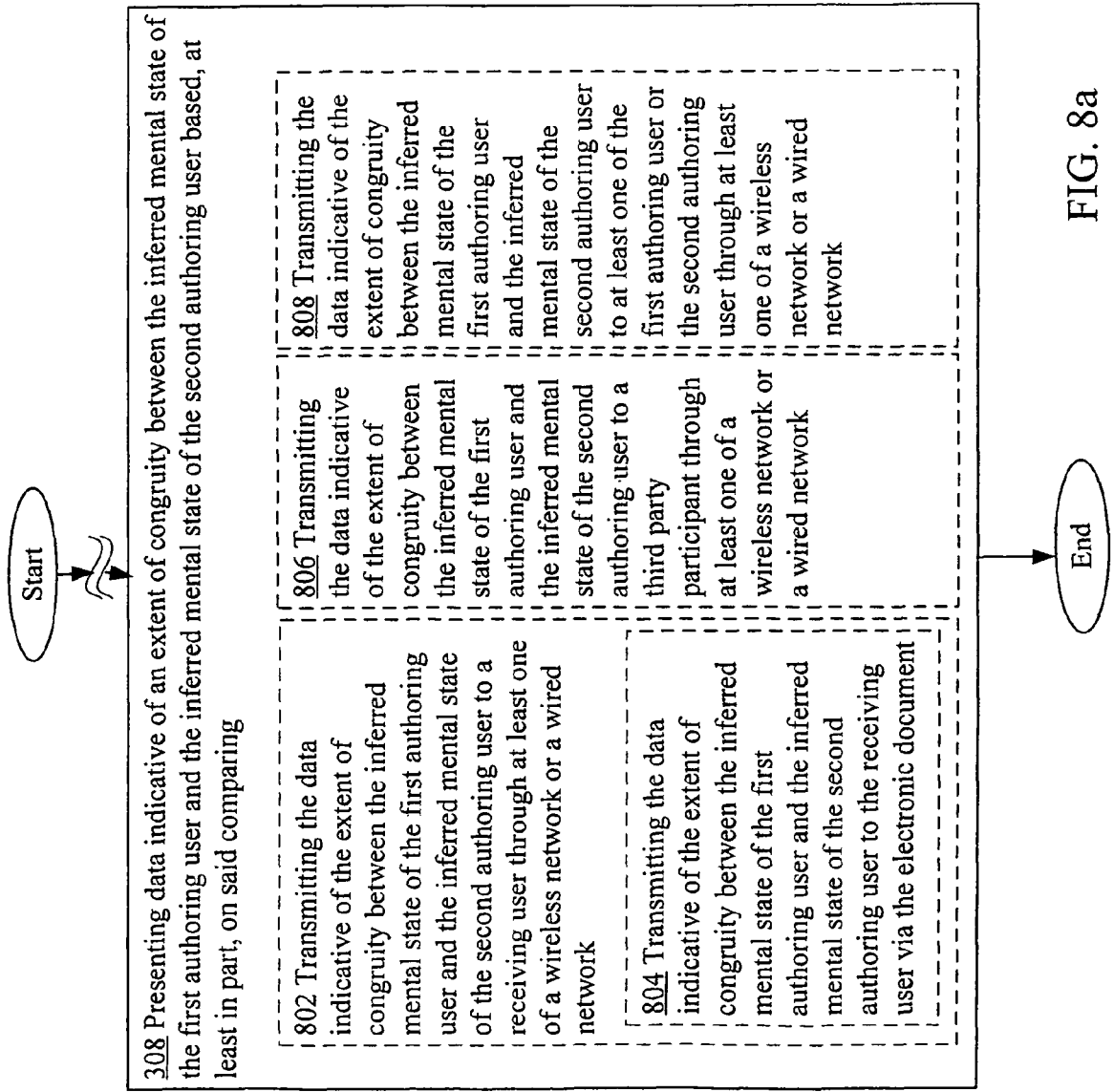
FIG. 8a is a high-level logic flowchart of a process depicting alternate implementations of the presentation operation 308 of FIG. 3.

Referring back to FIG. 3, in various alternative implementations, the presentation operation 308 may include one or more additional operations. For example, in some implementations, the presentation operation 308 may include an operation 802 for transmitting the data indicative of the extent of congruity between the inferred mental state of the first authoring user and the inferred mental state of the second authoring user to a receiving user through at least one of a wireless network or a wired network as illustrated in FIG. 8a. For instance, the transmission module 212 (see FIG. 2d) of the authoring device 10 transmitting (e.g., via the network communication interface 42) the data indicative of the extent of congruity between the inferred mental state of the first authoring user 18 and the inferred mental state of the second authoring user 18 to a receiving user 22 through at least one of a wireless network or a wired network 16. Such an operation may be carried out in some situations in order to inform the receiving user 22 the extent of congruence between the inferred mental states of multiple authoring users (e.g., the first authoring user 18 and the second authoring user 19) in connection with the particular item 21. In doing so, the receiving user 22 may be better facilitated in understanding the meaning and intent of the particular item 21, the receiving user 22 in this case being the intended recipient of the electronic document 20.

In some implementations, operation 802 may further include an operation 804 for transmitting the data indicative of the extent of congruity between the inferred mental state of the first authoring user and the inferred mental state of the second authoring user to the receiving user via the electronic document as illustrated in FIG. 8a. For instance, the transmission module 212 of the authoring device 10 transmitting (e.g., via the network communication interface 42) the data indicative of the extent of congruity between the inferred mental state of the first authoring user 18 and the inferred mental state of the second authoring user 19 to the receiving user 22 via the electronic document 20 (e.g., including the data into the electronic document 20).

In some implementations, the presentation operation 308 may include an operation 806 for transmitting the data indicative of the extent of congruity between the inferred mental state of the first authoring user and the inferred mental state of the second authoring user to a third party participant through at least one of a wireless network or a wired network as illustrated in FIG. 8a. For instance, the transmission module 212 of the authoring device 10 transmitting (e.g., via the network communication interface 42) the data indicative of the extent of congruity between the inferred mental state of the first authoring user 18 and the inferred mental state of the second authoring user 19 to a third party participant through at least one of a wireless network or a wired network 16.

In some implementations, the presentation operation 308 may include an operation 808 for transmitting the data indicative of the extent of congruity between the inferred mental state of the first authoring user and the inferred mental state of the second authoring user to at least one of the first authoring user or the second authoring user through at least one of a wireless network or a wired network as illustrated in FIG. 8a. For instance, the transmission module 212 of the authoring device 10 transmitting (e.g., via the network communication interface 42) the data indicative of the extent of congruity between the inferred mental state of the first authoring user 18 and the inferred mental state of the second authoring user 19 to at least one of the first authoring user 18 (e.g., via remote network device 50) or the second authoring user 19 (e.g., via remote network device 51) through at least one of a wireless network or a wired network 16. Such an operation may be carried out in some situations in order to inform an authoring user (e.g., first authoring user 18) whether his/her inferred mental state is in congruence or not in congruence with the inferred mental state of the other authoring user (e.g., second authoring user 19) in connection with the particular item 21.

Figure 8B:
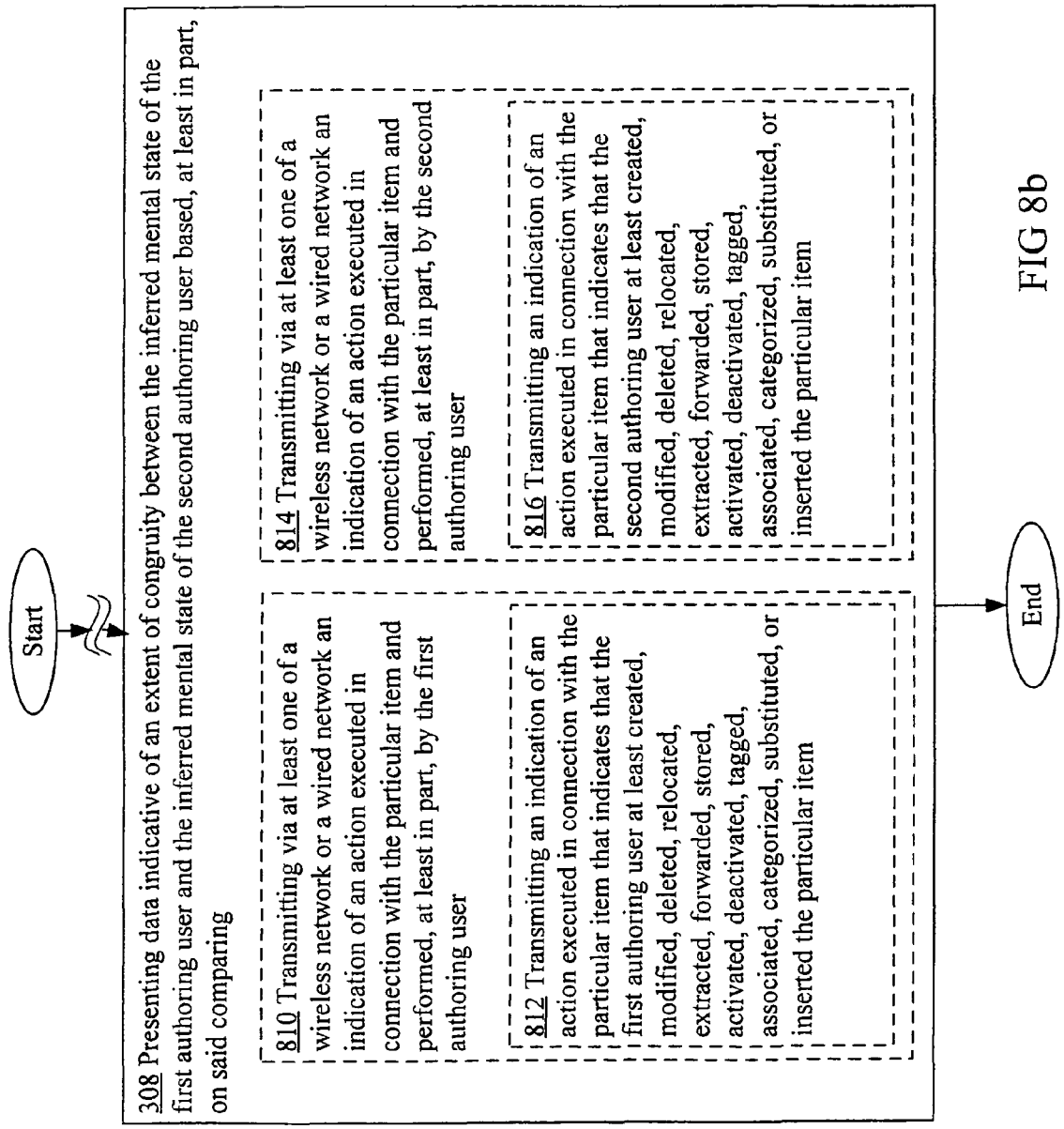
FIG. 8b is a high-level logic flowchart of a process depicting more alternate implementations of the presentation operation 308 of FIG. 3.

In some implementations, the presentation operation 308 may include an operation 810 for transmitting via at least one of a wireless network or a wired network an indication of an action executed in connection with the particular item and performed, at least in part, by the first authoring user as illustrated in FIG. 8b. For instance, the transmission module 212 of the authoring device 10 transmitting via at least one of a wireless network or a wired network 16 an indication of an action (e.g., creating, modifying, deleting, or some other action) executed in connection with the particular item 21 and performed, at least in part, by the first authoring user 18.

Operation 810, in various implementations, may further include an operation 812 for transmitting an indication of an action executed in connection with the particular item that indicates that the first authoring user at least created, modified, deleted, relocated, extracted, forwarded, stored, activated, deactivated, tagged, associated, categorized, substituted, or inserted the particular item as illustrated in FIG. 8b. For instance, the transmission module 212 of the authoring device 10 transmitting (e.g., via the network communication interface 42) an indication of an action executed (e.g., via sub-modules of action module 34) in connection with the particular item 21 that indicates that the first authoring user 18 at least created, modified, deleted, relocated, extracted, forwarded, stored, activated, deactivated, tagged, associated, categorized, substituted, or inserted the particular item 21.

In some implementations, the presentation operation 308 may also include an operation 814 for transmitting via at least one of a wireless network or a wired network an indication of an action executed in connection with the particular item and performed, at least in part, by the second authoring user as illustrated in FIG. 8b. For instance, the transmission module 212 of the authoring device 10 transmitting via at least one of a wireless network or a wired network 16 an indication of an action (e.g., creating, modifying, deleting, or some other action) executed in connection with the particular item 21 and performed, at least in part, by the second authoring user 19.

Operation 814, in various implementations, may further include an operation 816 for transmitting an indication of an action executed in connection with the particular item that indicates that the second authoring user at least created, modified, deleted, relocated, extracted, forwarded, stored, activated, deactivated, tagged, associated, categorized, substituted, or inserted the particular item as illustrated in FIG. 8b. For instance, the transmission module 212 of the authoring device 10 transmitting (e.g., via the network communication interface 42) an indication of an action executed in connection with the particular item 21 that indicates that the second authoring user 19 at least created, modified, deleted, relocated, extracted, forwarded, stored, activated, deactivated, tagged, associated, categorized, substituted, or inserted the particular item 21.

Figure 8C:
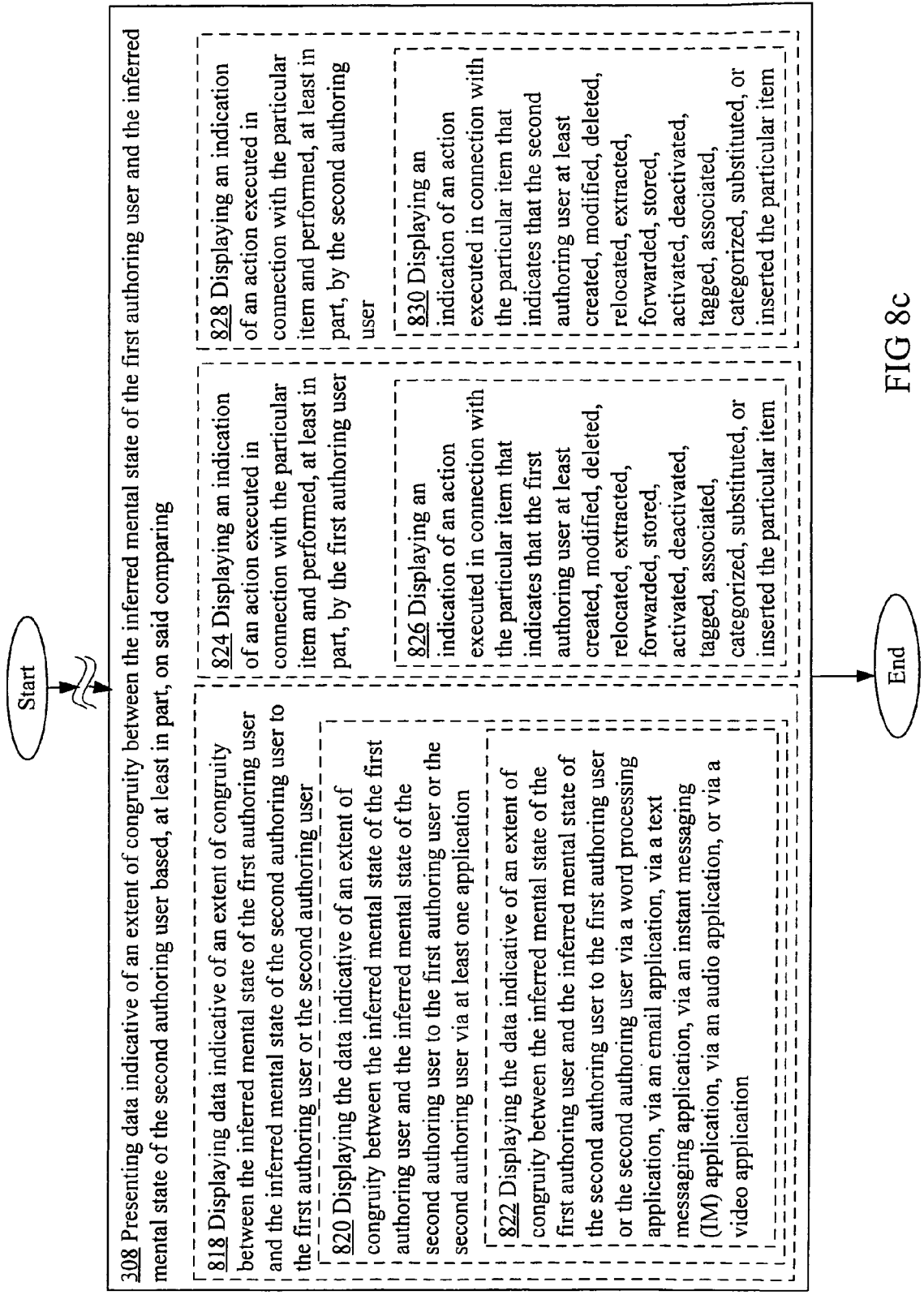
FIG. 8c is a high-level logic flowchart of a process depicting more alternate implementations of the presentation operation 308 of FIG. 3.

In some implementations, the presentation operation 308 may include an operation 818 for displaying data indicative of an extent of congruity between the inferred mental state of the first authoring user and the inferred mental state of the second authoring user to the first authoring user or the second authoring user as illustrated in FIG. 8c. For instance, the display module 213 of the authoring device 10 displaying (e.g., via the user interface 44 including, for example, a display monitor 130 and/or a speaker system 135) data indicative of an extent of congruity between the inferred mental state of the first authoring user 18 and the inferred mental state of the second authoring user 19 to the first authoring user 18 or the second authoring user 19. Note that the term "displaying" as used herein may be broadly construed to refer to any one or more of a wide range of approaches that may be employed in order to show the "congruity" data (e.g., data indicative of an extent of congruity between the inferred mental state of the first authoring user 18 and the inferred mental state of the second authoring user 19). For example, in some implementations, the congruity data may be "displayed" or "shown" via a speaker system 135 rather than through some display system (e.g., display monitor 130 or a printer 137). That is, such congruity data can be indicated by a visual display, a combination of a visual display and audio, a particular sound, or an audio message.

Operation 818, in various implementations, may further include an operation 820 for displaying the data indicative of an extent of congruity between the inferred mental state of the first authoring user and the inferred mental state of the second authoring user to the first authoring user or the second authoring user via at least one application as illustrated in FIG. 8c. For instance, the display module 213 of the authoring device 10 displaying (e.g., via the user interface 44 including, for example, an user touch screen 131) the data indicative of an extent of congruity between the inferred mental state of the first authoring user 18 and the inferred mental state of the second authoring user 19 to the first authoring user 18 or the second authoring user 19 via at least one application (e.g., word processing application 240).

In some implementations, operation 820 may further include an operation 822 for displaying the data indicative of an extent of congruity between the inferred mental state of the first authoring user and the inferred mental state of the second authoring user to the first authoring user or the second authoring user via a word processing application, via an email application, via a text messaging application, via an instant messaging (IM) application, via an audio application, or via a video application as illustrated in FIG. 8c. For instance, the display module 213 of the authoring device 10 displaying (e.g., via the user interface 44 including, for example, a display monitor 130) the data indicative of an extent of congruity between the inferred mental state of the first authoring user 18 and the inferred mental state of the second authoring user 19 to the first authoring user 18 or the second authoring user 19 via a word processing application 240, via an email application 242, via a text messaging application 244, via an instant messaging (IM) application 246, via an audio application 248, or via a video application 249.

The presentation operation 308 in various alternative implementations may also include an operation 824 for displaying an indication of an action executed in connection with the particular item and performed, at least in part, by the first authoring user as illustrated in FIG. 8c. For instance, the display module 213 of the authoring device 10 displaying (e.g., via the user interface 44 including, for example, a display monitor 130) an indication of an action (e.g., creating, modifying, deleting, or some other action) executed in connection with the particular item 21 and performed, at least in part, by the first authoring user 18.

In various implementations, operation 824 may further include an operation 826 for displaying an indication of an action executed in connection with the particular item that indicates that the first authoring user at least created, modified, deleted, relocated, extracted, forwarded, stored, activated, deactivated, tagged, associated, categorized, substituted, or inserted the particular item as illustrated in FIG. 8c. For instance, the display module 213 of the authoring device 10 displaying (e.g., via the user interface 44 including, for example, a printer 137) an indication of an action executed in connection with the particular item 21 that indicates that the first authoring user 18 at least created, modified, deleted, relocated, extracted, forwarded, stored, activated, deactivated, tagged, associated, categorized, substituted, or inserted the particular item 21.

In various implementations, the presentation operation 308 may also include an operation 828 for displaying an indication of an action executed in connection with the particular item and performed, at least in part, by the second authoring user as illustrated in FIG. 8c. For instance, the display module 213 of the authoring device 10 displaying (e.g., via the user interface 44 including, for example, a display monitor 130) an indication of an action (e.g., creating, modifying, deleting, or some other action) executed in connection with the particular item 21 and performed, at least in part, by the second authoring user 19.

In some implementations, operation 828 may further include an operation 830 for displaying an indication of an action executed in connection with the particular item that indicates that the second authoring user at least created, modified, deleted, relocated, extracted, forwarded, stored, activated, deactivated, tagged, associated, categorized, substituted, or inserted the particular item as illustrated in FIG. 8c. For instance, the display module 213 of the authoring device 10 displaying (e.g., via the user interface 44 including, for example, an user touch screen 131) an indication of an action executed in connection with the particular item 21 that indicates that the second authoring user 19 at least created, modified, deleted, relocated, extracted, forwarded, stored, activated, deactivated, tagged, associated, categorized, substituted, or inserted the particular item 21.

Figure 8D:
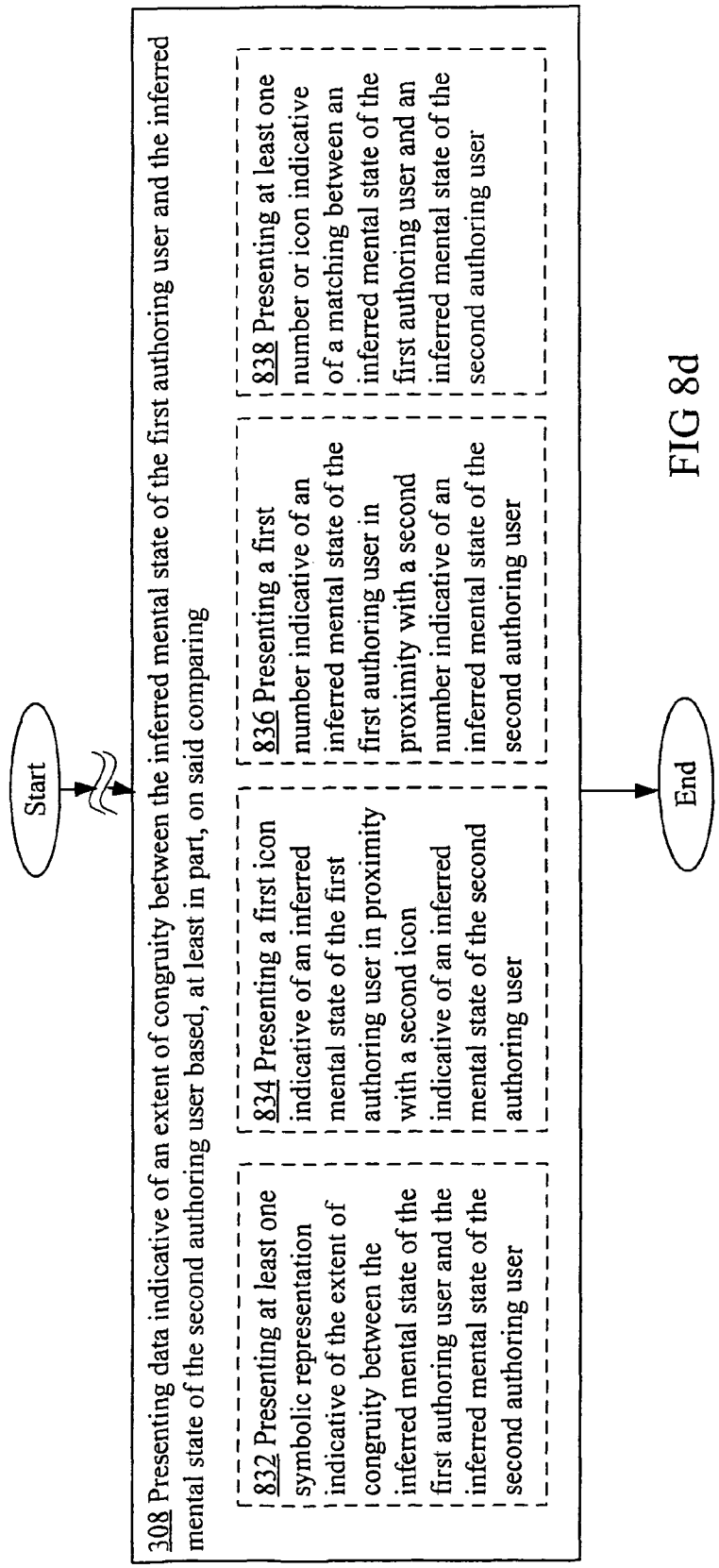
FIG. 8d is a high-level logic flowchart of a process depicting more alternate implementations of the presentation operation 308 of FIG. 3.

The presentation operation 308 of FIG. 3 may, in various implementations, include an operation 832 for presenting at least one symbolic representation indicative of the extent of congruity between the inferred mental state of the first authoring user and the inferred mental state of the second authoring user as illustrated in FIG. 8*d*. For instance, the presentation module 38 of the authoring device 10 presenting (e.g., via the display module 213 using the user interface 44 and/or via the transmission module 212 using the network communication interface 42) at least one symbolic representation (e.g., icon, number, word, phrase, and so forth) that indicates or represents the extent of congruity between the inferred mental state (e.g., state of happiness) of the first authoring user 18 and the inferred mental state (e.g., state of anger) of the second authoring user 19.

In some implementations, the presentation operation 308 may include an operation 834 for presenting a first icon indicative of an inferred mental state of the first authoring user in proximity with a second icon indicative of an inferred mental state of the second authoring user as illustrated in FIG. 8*d*. For instance, the presentation module 38 of the authoring device 10 presenting (e.g., via the display module 213 using the user interface 44 and/or via the transmission module 212 using the network communication interface 42) a first icon (e.g., a first emoticon) that indicates or represents an inferred mental state (e.g., state of distress) of the first authoring user 18 in proximity with a second icon (e.g., a second emoticon) indicates or represents an inferred mental state (e.g., state of frustration) of the second authoring user 19.

In some implementations, the presentation operation 308 may include an operation 836 for presenting a first number indicative of an inferred mental state of the first authoring user in proximity with a second number indicative of an inferred mental state of the second authoring user as illustrated in FIG. 8*d*. For instance, the presentation module 38 of the authoring device 10 presenting (e.g., via the display module 213 using the user interface 44 and/or via the transmission module 212 using the network communication interface 42) a first number that indicates or represents an inferred mental state (e.g., state of anger) of the first authoring user 18 in proximity with a second number that indicates or represents an inferred mental state (e.g., state of frustration) of the second authoring user 19.

In some implementations, the presentation operation 308 may include an operation 838 for presenting at least one number or icon indicative of a matching between an inferred mental state of the first authoring user and an inferred mental state of the second authoring user as illustrated in FIG. 8*d*. For instance, the presentation module 38 of the authoring device 10 presenting (e.g., via the display module 213 using the user interface 44 and/or via the transmission module 212 using the network communication interface 42) at least one number or icon that indicates or represents a matching between an inferred mental state (e.g., state of happiness) of the first authoring user 18 and an inferred mental state (e.g., state of happiness) of the second authoring user 19.

Figure 8E:
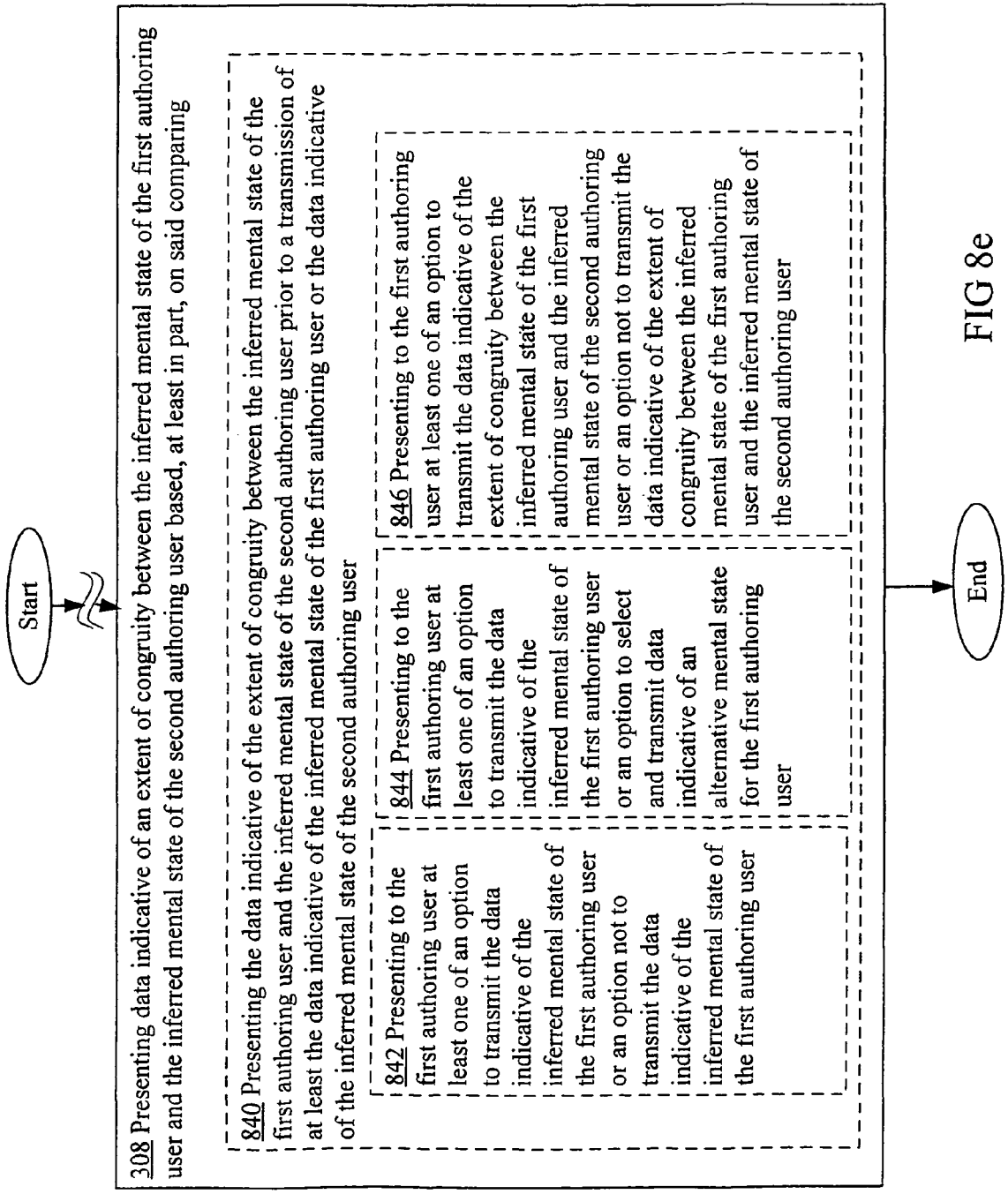
FIG. 8e is a high-level logic flowchart of a process depicting more alternate implementations of the presentation operation 308 of FIG. 3.

In some implementations, the presentation operation 308 may include an operation 840 for presenting the data indicative of the extent of congruity between the inferred mental state of the first authoring user and the inferred mental state of the second authoring user prior to a transmission of at least the data indicative of the inferred mental state of the first authoring user or the data indicative of the inferred mental state of the second authoring user as illustrated in FIG. 8*e*. For instance, the presentation module 38 of the authoring device 10 presenting (e.g., via the display module 213 using the user interface 44 and/or via the transmission module 212 using the network communication interface 42) the data indicative of the extent of congruity between the inferred mental state (e.g., state of approval) of the first authoring user 18 and the inferred mental state (e.g., state of disapproval) of the second authoring user 19 prior to a transmission (e.g., via the network communication interface 42 to the receiving user 22) of at least the data indicative of the inferred mental state (e.g., state of approval) of the first authoring user 18 or the data indicative of the inferred mental state (e.g., state of disapproval) of the second authoring user 19.

In various implementations, operation 840 may include one or more additional operations. For instance, in some implementations, operation 840 may include an operation 842 for presenting to the first authoring user at least one of an option to transmit the data indicative of the inferred mental state of the first authoring user or an option not to transmit the data indicative of the inferred mental state of the first authoring user as illustrated in FIG. 8*e*. For instance, the presentation module 38 of the authoring device 10 presenting (e.g., via the display module 213 using the user interface 44 and/or via the transmission module 212 using the network communication interface 42) to the first authoring user 18 at least one of an option to transmit (e.g., to send to a receiving user 22 or a third party user via the network communication interface 42) the data indicative of the inferred mental state (e.g., state of fear) of the first authoring user 18 or an option not to transmit the data indicative of the inferred mental state (e.g., state of fear) of the first authoring user 18.

In some implementations, operation 840 may include an operation 844 for presenting to the first authoring user at least one of an option to transmit the data indicative of the inferred mental state of the first authoring user or an option to select and transmit data indicative of an alternative mental state for the first authoring user as illustrated in FIG. 8*e*. For instance, the presentation module 38 of the authoring device 10 presenting (e.g., via the display module 213 using the user interface 44 and/or via the transmission module 212 using the network communication interface 42) to the first authoring user 18 at least one of an option to transmit (e.g., to send to a receiving user 22 or a third party user via the network communication interface 42) the data indicative of the inferred mental state (e.g., state of frustration) of the first authoring user 18 or an option to select and transmit data indicative of an alternative mental state (e.g., state of surprise) for the first authoring user 18. Such an operation may be provided in some instances in order to, for example, allow the first authoring user 18 to change the data indicating the inferred mental state of the first authoring user 18 prior to the transmission (e.g., to the receiving user 22 or a third party participant) of such data. For example, if the first authoring user 18 believes that the data indicative of the inferred mental state of the first authoring user 18 derived from the observations made by the one or more sensors 48 indicates an incorrect inferred mental state for the first authoring user 18 or wishes to disguise the mental state of the first authoring user 18, then such an operation may provide an option for the first authoring user 18 to select and transmit data that indicates an alternative mental state for the first authoring user 18.

In some implementations, operation 840 may include an operation 846 for presenting to the first authoring user at least one of an option to transmit the data indicative of the extent of congruity between the inferred mental state of the first authoring user and the inferred mental state of the second authoring user or an option not to transmit the data indicative of the extent of congruity between the inferred mental state of the first authoring user and the inferred mental state of the second authoring user as illustrated in FIG. 8e. For instance, the presentation module 38 of the authoring device 10 presenting (e.g., via the display module 213 using the user interface 44 and/or via the transmission module 212 using the network communication interface 42) to the first authoring user 18 at least one of an option to transmit (e.g., to send to a receiving user 22 or a third party participant via the network communication interface 42) the data indicative of the extent of congruity between the inferred mental state (e.g., state of happiness) of the first authoring user 18 and the inferred mental state (e.g., state of frustration) of the second authoring user 19 or an option not to transmit the data indicative of the extent of congruity between the inferred mental state (e.g., state of happiness) of the first authoring user 18 and the inferred mental state (e.g., state of frustration) of the second authoring user 19.

Figure 8F:
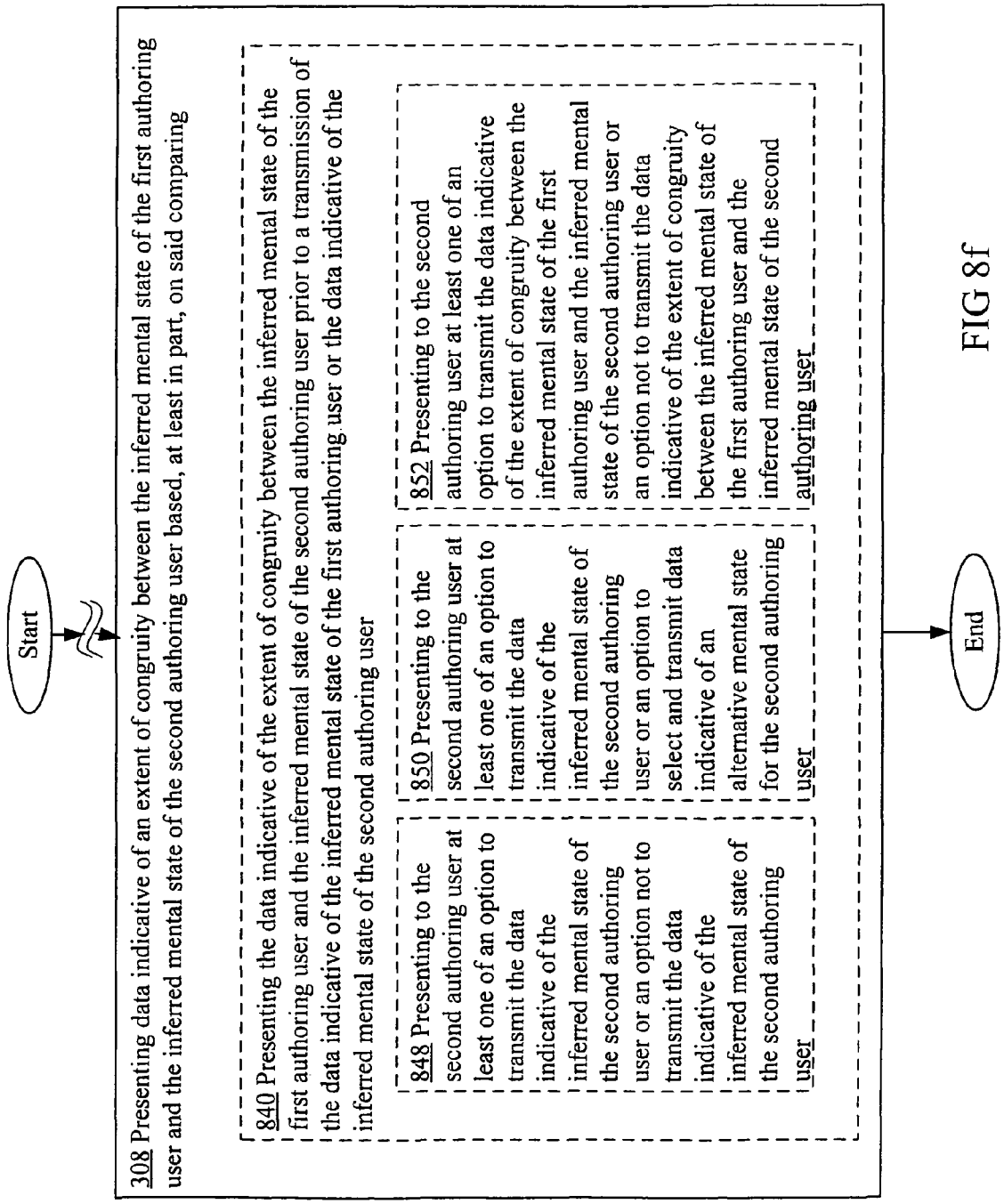
FIG. 8f is a high-level logic flowchart of a process depicting more alternate implementations of the presentation operation 308 of FIG. 3.

In some implementations, operation 840 may include an operation 848 for presenting to the second authoring user at least one of an option to transmit the data indicative of the inferred mental state of the second authoring user or an option not to transmit the data indicative of the inferred mental state of the second authoring user as illustrated in FIG. 8f. For instance, the presentation module 38 of the authoring device 10 presenting (e.g., via the display module 213 using the user interface 44 and/or via the transmission module 212 using the network communication interface 42) to the second authoring user 19 at least one of an option to transmit (e.g., to send to a receiving user 22 or a third party user via the network communication interface 42) the data indicative of the inferred mental state (e.g., state of surprise) of the second authoring user 19 or an option not to transmit the data indicative of the inferred mental state (e.g., state of surprise) of the second authoring user 19.

In some implementations, operation 840 may include an operation 850 for presenting to the second authoring user at least one of an option to transmit the data indicative of the inferred mental state of the second authoring user or an option to select and transmit data indicative of an alternative mental state for the second authoring user as illustrated in FIG. 8f. For instance, the presentation module 38 of the authoring device 10 presenting (e.g., via the display module 213 using the user interface 44 and/or via the transmission module 212 using the network communication interface 42) to the second authoring user 19 at least one of an option to transmit (e.g., to send to a receiving user 22 or a third party participant via the network communication interface 42) the data indicative of the inferred mental state (e.g., state of disapproval) of the second authoring user 19 or an option to select and transmit data indicative of an alternative mental state (e.g., state of approval) for the second authoring user 19. Such an operation may be provided in some instances in order to, for example, allow the second authoring user 19 to change the data indicating the inferred mental state of the second authoring user 19 prior to the transmission (e.g., to the receiving user 22 or a third party participant) of such data. For example, if the second authoring user 19 believes that the data indicative of the inferred mental state of the second authoring user 19 derived from observations made using the one or more sensors 48 indicates an incorrect inferred mental state for the second authoring user 19 or wishes to disguise the mental state of the second authoring user 19, then such an operation may provide an option for the second authoring user 19 to select and transmit data that indicates an alternative mental state for the second authoring user 19.

In some implementations, operation 840 may include an operation 852 for presenting to the second authoring user at least one of an option to transmit the data indicative of the extent of congruity between the inferred mental state of the first authoring user and the inferred mental state of the second authoring user or an option not to transmit the data indicative of the extent of congruity between the inferred mental state of the first authoring user and the inferred mental state of the second authoring user as illustrated in FIG. 8f. For instance, the presentation module 38 of the authoring device 10 presenting (e.g., via the display module 213 using the user interface 44 and/or via the transmission module 212 using the network communication interface 42) to the second authoring user 19 at least one of an option to transmit (e.g., to send to a receiving user 22 or a third party user via the network communication interface 42) the data indicative of the extent of congruity between the inferred mental state (e.g., state of anger) of the first authoring user 18 and the inferred mental state (e.g., state of fear) of the second authoring user 19 or an option not to transmit the data indicative of the extent of congruity between the inferred mental state (e.g., state of anger) of the first authoring user 18 and the inferred mental state (e.g., state of fear) of the second authoring user 19.

Figure 9:
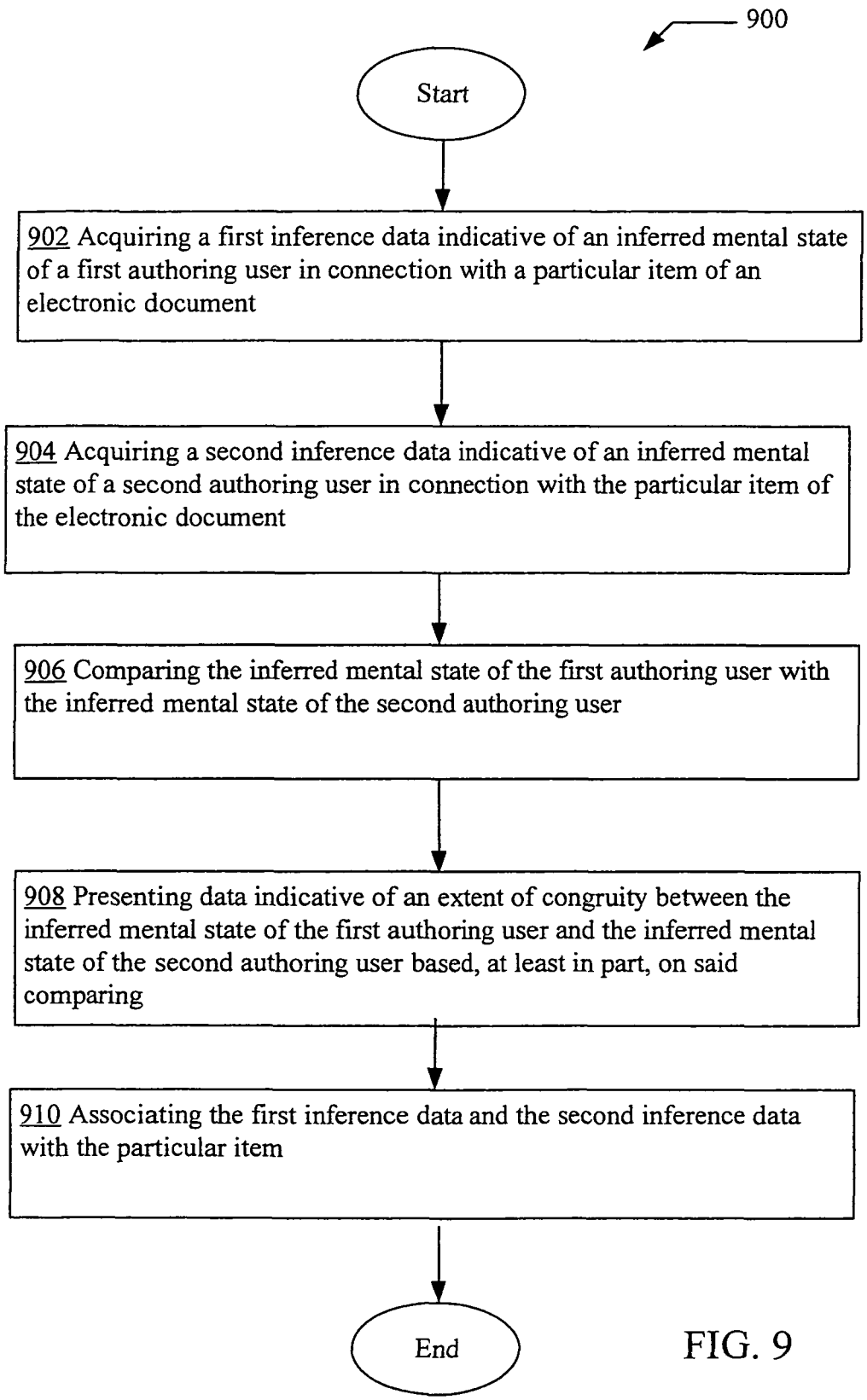
FIG. 9 is a high-level logic flowchart of another process.

Referring to FIG. 9 illustrating another operational flow 900 related to acquisition and presentation of data indicative of an extent of congruence between inferred mental states of authoring users in connection with at least a particular item of an electronic document. Operational flow 900 includes a first inference data acquisition operation 902, a second inference data acquisition operation 904, a comparison operation 906, and a presentation operation 908 that corresponds and mirrors the first inference data acquisition operation 302, the second inference data acquisition operation 304, the comparison operation 306, and the presentation operation 308, respectively, of operational flow 300 of FIG. 3.

In addition to these operations, operational flow 900 includes an association operation 910 for associating the first inference data and the second inference data with the particular item as illustrated in FIG. 9. For instance, the inference data association module 32 of the authoring device 10 associating (e.g., by inserting into the electronic document 20) the first inference data and the second inference data with the particular item 21.

In various implementations, the association operation 910 may include an inclusion operation 1002 for including into the electronic document the first inference data and the second inference data as illustrated in FIGS. 10a to 10h. For instance, the inference data inclusion module 110 of the authoring device 10 including into the electronic document 20 (e.g., in the proximate location of the particular item 21 in the electronic document 20, in the particular item 21 itself, or at other locations in the electronic document 20) the first inference data and the second inference data.

Figure 10A:
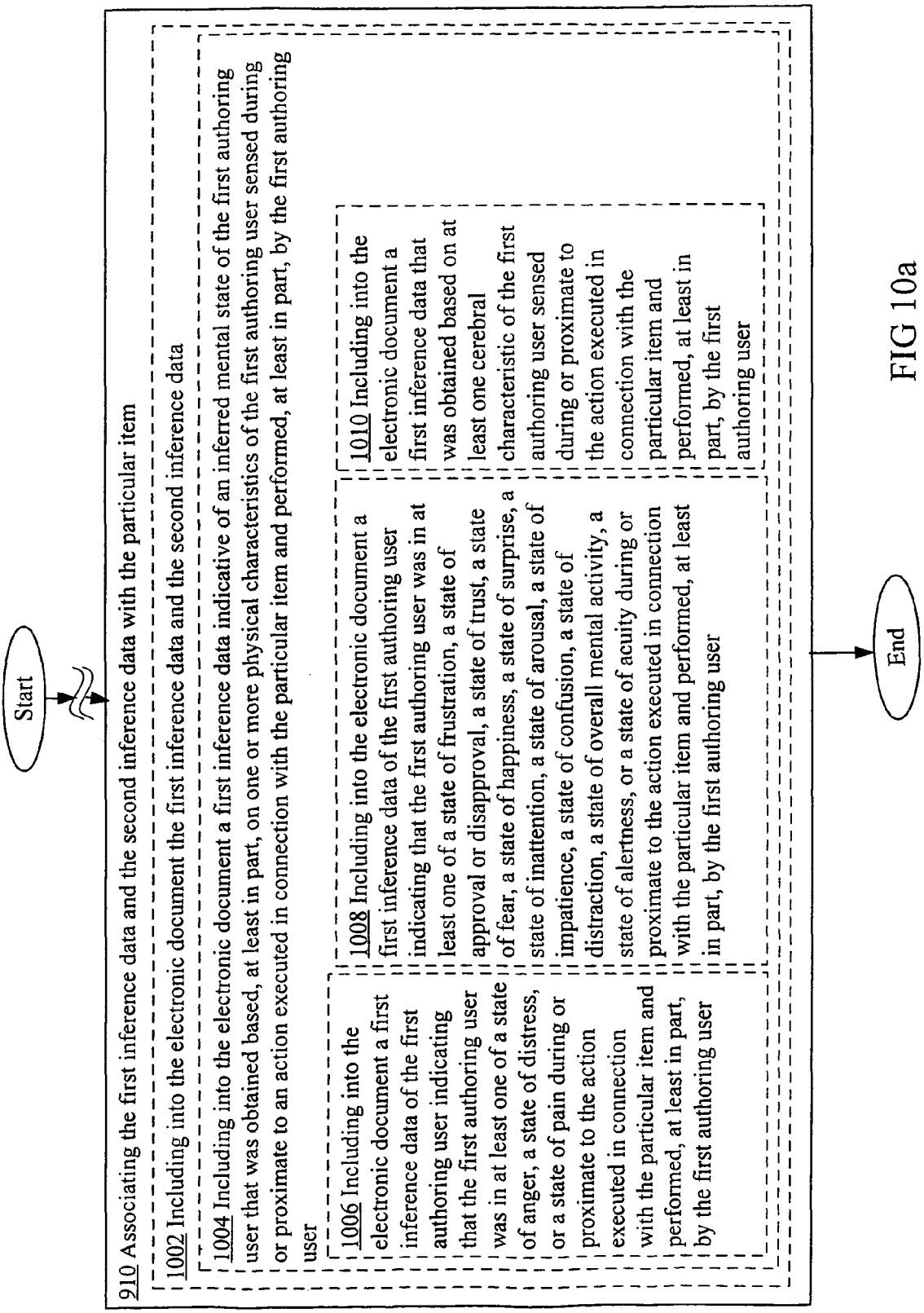
FIG. 10a is a high-level logic flowchart of a process depicting alternate implementations of the inference data association operation 910 of FIG. 9.

As further illustrated in FIGS. 10a to 10h, the inclusion operation 1002 may include one or more additional operations. For instance, in some implementations, the inclusion operation 1002 may include an operation 1004 for including into the electronic document a first inference data indicative of an inferred mental state of the first authoring user that was obtained based, at least in part, on one or more physical characteristics of the first authoring user sensed during or proximate to an action executed in connection with the particular item and performed, at least in part, by the first authoring user as illustrated in FIG. 10a. For instance, the inference data inclusion module 110 of the authoring device 10 including into the electronic document 20 a first inference data (e.g., as received by the inference data reception module 101 or as determined by the inference data determination module 102) indicative of an inferred mental state of the first authoring user 18 that was obtained based, at least in part, on one or more physical characteristics of the first authoring user 18 that was sensed (e.g., via one or more sensors 48 of the authoring device 10 or via one or more sensors 48" of a remote network device 50) during or proximate to an action (e.g., creating, modifying, deleting, or some other action) executed in connection with the particular item 21 and performed, at least in part, by the first authoring user 18.

In various implementations, operation 1004 may further include one or more additional operations. For example, in some implementations, operation 1004 may include an operation 1006 for including into the electronic document a first inference data of the first authoring user indicating that the first authoring user was in at least one of a state of anger, a state of distress, or a state of pain during or proximate to the action executed in connection with the particular item and performed, at least in part, by the first authoring user as illustrated in FIG. 10a. For instance, the inference data inclusion module 110 of the authoring device 10 including into the electronic document 20 a first inference data of the first authoring user 18 indicating that the first authoring user 18 was in at least one of a state of anger, a state of distress, or a state of pain during or proximate to the action (e.g., categorizing, substituting, inserting, or some other action) executed in connection with the particular item 21 and performed, at least in part, by the first authoring user 18.

In some implementations, operation 1004 may include an operation 1008 for including into the electronic document a first inference data of the first authoring user indicating that the first authoring user was that least one of a state of frustration, a state of approval or disapproval, a state of trust, a state of fear, a state of happiness, a state of surprise, a state of inattention, a state of arousal, a state of impatience, a state of confusion, a state of distraction, a state of overall mental activity, a state of alertness, or a state of acuity during or proximate to the action executed in connection with the particular item and performed, at least in part, by the first authoring user as illustrated in FIG. 10a. For instance, the inference data inclusion module 110 of the authoring device 10 including into the electronic document 20 a first inference data of the first authoring user 18 indicating that the first authoring user 18 was in at least one of a state of frustration, a state of approval or disapproval, a state of trust, a state of fear, a state of happiness, a state of surprise, a state of inattention, a state of arousal, a state of impatience, a state of confusion, a state of distraction, a state of overall mental activity, a state of alertness, or a state of acuity during or proximate to the action (e.g., relocating, extracting, forwarding, or some other action) executed in connection with the particular item 21 and performed, at least in part, by the first authoring user 18.

In some implementations, operation 1004 may include an operation 1010 for including into the electronic document a first inference data that was obtained based on at least one cerebral characteristic of the first authoring user sensed during or proximate to the action executed in connection with the particular item and performed, at least in part, by the first authoring user as illustrated in FIG. 10a. For instance, the inference data inclusion module 110 of the authoring device 10 including into the electronic document 20 a first inference data that was obtained based on at least one cerebral characteristic (e.g., a characteristic associated with electrical activity of a brain) of the first authoring user 18 that was sensed (e.g., via the one or more sensors 48 including an EEG device 142 and/or an MEG device 143 of the authoring device 10, or via the one or more sensors 48" of the remote network device 50) during or proximate to the action (e.g., creating, modifying, deleting, or some other action) executed in connection with the particular item 21 and performed, at least in part, by the first authoring user 18.

Figure 10B:
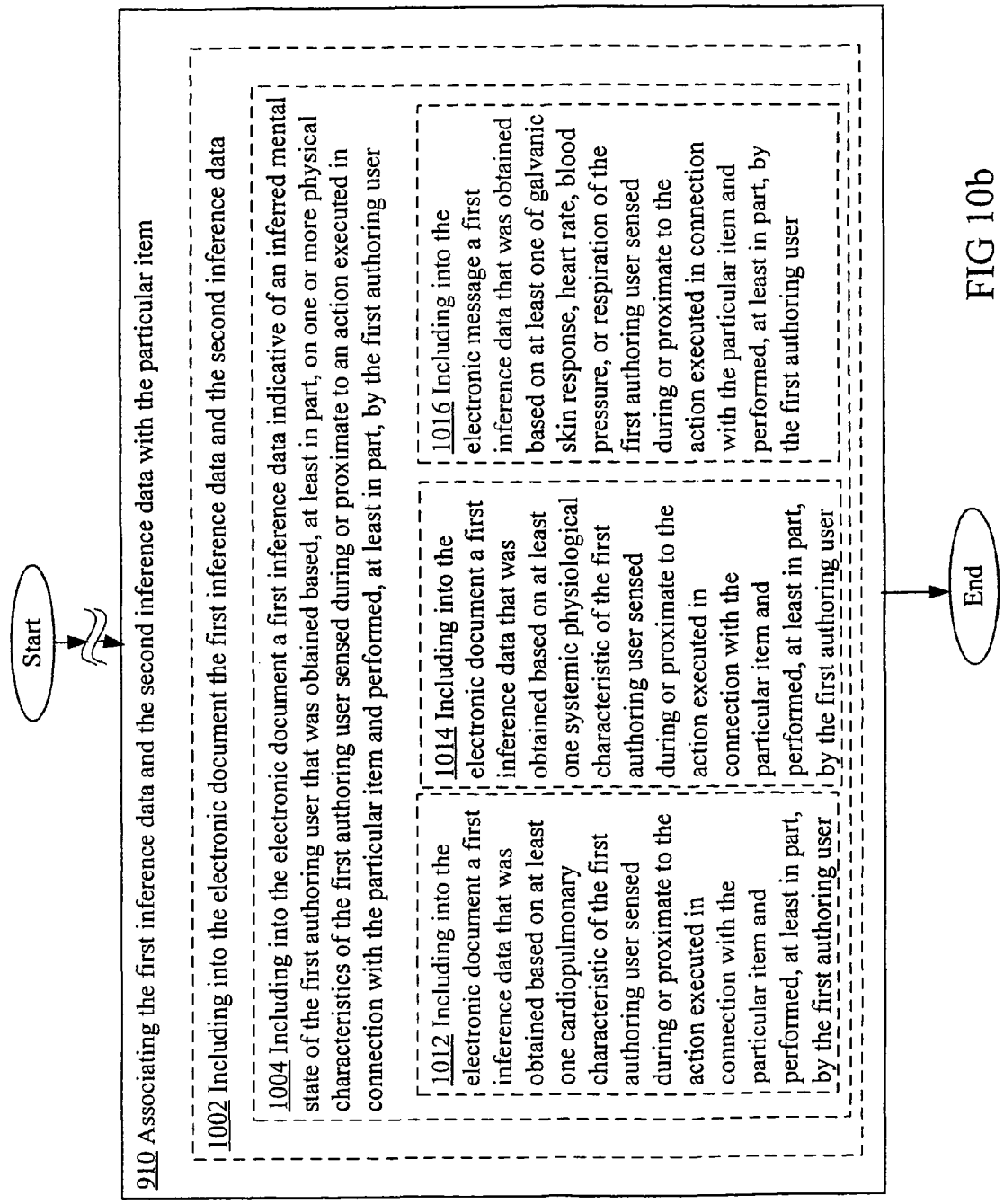
FIG. 10b is a high-level logic flowchart of a process depicting more alternate implementations of the inference data association operation 910 of FIG. 9.

In some implementations, operation 1004 may include an operation 1012 for including into the electronic document a first inference data that was obtained based on at least one cardiopulmonary characteristic of the first authoring user sensed during or proximate to the action executed in connection with the particular item and performed, at least in part, by the first authoring user as illustrated in FIG. 10b. For instance, the inference data inclusion module 110 of the authoring device 10 including into the electronic document 20 a first inference data that was obtained based on at least one cardiopulmonary characteristic (e.g., heart rate) of the first authoring user 18 that was sensed (e.g., via the one or more sensors 48 including a heart rate sensor device 145 of the authoring device 10, or via the one or more sensors 48" of the remote network device 50) during or proximate to the action (e.g., relocating, extracting, forwarding, or some other action) executed in connection with the particular item 21 and performed, at least in part, by the first authoring user 18.

In some implementations, operation 1004 may include an operation 1014 for including into the electronic document a first inference data that was obtained based on at least one systemic physiological characteristic of the first authoring user sensed during or proximate to the action executed in connection with the particular item and performed, at least in part, by the first authoring user as illustrated in FIG. 10b. For instance, the inference data inclusion module 110 of the authoring device 10 including into the electronic document 20 a first inference data that was obtained based on at least one systemic physiological characteristic (e.g., blood pressure) of the first authoring user 18 that was sensed (e.g., via the one or more sensors 48 including a blood pressure sensor device 146 of the authoring device 10, or via the one or more sensors 48" of the remote network device 50) during or proximate to the action (e.g., storing, activating or deactivating, tagging, associating, or some other action) executed in connection with the particular item 21 and performed, at least in part, by the first authoring user 18.

In some implementations, operation 1004 may include an operation 1016 for including into the electronic message a first inference data that was obtained based on at least one of galvanic skin response, heart rate, blood pressure, or respiration of the first authoring user sensed during or proximate to the action executed in connection with the particular item and performed, at least in part, by the first authoring user as illustrated in FIG. 10b. For instance, the inference data inclusion module 110 of the authoring device 10 including into the electronic document 20 a first inference data that was obtained based on at least one of galvanic skin response, heart rate, blood pressure, or respiration of the first authoring user 18 that was sensed (e.g., via the one or more sensors 48 of the authoring device 10 or via the one or more sensors 48" of the remote network device 50) during or proximate to the action (e.g., categorizing, substituting, inserting, or some other action) executed in connection with the particular item 21 and performed, at least in part, by the first authoring user 18.

Figure 10C:
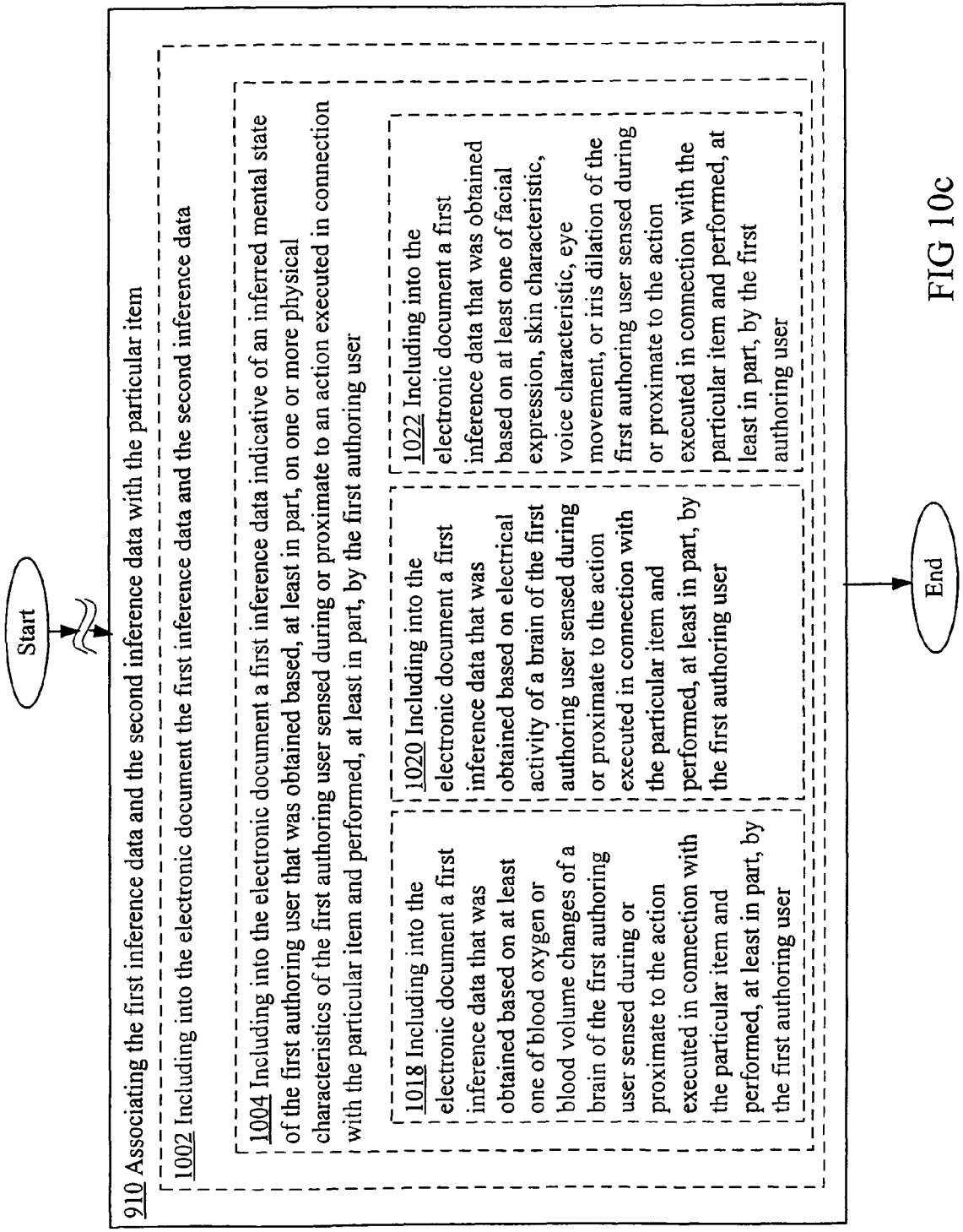
FIG. 10c is a high-level logic flowchart of a process depicting more alternate implementations of the inference data association operation 910 of FIG. 9.

In some implementations, operation 1004 may include an operation 1018 for including into the electronic document a first inference data that was obtained based on at least one of blood oxygen or blood volume changes of a brain of the first authoring user sensed during or proximate to the action executed in connection with the particular item and performed, at least in part, by the first authoring user as illustrated in FIG. 10c. For instance, the inference data inclusion module 110 of the authoring device 10 including into the electronic document 20 a first inference data that was obtained based on at least one of blood oxygen or blood volume changes of a brain of the first authoring user 18 that was sensed (e.g., via the one or more sensors 48 of the authoring device 10 or via the one or more sensors 48" of the remote network device 50) during or proximate to the action (e.g., creating, modifying, deleting, or some other action) executed in connection with the particular item 21 and performed, at least in part, by the first authoring user 18.

In some implementations, operation 1004 may include an operation 1020 for including into the electronic document a first inference data that was obtained based on electrical activity of a brain of the first authoring user sensed during or proximate to the action executed in connection with the particular item and performed, at least in part, by the first authoring user as illustrated in FIG. 10c. For instance, the inference data inclusion module 110 of the authoring device 10 including into the electronic document 20 a first inference data that was obtained based on electrical activity of a brain of the first authoring user 18 that was sensed (e.g., via the one or more sensors 48 of the authoring device 10 or via the one or more sensors 48" of the remote network device 50) during or proximate to the action (e.g., relocating, extracting, forwarding, or some other action) executed in connection with the particular item 21 and performed, at least in part, by the first authoring user 18.

In some implementations, operation 1004 may include an operation 1022 for including into the electronic document a first inference data that was obtained based on at least one of facial expression, skin characteristic, voice characteristic, eye movement, or iris dilation of the first authoring user sensed during or proximate to the action executed in connection with the particular item and performed, at least in part, by the first authoring user as illustrated in FIG. 10c. For instance, the inference data inclusion module 110 of the authoring device 10 including into the electronic document 20 a first inference data that was obtained based on at least one of facial expression, skin characteristic, voice characteristic, eye movement, or iris dilation of the first authoring user 18 that was sensed (e.g., via the one or more sensors 48 of the authoring device 10 or via the one or more sensors 48" of the remote network device 50) during or proximate to the action (e.g., storing, activating or deactivating, tagging, associating, or some other action) executed in connection with the particular item 21 and performed, at least in part, by the first authoring user 18.

Figure 10D:
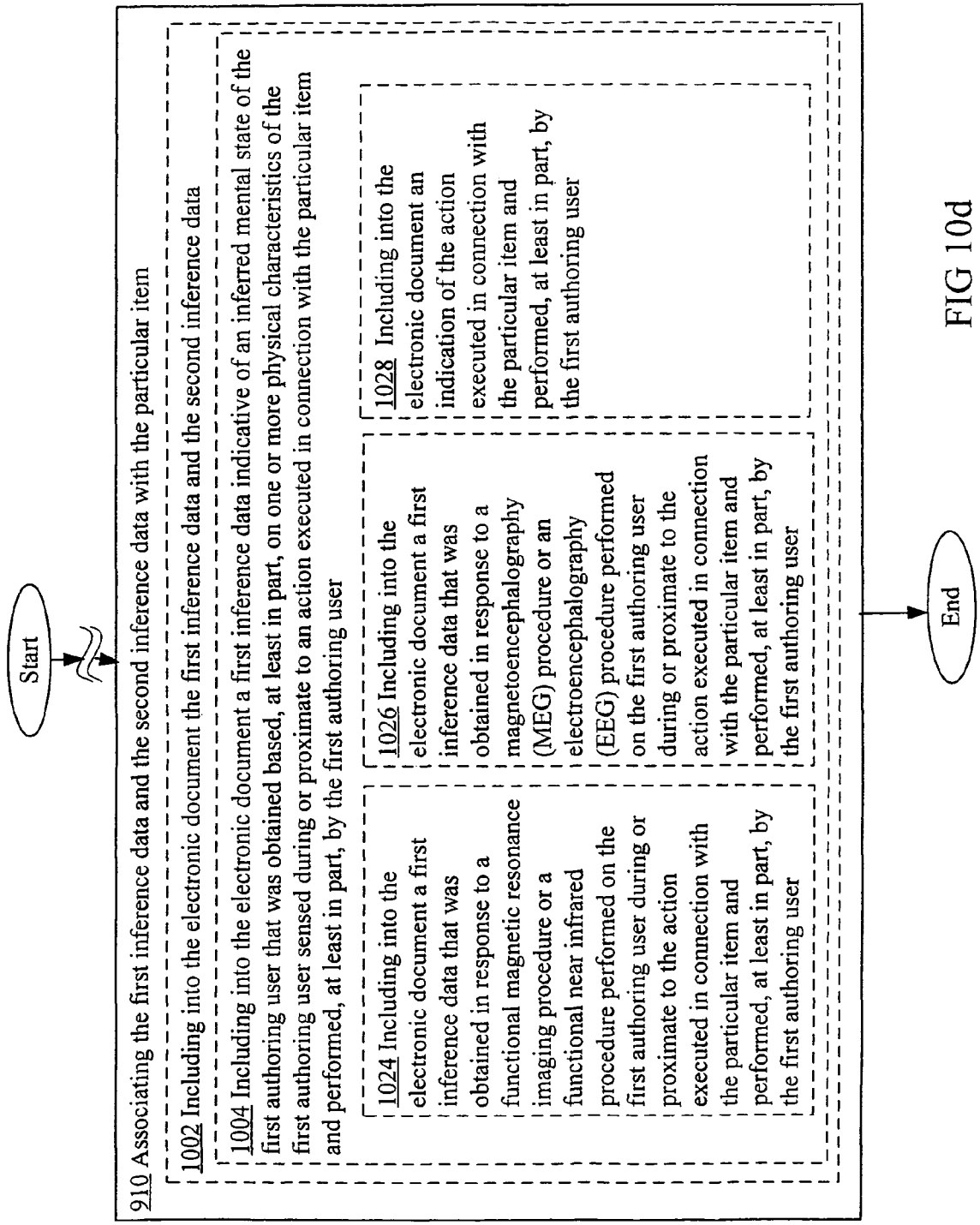
FIG. 10d is a high-level logic flowchart of a process depicting more alternate implementations of the inference data association operation 910 of FIG. 9.

In some implementations, operation 1004 may include an operation 1024 for including into the electronic document a first inference data that was obtained in response to a functional magnetic resonance imaging procedure or a functional near infrared procedure performed on the first authoring user during or proximate to the action executed in connection with the particular item and performed, at least in part, by the first authoring user as illustrated in FIG. 10d. For instance, the inference data inclusion module 110 of the authoring device 10 including into the electronic document 20 a first inference data that was obtained in response to a functional magnetic resonance imaging procedure (e.g., using an fMRI device 140) or a functional near infrared procedure (e.g., using an fNIR device 141) performed on the first authoring user 18 during or proximate to the action (e.g., creating, modifying, deleting, or some other action) executed in connection with the particular item 21 and performed, at least in part, by the first authoring user 18.

In some implementations, operation 1004 may include an operation 1026 for including into the electronic document a first inference data that was obtained in response to a magnetoencephalography (MEG) procedure or an electroencephalography (EEG) procedure performed on the first authoring user during or proximate to the action executed in connection with the particular item and performed, at least in part, by the first authoring user as illustrated in FIG. 10d. For instance, the inference data inclusion module 110 of the authoring device 10 including into the electronic document 20 a first inference data that was obtained in response to a magnetoencephalography (MEG) procedure (e.g., using an MEG device 143) or an electroencephalography (EEG) procedure (e.g., using an EEG device 142) performed on the first authoring user 18 during or proximate to the action (e.g., creating, modifying, deleting, or some other action) executed in connection with the particular item 21 and performed, at least in part, by the first authoring user 18.

In some implementations, operation 1004 may include an operation 1028 for including into the electronic document an indication of the action executed in connection with the particular item and performed, at least in part, by the first authoring user as illustrated in FIG. 10d. For instance, the inference data inclusion module 110 of the authoring device 10 including into the electronic document 20 an indication (e.g., as provided by the action module 34 of the authoring device 10) of the action (e.g., creating, modifying, deleting, relocating, extracting, forwarding, storing, activating, deactivating, tagging, associating, categorizing, substituting, inserting, or some other action) executed in connection with the particular item 21 and performed, at least in part, by the first authoring user 18.

Figure 10E:
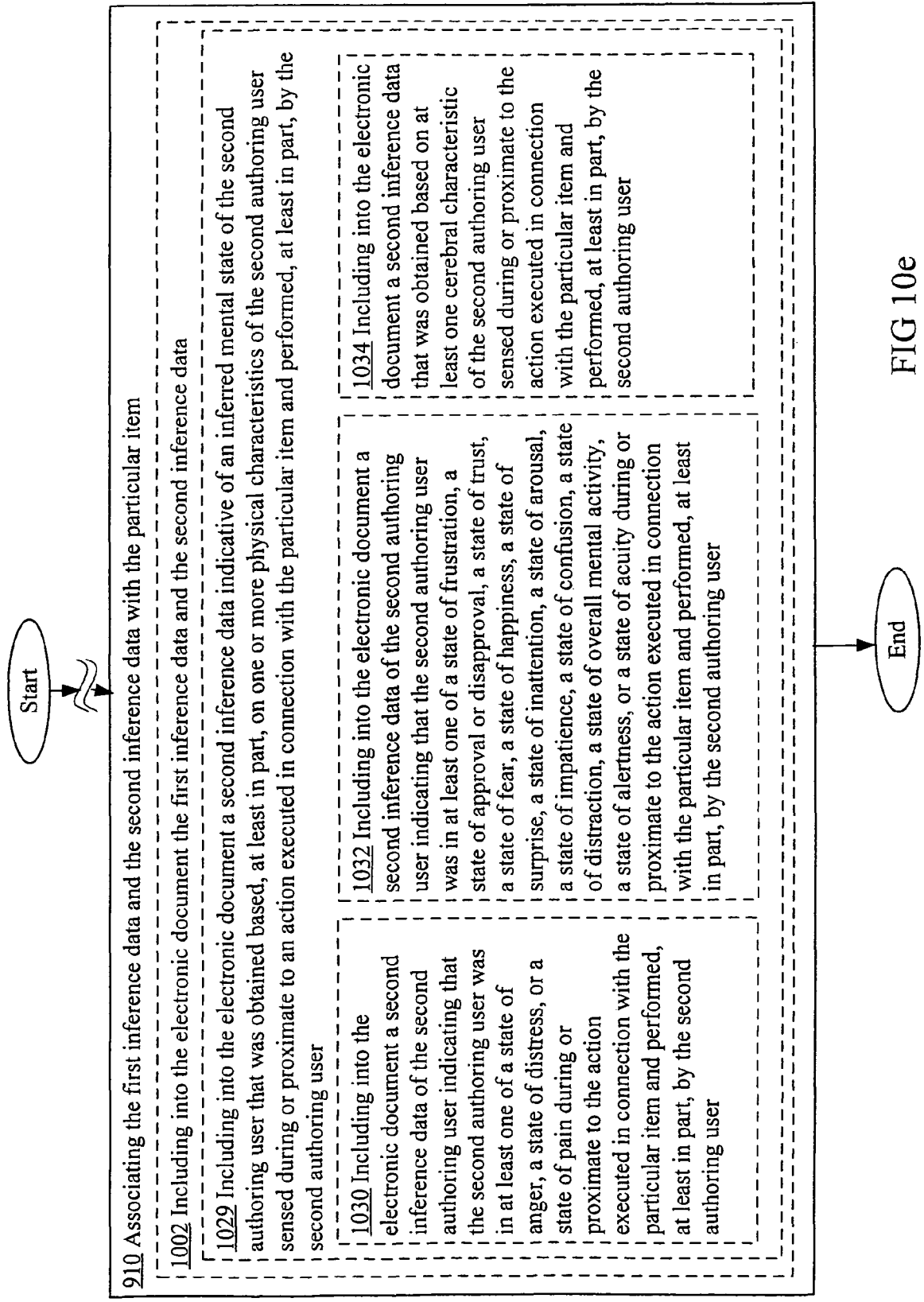
FIG. 10e is a high-level logic flowchart of a process depicting more alternate implementations of the inference data association operation 910 of FIG. 9.

Referring back to FIG. 10a, the inclusion operation 1002 may include other operations other than those described above in various alternative implementations. For example, in some implementations, the inclusion operation 1002 may include an operation 1029 for including into the electronic document a second inference data indicative of an inferred mental state of the second authoring user that was obtained based, at least in part, on one or more physical characteristics of the second authoring user sensed during or proximate to an action executed in connection with the particular item and performed, at least in part, by the second authoring user as illustrated in FIG. 10e. For instance, the inference data inclusion module 110 of the authoring device 10 including into the electronic document 20 a second inference data (e.g., as received by the inference data reception module 101 or as determined by the inference data determination module 102) indicative of an inferred mental state (e.g., a state of anger, a state of distress, a state of pain, or some other mental state) of the second authoring user 19 that was obtained based, at least in part, on one or more physical characteristics of the second authoring user 19 that was sensed (e.g., via one or more sensors 48 of the authoring device 10 or via one or more sensors 48" of the remote network device 51) during or proximate to an action (e.g., relocating, extracting, forwarding, or some other action) executed in connection with the particular item and performed, at least in part, by the second authoring user 19.

In various implementations, operation 1029 may include one or more additional operations. For example, in some implementations, operation 1029 may include an operation 1030 for including into the electronic document a second inference data of the second authoring user indicating that the second authoring user was in at least one of a state of anger, a state of distress, or a state of pain during or proximate to the action executed in connection with the particular item and performed, at least in part, by the second authoring user as illustrated in FIG. 10e. For instance, the inference data inclusion module 110 of the authoring device 10 including into the electronic document 20 a second inference data (e.g., as received by the inference data receiving module 101 or as determined by the inference data determination module 102) of the second authoring user 19 indicating that the second authoring user 19 was in at least one of a state of anger, a state of distress, or a state of pain during or proximate to the action (e.g., storing, activating, deactivating, tagging, or some other action) executed in connection with the particular item 21 and performed, at least in part, by the second authoring user 19.

In some implementations, operation 1029 may include an operation 1032 for including into the electronic document a second inference data of the second authoring user indicating that the second authoring user was in at least one of a state of frustration, a state of approval or disapproval, a state of trust, a state of fear, a state of happiness, a state of surprise, a state of inattention, a state of arousal, a state of impatience, a state of confusion, a state of distraction, a state of overall mental activity, a state of alertness, or a state of acuity during or proximate to the action executed in connection with the particular item and performed, at least in part, by the second authoring user as illustrated in FIG. 10e. For instance, the inference data inclusion module 110 of the authoring device 10 including into the electronic document 20 a second inference data (e.g., as received by the inference data receiving module 101 or as determined by the inference data determination module 102) of the second authoring user 19 indicating that the second authoring user 19 was in at least one of a state of frustration, a state of approval or disapproval, a state of trust, a state of fear, a state of happiness, a state of surprise, a state of inattention, a state of arousal, a state of impatience, a state of confusion, a state of distraction, a state of overall mental activity, a state of alertness, or a state of acuity during or proximate to the action (e.g., associating, categorizing, substituting, inserting, or some other action) executed in connection with the particular item 21 and performed, at least in part, by the second authoring user 19.

In some implementations, operation 1029 may include an operation 1034 for including into the electronic document a second inference data that was obtained based on at least one cerebral characteristic of the second authoring user sensed during or proximate to the action executed in connection with the particular item and performed, at least in part, by the second authoring user as illustrated in FIG. 10e. For instance, the inference data inclusion module 110 of the authoring device 10 including into the electronic document 20 a second inference data that was obtained based on at least one cerebral characteristic (e.g., a characteristic associated with electrical activity of a brain) of the second authoring user 19 that was sensed (e.g., via the one or more sensors 48 including an EEG device 142 and/or an MEG device 143 of the authoring device 10, or via the one or more sensors 48" of the remote network device 51) during or proximate to the action (e.g., creating, modifying, deleting, or some other action) executed in connection with the particular item 21 and performed, at least in part, by the second authoring user 19.

Figure 10F:
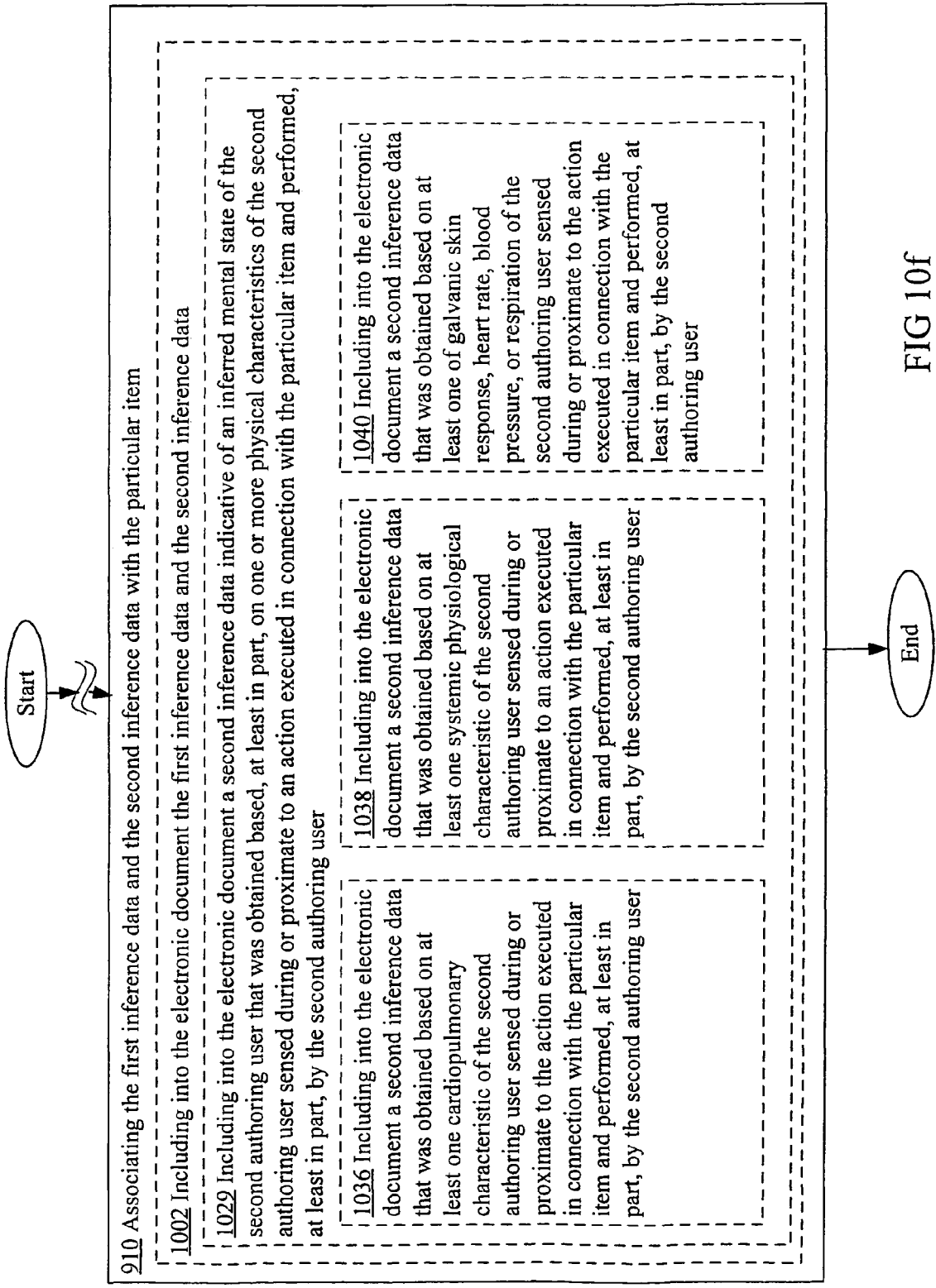
FIG. 10f is a high-level logic flowchart of a process depicting more alternate implementations of the inference data association operation 910 of FIG. 9.

In some implementations, operation 1029 may include an operation 1036 for including into the electronic document a second inference data that was obtained based on at least one cardiopulmonary characteristic of the second authoring user sensed during or proximate to the action executed in connection with the particular item and performed, at least in part, by the second authoring user as illustrated in FIG. 10f. For instance, the inference data inclusion module 110 of the authoring device 10 including into the electronic document 20 a second inference data that was obtained based on at least one cardiopulmonary characteristic (e.g., heart rate) of the second authoring user 19 that was sensed (e.g., via the one or more sensors 48 including a heart rate sensor device 145 of the authoring device 10, or via the one or more sensors 48" of the remote network device 51) during or proximate to the action (e.g., relocating, extracting, forwarding, or some other action) executed in connection with the particular item 21 and performed, at least in part, by the second authoring user 19.

In some implementations, operation 1029 may include an operation 1038 for including into the electronic document a second inference data that was obtained based on at least one systemic physiological characteristic of the second authoring user sensed during or proximate to an action executed in connection with the particular item and performed, at least in part, by the second authoring user as illustrated in FIG. 10f. For instance, the inference data inclusion module 110 of the authoring device 10 including into the electronic document 20 a second inference data that was obtained based on at least one systemic physiological characteristic (e.g., blood pressure) of the second authoring user 19 that was sensed (e.g., via the one or more sensors 48 including a blood pressure sensor device 146 of the authoring device 10, or via the one or more sensors 48" of the remote network device 51) during or proximate to an action (e.g., storing, activating or deactivating, tagging, associating, or some other action) executed in connection with the particular item 21 and performed, at least in part, by the second authoring user 19.

In some implementations, operation 1029 may include an operation 1040 for including into the electronic document a second inference data that was obtained based on at least one of galvanic skin response, heart rate, blood pressure, or respiration of the second authoring user sensed during or proximate to the action executed in connection with the particular item and performed, at least in part, by the second authoring user as illustrated in FIG. 10f. For instance, the inference data inclusion module 110 of the authoring network device 10 including into the electronic document 20 a second inference data that was obtained based on at least one of galvanic skin response, heart rate, blood pressure, or respiration of the second authoring user 19 sensed during or proximate to the action executed in connection with the particular item and performed, at least in part, by the second authoring user 19.

Figure 10G:
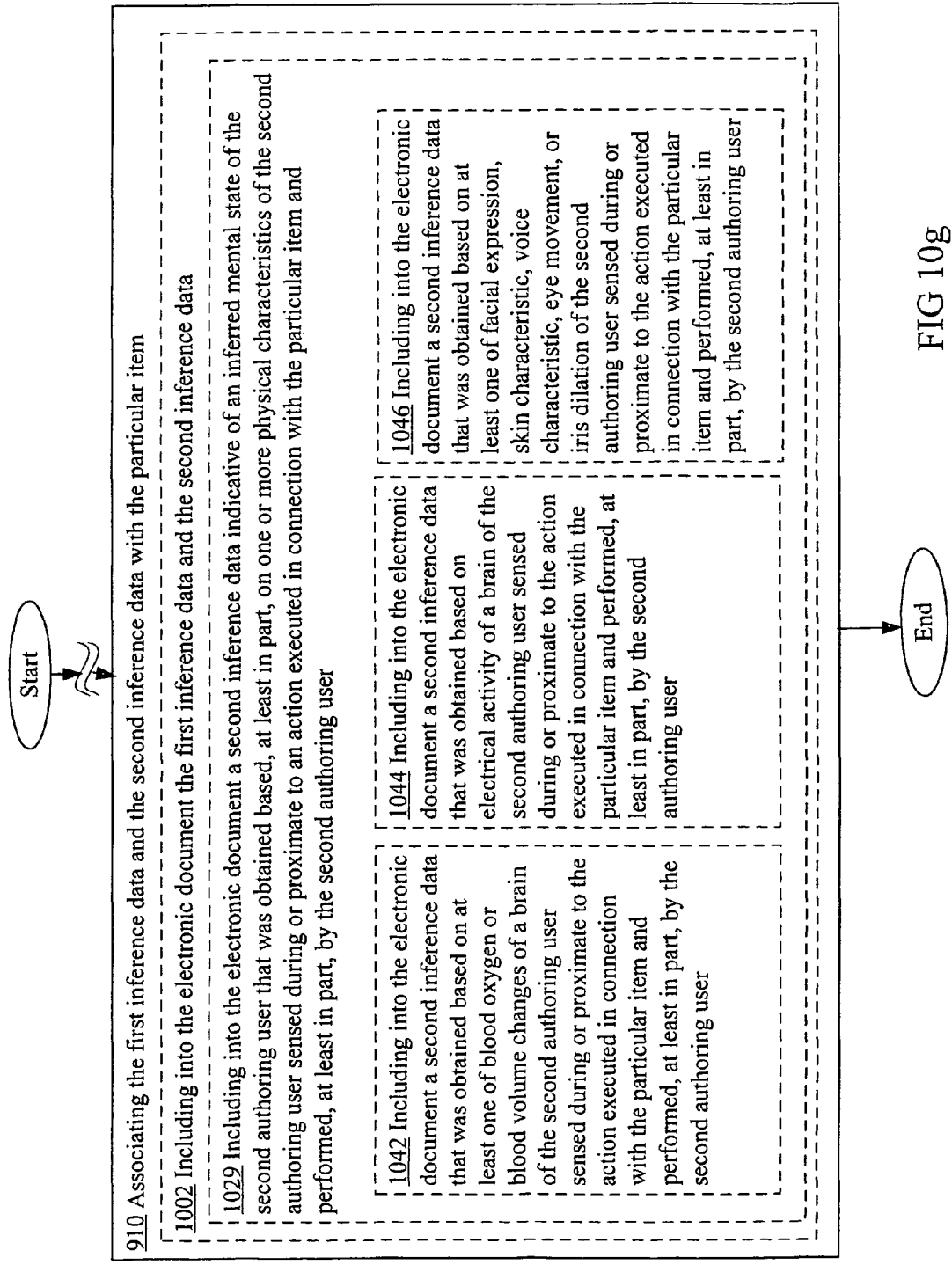
FIG. 10g is a high-level logic flowchart of a process depicting more alternate implementations of the inference data association operation 910 of FIG. 9.

In some implementations, operation 1029 may include an operation 1042 for including into the electronic document a second inference data that was obtained based on at least one of blood oxygen or blood volume changes of a brain of the second authoring user sensed during or proximate to the action executed in connection with the particular item and performed, at least in part, by the second authoring user as illustrated in FIG. 10g. For instance, the inference data inclusion module 110 of the authoring device 10 including into the electronic document 20 a second inference data that was obtained based on at least one of blood oxygen or blood volume changes of a brain of the second authoring user 19 that was sensed (e.g., via the one or more sensors 48 of the authoring device 10 or via the one or more sensors 48" of the remote network device 51) during or proximate to the action (e.g., creating, modifying, deleting, or some other action) executed in connection with the particular item 21 and performed, at least in part, by the second authoring user 19.

In some implementations, operation 1029 may include an operation 1044 for including into the electronic document a second inference data that was obtained based on electrical activity of a brain of the second authoring user sensed during or proximate to the action executed in connection with the particular item and performed, at least in part, by the second authoring user as illustrated in FIG. 10g. For instance, the inference data inclusion module 110 of the authoring device 10 including into the electronic document 20 a second inference data that was obtained based on electrical activity of a brain of the second authoring user 19 that was sensed (e.g., via the one or more sensors 48 of the authoring device 10 or via the one or more sensors 48" of the remote network device 51) during or proximate to the action (e.g., relocating, extracting, forwarding, or some other action) executed in connection with the particular item 21 and performed, at least in part, by the second authoring user 19.

In some implementations, operation 1029 may include an operation 1046 for including into the electronic document a second inference data that was obtained based on at least one of facial expression, skin characteristic, voice characteristic, eye movement, or iris dilation of the second authoring user sensed during or proximate to the action executed in connection with the particular item and performed, at least in part, by the second authoring user as illustrated in FIG. 10g. For instance, the inference data inclusion module 110 of the authoring device 10 including into the electronic document 20 a second inference data that was obtained based on at least one of facial expression, skin characteristic, voice characteristic, eye movement, or iris dilation of the second authoring user 19 that was sensed (e.g., via the one or more sensors 48 of the authoring device 10 or via the one or more sensors 48" of the remote network device 51) during or proximate to the action (e.g., storing, activating or deactivating, tagging, associating, or some other action) executed in connection with the particular item 21 and performed, at least in part, by the second authoring user 19.

Figure 10H:
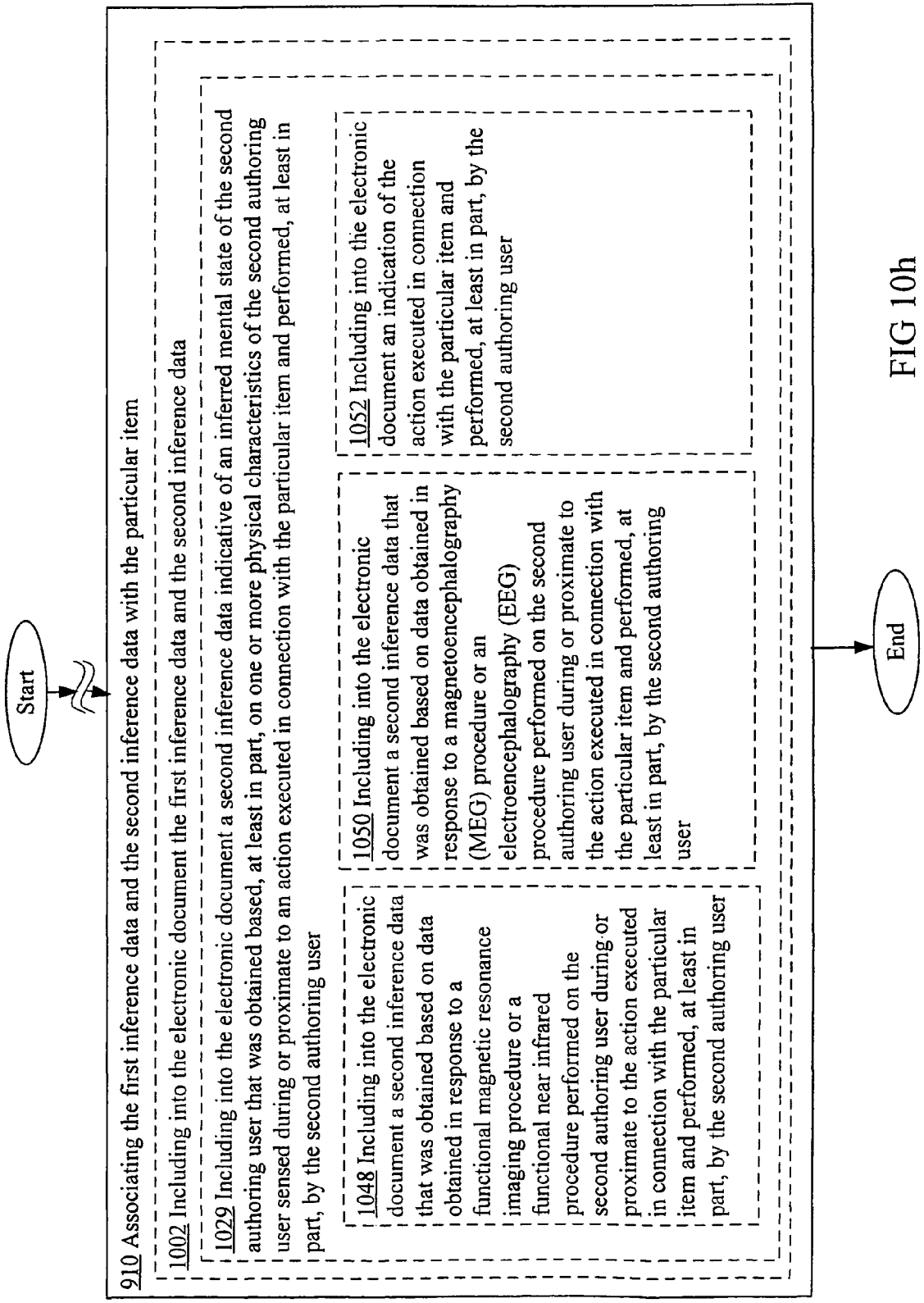
FIG. 10h is a high-level logic flowchart of a process depicting more alternate implementations of the inference data association operation 910 of FIG. 9.

In some implementations, operation 1029 may include an operation 1048 for including into the electronic document a second inference data that was obtained based on data obtained in response to a functional magnetic resonance imaging procedure or a functional near infrared procedure performed on the second authoring user during or proximate to the action executed in connection with the particular item and performed, at least in part, by the second authoring user as illustrated in FIG. 10h. For instance, the inference data inclusion module 110 of the authoring device 10 including into the electronic document 20 a second inference data that was obtained (e.g., via inference data acquisition module 30) based on data obtained in response to a functional magnetic resonance imaging procedure (e.g., using an fMRI device 140) or a functional near infrared procedure (e.g., using an fNIR device 141) performed on the second authoring user 19 during or proximate to the action (e.g., creating, modifying, deleting, or some other action) executed in connection with the particular item 21 and performed, at least in part, by the second authoring user 19.

In some implementations, operation 1029 may include an operation 1050 for including into the electronic document a second inference data that was obtained based on data obtained in response to a magnetoencephalography (MEG) procedure or an electroencephalography (EEG) procedure performed on the second authoring user during or proximate to the action executed in connection with the particular item and performed, at least in part, by the second authoring user as illustrated in FIG. 10h. For instance, the inference data inclusion module 110 of the authoring device 10 including into the electronic document 20 a second inference data that was obtained (e.g., via inference data acquisition module 30) based on data obtained in response to a magnetoencephalography (MEG) procedure (e.g., using an MEG device 143) or an electroencephalography (EEG) procedure (e.g., using an EEG device 142) performed on the second authoring user 19 during or proximate to the action (e.g., creating, modifying, deleting, or some other action) executed in connection with the particular item 21 and performed, at least in part, by the second authoring user 19.

In some implementations, operation 1029 may include an operation 1052 for including into the electronic document an indication of the action executed in connection with the particular item and performed, at least in part, by the second authoring user as illustrated in FIG. 10h. For instance, the inference data inclusion module 110 of the authoring device 10 including into the electronic document 20 an indication (e.g., as provided by the action module 34 of the authoring device 10) of the action (e.g., creating, modifying, deleting, relocating, extracting, forwarding, storing, activating, deactivating, tagging, associating, categorizing, substituting, inserting, or some other action) executed in connection with the particular item 21 and performed, at least in part, by the second authoring user 19.

Although it was described in the above description that certain physical characteristics of the authoring users 18/19 may be observed and sensed using particular sensing devices, other types of physical characteristics may also be observed and sensed using other types of sensing devices. For example, in some alternative implementations, metabolic changes associated with the authoring users 18/19 may be observed in order to determine an inferred mental state of the authoring users 18/19. Such characteristics may be observed using, for example, a positron emission tomography (PET) scanner. Other physical characteristics of the authoring users 18/19 may also be observed using various other sensing devices in order to determine the inferred mental state of authoring users 18/19 in various alternative implementations.

As indicated earlier, although the above described systems, processes, and operations were generally described with respect to two authoring users (e.g., first authoring user 18 and second authoring user 19), those skilled in the art will recognize that these systems, processes, and operations may be employed with respect to three or more authoring users. For example, with respect to the above described processes and operations, these processes and operations may be repeated again and again for a third authoring user, a fourth authoring user, and so forth.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary.

Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those having skill in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.) It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.).

In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A system comprising:
   one or more processors;
   memory coupled to the one or more processors;
   an inference data acquisition module configured to acquire inference data including at least a first inference data that indicates an inferred mental state of a first authoring user in connection with a particular item of an electronic document and a second inference data that indicates an inferred mental state of a second authoring user in connection with the particular item of the electronic document;
   a comparison module configured to compare the first inference data with the second inference data; and
   a presentation module configured to present congruence data indicative of an extent of congruity between the inferred mental state of the first authoring user in connection with one or more first actions, that were performed at least in part by the first authoring user in connection with the particular item, and the inferred mental state of the second authoring user in connection with one or more second actions, that were performed at least in part by the second authoring user in connection with the particular item, based, at least in part, on the comparison of the first inference data with the second inference data.

2. The system of claim 1, wherein said inference data acquisition module configured to acquire inference data including at least a first inference data that indicates an inferred mental state of a first authoring user in connection with a particular item of an electronic document and a second inference data that indicates an inferred mental state of a second authoring user in connection with the particular item of the electronic document comprises:
   an inference data reception module configured to receive at least the first inference data and the second inference data.

3. The system of claim 2, wherein said inference data reception module configured to receive at least the first inference data and the second inference data comprises:
   an inference data reception module configured to receive at least the first inference data and the second inference data via a network communication interface.

4. The system of claim 2, wherein said inference data reception module configured to receive at least the first inference data and the second inference data comprises:
   an inference data reception module configured to receive an indication of an action executed in connection with the particular item and performed, at least in part, by the first authoring user.

5. The system of claim 4, wherein said inference data reception module configured to receive an indication of an action executed in connection with the particular item and performed, at least in part, by the first authoring user comprises:
   an inference data reception module configured to receive an indication of another action executed in connection with the particular item and performed, at least in part, by the second authoring user.

6. The system of claim 1, wherein said inference data acquisition module configured to acquire inference data including at least a first inference data that indicates an inferred mental state of a first authoring user in connection with a particular item of an electronic document and a second inference data that indicates an inferred mental state of a second authoring user in connection with the particular item of the electronic document comprises:
   an inference data determination module configured to determine the first inference data based, at least in part, on one or more observed physical characteristics of the first authoring user and to determine the second inference data based, at least in part, on one or more observed physical characteristics of the second authoring user.

7. The system of claim 6, wherein said inference data determination module configured to determine the first inference data based, at least in part, on one or more observed physical characteristics of the first authoring user and to determine the second inference data based, at least in part, on one or more observed physical characteristics of the second authoring user comprises:
   a physical characteristic observation module configured to observe the one or more physical characteristics of the first authoring user during or proximate to a first action executed in connection with the particular item and performed, at least in part, by the first authoring user, and to observe the one or more physical characteristics of the second authoring user during or proximate to a second action executed in connection with the particular item and performed, at least in part, by the second authoring user.

8. The system of claim 1, wherein said inference data acquisition module configured to acquire inference data including at least a first inference data that indicates an inferred mental state of a first authoring user in connection with a particular item of an electronic document and a second inference data that indicates an inferred mental state of a second authoring user in connection with the particular item of the electronic document comprises:

a mental state inference module configured to infer a mental state of the first authoring user based, at least in part, on a result of an observation made of one or more physical characteristics of the first authoring user, and to infer a mental state of the second authoring user based, at least in part, on a result of an observation made of one or more physical characteristics of the second authoring user.

9. The system of claim 8, wherein said mental state inference module configured to infer a mental state of the first authoring user based, at least in part, on a result of an observation made of one or more physical characteristics of the first authoring user, and to infer a mental state of the second authoring user based, at least in part, on a result of an observation made of one or more physical characteristics of the second authoring user comprises:

a mental state inference module configured to infer mental states of the first authoring user and the second authoring user that indicates that at least on one of the first authoring user or the second authoring user was in a state of anger, a state of distress, or a state of pain during or proximate to an action executed in connection with the particular item and performed, at least in part, by the at least one of the first authoring user or the second authoring user.

10. The system of claim 8, wherein said mental state inference module configured to infer a mental state of the first authoring user based, at least in part, on a result of an observation made of one or more physical characteristics of the first authoring user, and to infer a mental state of the second authoring user based, at least in part, on a result of an observation made of one or more physical characteristics of the second authoring user comprises:

a mental state inference module configured to infer mental states of the first authoring user and the second authoring user that indicates that at least on one of the first authoring user or the second authoring user was in one of a state of frustration, a state of approval or disapproval, a state of trust, a state of fear, a state of happiness, a state of surprise, a state of inattention, a state of arousal, a state of impatience, a state of confusion, a state of distraction, a state of overall mental activity, a state of alertness, or a state of acuity during or proximate to an action executed in connection with the particular item and performed, at least in part, by the at least one of the first authoring user or the second authoring user.

11. The system of claim 1, wherein said comparison module configured to compare the first inference data with the second inference data comprises:

a mental state difference determination module configured to determine a difference between the inferred mental state of the first authoring user and the inferred mental state of the second authoring user.

12. The system of claim 1, wherein said presentation module configured to present congruence data indicative of an extent of congruity between the inferred mental state of the first authoring user in connection with one or more first actions, that were performed at least in part by the first authoring user in connection with the particular item, and the inferred mental state of the second authoring user in connection with one or more second actions, that were performed at least in part by the second authoring user in connection with the particular item, based, at least in part, on the comparison of the first inference data with the second inference data comprises:

a transmission module configured to transmit the congruence data indicative of the extent of congruity between the inferred mental state of the first authoring user and the inferred mental state of the second authoring user.

13. The system of claim 12, wherein said transmission module configured to transmit congruence data indicative of the extent of congruity between the inferred mental state of the first authoring user and the inferred mental state of the second authoring user comprises:

a transmission module configured to transmit the congruence data indicative of the extent of congruity between the inferred mental state of the first authoring user and the inferred mental state of the second authoring user via the electronic document.

14. The system of claim 12, wherein said transmission module configured to transmit the congruence data indicative of the extent of congruity between the inferred mental state of the first authoring user and the inferred mental state of the second authoring user comprises:

a transmission module configured to transmit the congruence data indicative of the extent of congruity between the inferred mental state of the first authoring user and the inferred mental state of the second authoring user via a network communication interface.

15. The system of claim 14, wherein said transmission module configured to transmit the congruence data indicative of the extent of congruity between the inferred mental state of the first authoring user and the inferred mental state of the second authoring user via a network communication interface comprises:

a transmission module configured to transmit the congruence data indicative of the extent of congruity between the inferred mental state of the first authoring user and the inferred mental state of the second authoring user to at least one of the first authoring user or the second authoring user via a communication network interface.

16. The system of claim 12, wherein said transmission module configured to transmit the congruence data indicative of the extent of congruity between the inferred mental state of the first authoring user and the inferred mental state of the second authoring user comprises:

a transmission module configured to transmit an indication of the one or more first actions that were executed in connection with the particular item and that were performed, at least in part, by the first authoring user.

17. The system of claim 12, wherein said transmission module configured to transmit the congruence data indicative of the extent of congruity between the inferred mental state of the first authoring user and the inferred mental state of the second authoring user comprises:

a transmission module configured to transmit an indication of the one or more second actions that were executed in connection with the particular item and that were performed, at least in part, by the second authoring user.

18. The system of claim 1, wherein said presentation module configured to present congruence data indicative of an extent of congruity between the inferred mental state of the first authoring user in connection with one or more first actions, that were performed at least in part by the first authoring user in connection with the particular item, and the inferred mental state of the second authoring user in connection with one or more second actions, that were performed at least in part by the second authoring user in connection with the particular item, based, at least in part, on the comparison of the first inference data with the second inference data comprises:
- a display module configured to display the congruence data indicative of the extent of congruity between the inferred mental state of the first authoring user and the inferred mental state of the second authoring user via a user interface.

19. The system of claim 18, wherein said display module configured to display the congruence data indicative of the extent of congruity between the inferred mental state of the first authoring user and the inferred mental state of the second authoring user via a user interface comprises:
- a display module configured to display the congruence data indicative of the extent of congruity between the inferred mental state of the first authoring user and the inferred mental state of the second authoring user via a display monitor.

20. The system of claim 18, wherein said display module configured to display the congruence data indicative of the extent of congruity between the inferred mental state of the first authoring user and the inferred mental state of the second authoring user via a user interface comprises:
- a display module configured to display the congruence data indicative of the extent of congruity between the inferred mental state of the first authoring user and the inferred mental state of the second authoring user via a user touch screen.

21. The system of claim 18, wherein said display module configured to display the congruence data indicative of the extent of congruity between the inferred mental state of the first authoring user and the inferred mental state of the second authoring user via a user interface comprises:
- a display module configured to display the congruence data indicative of the extent of congruity between the inferred mental state of the first authoring user and the inferred mental state of the second authoring user via a speaker system.

22. The system of claim 1, wherein said presentation module configured to present congruence data indicative of an extent of congruity between the inferred mental state of the first authoring user in connection with one or more first actions, performed at least in part by the first authoring user, in connection with the particular item and the inferred mental state of the second authoring user in connection with one or more second actions, performed at least in part by the second authoring user, in connection with the particular item based, at least in part, on the comparison of the first inference data with the second inference data comprises:
- a display module configured to display the congruence data indicative of the extent of congruity between the inferred mental state of the first authoring user and the inferred mental state of the second authoring user via at least one application.

23. The system of claim 22, wherein said display module configured to display the congruence data indicative of the extent of congruity between the inferred mental state of the first authoring user and the inferred mental state of the second authoring user via at least one application comprises:
- a display module configured to display the congruence data indicative of the extent of congruity between the inferred mental state of the first authoring user and the inferred mental state of the second authoring user via at least one of a word processing application, an email application, a text messaging application, an instant messaging (IM) application, an audio application, or a video application.

24. The system of claim 1, wherein said presentation module configured to present congruence data indicative of an extent of congruity between the inferred mental state of the first authoring user in connection with one or more first actions, that were performed at least in part by the first authoring user in connection with the particular item, and the inferred mental state of the second authoring user in connection with one or more second actions, that were performed at least in part by the second authoring user in connection with the particular item, based, at least in part, on the comparison of the first inference data with the second inference data comprises:
- a display module configured to display an indication of the one or more first actions that were executed in connection with the particular item and that were performed, at least in part, by the first authoring user.

25. The system of claim 1, wherein said presentation module configured to present congruence data indicative of an extent of congruity between the inferred mental state of the first authoring user in connection with one or more first actions, that were performed at least in part by the first authoring user in connection with the particular item, and the inferred mental state of the second authoring user in connection with one or more second actions, that were performed at least in part by the second authoring user in connection with the particular item, based, at least in part, on the comparison of the first inference data with the second inference data comprises:
- a display module configured to display an indication of the one or more second actions that were executed in connection with the particular item and that were performed, at least in part, by the second authoring user.

26. The system of claim 1, wherein said presentation module configured to present congruence data indicative of an extent of congruity between the inferred mental state of the first authoring user in connection with one or more first actions, that were performed at least in part by the first authoring user in connection with the particular item, and the inferred mental state of the second authoring user in connection with one or more second actions, that were performed at least in part by the second authoring user in connection with the particular item, based, at least in part, on the comparison of the first inference data with the second inference data comprises:
- a presentation module configured to present a symbolic representation representing the extent of congruity between the inferred mental state of the first authoring user and the inferred mental state of the second authoring user.

27. The system of claim 1, wherein said presentation module configured to present congruence data indicative of an extent of congruity between the inferred mental state of the first authoring user in connection with one or more first actions, that were performed at least in part by the first authoring user in connection with the particular item, and the inferred mental state of the second authoring user in connection with one or more second actions, that were performed at least in part by the second authoring user in connection with the particular item, based, at least in part, on the comparison of the first inference data with the second inference data comprises:
- a presentation module configured to present a first icon representing an inferred mental state of the first authoring user in proximity with a second icon representing an inferred mental state of the second authoring user.

28. The system of claim 1, wherein said presentation module configured to present congruence data indicative of an extent of congruity between the inferred mental state of the first authoring user in connection with one or more first actions, that were performed at least in part by the first authoring user in connection with the particular item, and the inferred mental state of the second authoring user in connection with one or more second actions, that were performed at least in part by the second authoring user in connection with the particular item, based, at least in part, on the comparison of the first inference data with the second inference data comprises:
    a presentation module configured to present a first number representing an inferred mental state of the first authoring user in proximity with a second number representing an inferred mental state of the second authoring user.

29. The system of claim 1, wherein said presentation module configured to present congruence data indicative of an extent of congruity between the inferred mental state of the first authoring user in connection with one or more first actions, that were performed at least in part by the first authoring user in connection with the particular item, and the inferred mental state of the second authoring user in connection with one or more second actions, that were performed at least in part by the second authoring user in connection with the particular item, based, at least in part, on the comparison of the first inference data with the second inference data comprises:
    a presentation module configured to present at least one number or icon representing a matching between an inferred mental state of the first authoring user and an inferred mental state of the second authoring user.

30. The system of claim 1, wherein said presentation module configured to present congruence data indicative of an extent of congruity between the inferred mental state of the first authoring user in connection with one or more first actions, that were performed at least in part by the first authoring user in connection with the particular item, and the inferred mental state of the second authoring user in connection with one or more second actions, that were performed at least in part by the second authoring user in connection with the particular item, based, at least in part, on the comparison of the first inference data with the second inference data comprises:
    a presentation module configured to present, prior to a transmission of the data indicative of the inferred mental state of the first authoring user or the data indicative of the inferred mental state of the second authoring user, the congruence data indicative of the extent of congruity between the inferred mental state of the first authoring user and the inferred mental state of the second authoring user.

31. The system of claim 30, wherein said presentation module configured to present, prior to a transmission of the data indicative of the inferred mental state of the first authoring user or the data indicative of the inferred mental state of the second authoring user, the congruence data indicative of the extent of congruity between the inferred mental state of the first authoring user and the inferred mental state of the second authoring user comprises:
    a presentation module configured to present to the first authoring user an option to transmit the data indicative of the inferred mental state of the first authoring user or an option not to transmit the data indicative of the inferred mental state of the first authoring user.

32. The system of claim 30, wherein said presentation module configured to present, prior to a transmission of the data indicative of the inferred mental state of the first authoring user or the data indicative of the inferred mental state of the second authoring user, the congruence data indicative of the extent of congruity between the inferred mental state of the first authoring user and the inferred mental state of the second authoring user comprises:
    a presentation module configured to present to the first authoring user an option to transmit the data indicative of the inferred mental state of the first authoring user or an option to select and transmit data indicative of an alternative mental state for the first authoring user.

33. The system of claim 30, wherein said presentation module configured to present, prior to a transmission of the data indicative of the inferred mental state of the first authoring user or the data indicative of the inferred mental state of the second authoring user, the congruence data indicative of the extent of congruity between the inferred mental state of the first authoring user and the inferred mental state of the second authoring user comprises:
    a presentation module configured to present to the first authoring user an option to transmit the congruence data indicative of the extent of congruity between the inferred mental state of the first authoring user and the inferred mental state of the second authoring user or an option not to transmit the congruence data indicative of the extent of congruity between the inferred mental state of the first authoring user and the inferred mental state of the second authoring user.

34. The system of claim 30, wherein said presentation module configured to present, prior to a transmission of the data indicative of the inferred mental state of the first authoring user or the data indicative of the inferred mental state of the second authoring user, the congruence data indicative of the extent of congruity between the inferred mental state of the first authoring user and the inferred mental state of the second authoring user comprises:
    a presentation module configured to present to the second authoring user an option to transmit the data indicative of the inferred mental state of the second authoring user or an option not to transmit the data indicative of the inferred mental state of the second authoring user.

35. The system of claim 30, wherein said presentation module configured to present, prior to a transmission of the data indicative of the inferred mental state of the first authoring user or the data indicative of the inferred mental state of the second authoring user, the congruence data indicative of the extent of congruity between the inferred mental state of the first authoring user and the inferred mental state of the second authoring user comprises:
    a presentation module configured to present to the second authoring user an option to transmit the data indicative of the inferred mental state of the second authoring user or an option to select and transmit data indicative of an alternative mental state for the second authoring user.

36. The system of claim 30, wherein said presentation module configured to present, prior to a transmission of the data indicative of the inferred mental state of the first authoring user or the data indicative of the inferred mental state of the second authoring user, the congruence data indicative of the extent of congruity between the inferred mental state of the first authoring user and the inferred mental state of the second authoring user comprises:
    a presentation module configured to present to the second authoring user an option to transmit the congruence data indicative of the extent of congruity between the inferred mental state of the first authoring user and the inferred mental state of the second authoring user or an option not to transmit the congruence data indicative of the extent of congruity between the inferred mental state of the first authoring user and the inferred mental state of the second authoring user.

37. The system of claim 1, further comprising:
an inference data association module configured to associate the first inference data and the second inference data with the particular item.

38. The system of claim 37, wherein said inference data association module configured to associate the first inference data and the second inference data with the particular item comprises:
an inference data inclusion module configured to include into the electronic document the first inference data and the second inference data.

39. The system of claim 38, wherein said inference data inclusion module configured to include into the electronic document the first inference data and the second inference data comprises:
an inference data inclusion module configured to include into the electronic document a first inference data that was obtained based, at least in part, on one or more physical characteristics of the first authoring user sensed during or proximate to an action executed in connection with the particular item and performed, at least in part, by the first authoring user.

40. The system of claim 1, further comprising:
one or more sensors.

41. The system of claim 40, wherein said one or more sensors comprises:
a functional magnetic resonance imaging (fMRI) device.

42. The system of claim 40, wherein said one or more sensors comprises:
a functional near infrared (fNIR) device.

43. The system of claim 40, wherein said one or more sensors comprises:
a magnetoencephalography (MEG) device.

44. The system of claim 40, wherein said one or more sensors comprises:
an electroencephalography (EEG) device.

45. A system, comprising:
circuitry for acquiring inference data including at least a first inference data that indicates an inferred mental state of a first authoring user in connection with a particular item of an electronic document and a second inference data that indicates an inferred mental state of a second authoring user in connection with the particular item of the electronic document;
circuitry for comparing the first inference data with the second inference data; and
circuitry for presenting congruence data indicative of an extent of congruity between the inferred mental state of the first authoring user in connection with one or more first actions that were performed at least in part by the first authoring user in connection with the particular item and the inferred mental state of the second authoring user in connection with one or more second actions that were performed at least in part by the second authoring user in connection with the particular item based, at least in part, on the comparison of the first inference data with the second inference data.

46. An article of manufacture, comprising:
a non-transitory computer storage medium bearing:
one or more instructions for acquiring inference data including at least a first inference data that indicates an inferred mental state of a first authoring user in connection with a particular item of an electronic document and a second inference data that indicates an inferred mental state of a second authoring user in connection with the particular item of the electronic document;
one or more instructions for comparing the first inference data with the second inference data; and
one or more instructions for presenting congruence data indicative of an extent of congruity between the inferred mental state of the first authoring user in connection with one or more first actions that were performed at least in part by the first authoring user in connection with the particular item and the inferred mental state of the second authoring user in connection with one or more second actions that were performed at least in part by the second authoring user in connection with the particular item based, at least in part, on the comparison of the first inference data with the second inference data.

47. A system comprising:
one or more processors;
memory coupled to the one or more processors;
an inference data acquisition module configured to acquire inference data including at least a first inference data that indicates an inferred mental state of a first authoring user in connection with a particular item of an electronic document, the acquired first inference data having been derived at least in part with one or more first sensing devices that sensed one or more characteristics of the first authoring user during and/or proximate to one or more first actions that were performed at least in part by the first authoring user in connection with the particular item, and a second inference data that indicates an inferred mental state of a second authoring user in connection with the particular item of the electronic document, the acquired second inference data having been derived at least in part with one or more second sensing devices that sensed one or more characteristics of the second authoring user during and/or proximate to one or more second actions that were performed at least in part by the second authoring user in connection with the particular item;
a comparison module configured to compare the first inference data with the second inference data; and
a presentation module configured to present data indicative of an extent of congruity between the inferred mental state of the first authoring user and the inferred mental state of the second authoring user based, at least in part, on the comparison of the first inference data with the second inference data.

\* \* \* \* \*